US010648972B2

(12) United States Patent
Heil et al.

(10) Patent No.: US 10,648,972 B2
(45) Date of Patent: *May 12, 2020

(54) MULTIPLEXED ANALYSES OF TEST SAMPLES

(71) Applicant: SomaLogic, Inc., Boulder, CO (US)

(72) Inventors: James R. Heil, Ann Arbor, MI (US); Daniel J. Schneider, Arvada, CO (US); Daniel T. Nieuwlandt, Longmont, CO (US); Sheri K. Wilcox, Longmont, CO (US); Dominic Zichi, Boulder, CO (US); Todd Gander, Louisville, CO (US); Bruce Eaton, Longmont, CO (US); Larry Gold, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/878,021

(22) Filed: Jan. 23, 2018

(65) Prior Publication Data

US 2018/0156787 A1    Jun. 7, 2018

Related U.S. Application Data

(63) Continuation of application No. 14/569,241, filed on Dec. 12, 2014, now Pat. No. 10,422,794, which is a continuation-in-part of application No. 12/859,930, filed on Aug. 20, 2010, now Pat. No. 8,945,830, which is a continuation of application No. 11/623,580, filed on Jan. 16, 2007, now abandoned.

(60) Provisional application No. 60/759,675, filed on Jan. 17, 2006.

(51) Int. Cl.
| | |
|---|---|
| *G01N 33/543* | (2006.01) |
| *G01N 33/58* | (2006.01) |
| *C40B 40/00* | (2006.01) |
| *C12Q 1/6834* | (2018.01) |
| *C12Q 1/6837* | (2018.01) |
| *C12Q 1/6832* | (2018.01) |

(52) U.S. Cl.
CPC ..... *G01N 33/54306* (2013.01); *C12Q 1/6832* (2013.01); *C12Q 1/6834* (2013.01); *C12Q 1/6837* (2013.01); *G01N 33/58* (2013.01); *C07B 2200/11* (2013.01); *C40B 40/00* (2013.01)

(58) Field of Classification Search
CPC ........ C12Q 2525/205; C12Q 2541/101; C12Q 2565/514
See application file for complete search history.

(56) References Cited

U.S. PATENT DOCUMENTS

| | | | |
|---|---|---|---|
| 4,737,453 A | 4/1988 | Primus et al. | |
| 4,752,566 A | 6/1988 | Collins et al. | |
| 4,978,608 A | 12/1990 | Kung et al. | |
| 5,124,246 A | 6/1992 | Urdea et al. | |
| 5,270,163 A | 12/1993 | Gold et al. | |
| 5,412,087 A | 5/1995 | McGall et al. | |
| 5,432,099 A | 7/1995 | Ekins et al. | |
| 5,475,096 A | 12/1995 | Gold et al. | |
| 5,556,752 A | 9/1996 | Lockhart et al. | |
| 5,567,588 A | 10/1996 | Gold et al. | |
| 5,580,737 A | 12/1996 | Polisky | |
| 5,582,981 A | 12/1996 | Toole et al. | |
| 5,639,868 A | 6/1997 | Janjic et al. | |
| 5,654,151 A | 8/1997 | Allen et al. | |
| 5,658,738 A | 8/1997 | Nadeau et al. | |
| 5,681,697 A | 10/1997 | Urdea et al. | |
| 5,705,337 A | 1/1998 | Gold et al. | |
| 5,756,291 A | 5/1998 | Griffin et al. | |
| 5,817,785 A | 10/1998 | Gold et al. | |
| 5,840,867 A * | 11/1998 | Toole ................... | C12Q 1/6811 536/23.1 |

(Continued)

FOREIGN PATENT DOCUMENTS

| | | |
|---|---|---|
| EP | 0310251 | 4/1989 |
| EP | 2172566 | 3/2015 |

(Continued)

OTHER PUBLICATIONS

Wahl, G.M. et al., Efficient transfer of large DNA fragments from agarose gels to diazobenzyloxymethyl-paper and rapid hybridization by using dextran silfate, PNAS USA, vol. 78, pp. 3683-3687 (Year: 1979).*

(Continued)

*Primary Examiner* — Teresa E Strzelecka

(74) *Attorney, Agent, or Firm* — Leydig, Voit & Mayer, Ltd.

(57) ABSTRACT

The present disclosure describes methods, devices, reagents, and kits for the detection of one or more target molecules that may be present in a test sample. In one embodiment, a test sample is contacted with an aptamer that includes a tag and has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted to an aptamer covalent complex that includes an aptamer covalently bound to its target molecule. The aptamer affinity complex (or optional aptamer covalent complex) can then be detected and/or quantified using any of a variety of methods known to one skilled in the art, including using a solid support, using mass spectrometry, and using quantitative polymerase chain reaction (Q-PCR).

10 Claims, 24 Drawing Sheets

(56) References Cited

U.S. PATENT DOCUMENTS

| | | |
|---|---|---|
| 5,843,653 A | 12/1998 | Gold et al. |
| 5,861,254 A | 1/1999 | Schneider et al. |
| 5,874,218 A | 2/1999 | Drolet et al. |
| 5,958,691 A | 9/1999 | Pieken |
| 6,114,120 A | 9/2000 | Jensen et al. |
| 6,184,364 B1 | 2/2001 | Pieken et al. |
| 6,207,446 B1 | 3/2001 | Szostak et al. |
| 6,232,462 B1 | 5/2001 | Collins et al. |
| 6,291,184 B1 | 9/2001 | Gold et al. |
| 6,329,145 B1 | 12/2001 | Janjic et al. |
| 6,344,318 B1 | 2/2002 | Gold et al. |
| 6,344,321 B1 | 2/2002 | Rabin et al. |
| 6,346,611 B1 | 2/2002 | Pagratis et al. |
| 6,458,539 B1 | 10/2002 | Gold et al. |
| 6,458,543 B1 | 10/2002 | Gold et al. |
| 6,503,715 B1 | 1/2003 | Gold et al. |
| 6,544,776 B1 | 4/2003 | Gold et al. |
| 6,716,583 B2 | 4/2004 | Gold et al. |
| 7,074,586 B1 | 7/2006 | Cheronis et al. |
| 7,368,236 B2 | 5/2008 | Gold et al. |
| 7,699,979 B2 | 4/2010 | Li et al. |
| 7,855,054 B2 | 12/2010 | Schneider et al. |
| 7,947,447 B2 | 5/2011 | Zichi et al. |
| 7,964,356 B2 | 6/2011 | Zichi et al. |
| 8,703,416 B2 | 4/2014 | Sanders et al. |
| 8,975,388 B2 | 3/2015 | Zichi et al. |
| 9,382,533 B2 | 7/2016 | Zichi et al. |
| 9,404,919 B2 | 8/2016 | Schneider et al. |
| 2002/0037506 A1 | 3/2002 | Lin et al. |
| 2003/0219801 A1 | 11/2003 | Lipshutz |
| 2003/0228603 A1 | 12/2003 | Cload et al. |
| 2004/0018508 A1 | 1/2004 | Friedman |
| 2004/0072234 A1 | 4/2004 | Parma et al. |
| 2004/0180360 A1 | 9/2004 | Wilson et al. |
| 2005/0142582 A1 | 6/2005 | Doyle et al. |
| 2005/0227225 A1 | 10/2005 | Krevolin |
| 2005/0250147 A1 | 11/2005 | Macevicz |
| 2006/0014172 A1* | 1/2006 | Muller .............. B82Y 5/00 435/6.11 |
| 2006/0057573 A1 | 3/2006 | Gold et al. |
| 2006/0105341 A1 | 5/2006 | Krause et al. |
| 2006/0234253 A1* | 10/2006 | Hasui .............. C12Q 1/6834 435/6.16 |
| 2007/0161015 A1 | 7/2007 | Zheng et al. |
| 2007/0161020 A1 | 7/2007 | Luo et al. |
| 2007/0166741 A1 | 7/2007 | Heil et al. |
| 2007/0166742 A1 | 7/2007 | Gold et al. |
| 2008/0160535 A1 | 7/2008 | Gold et al. |
| 2009/0004667 A1 | 1/2009 | Zichi et al. |
| 2011/0136099 A1 | 6/2011 | Schneider et al. |
| 2011/0245479 A1 | 10/2011 | Zichi et al. |
| 2012/0115752 A1 | 5/2012 | Zichi et al. |
| 2012/0264117 A1 | 10/2012 | Sanders et al. |
| 2014/0249043 A1 | 9/2014 | Schneider et al. |
| 2014/0296102 A1 | 10/2014 | Gold et al. |
| 2015/0197753 A1 | 7/2015 | Zichi et al. |

FOREIGN PATENT DOCUMENTS

| | | |
|---|---|---|
| GB | 2 183 661 | 6/1987 |
| JP | Hei 2-1700 A | 1/1990 |
| JP | 2009-523430 | 6/2009 |
| WO | WO 1992/14842 | 3/1992 |
| WO | WO 1992/14843 | 9/1992 |
| WO | WO 1995/0018377 | 7/1995 |
| WO | WO 1995/0021265 | 8/1995 |
| WO | WO 1996/034874 | 11/1996 |
| WO | WO 1996/0041019 | 12/1996 |
| WO | WO 1998/33941 | 8/1998 |
| WO | WO 1998/48008 | 10/1998 |
| WO | WO 1999/31275 | 6/1999 |
| WO | WO 2000/24766 | 5/2000 |
| WO | WO 2001/009159 | 2/2001 |
| WO | WO 2001/061037 | 8/2001 |
| WO | WO 2002/44726 | 6/2002 |
| WO | WO 2002/083953 | 10/2002 |
| WO | WO 2003/073106 | 9/2003 |
| WO | WO 2004/43996 | 5/2004 |
| WO | WO 2004/064760 | 8/2004 |
| WO | WO 2004/081231 | 9/2004 |
| WO | WO 2005/003294 | 1/2005 |
| WO | WO 2005/108609 | 11/2005 |
| WO | WO 2007/084886 | 7/2007 |
| WO | WO 2009/012410 | 1/2009 |
| WO | WO 2009/012420 | 1/2009 |
| WO | WO 2011/022427 | 2/2011 |

OTHER PUBLICATIONS

Stratagene Catalog, p. 39 (Year: 1988).*
Green, L.S. et al., Aptamers as Reagents for High-Throughput Screening, BioTechniques, vol. 30, pp. 1094-1110 (Year: 2001).*
Daniels et al. (Dec. 23, 2003) PNAS 100(26):15416-15421, "A tenascin-C aptamer identified by tumor cell Selex: Systematic evolution of ligands by exponential enrichment".
Latham et al. (1994)Nucleic Acids Research 22(14):2817-2822, "The application of a modified nucleotide in aptamer selection: novel thrombin aptamers containing 5-(1-pentynyl)-2' -deoxyuridine".
Lavitrano et al. (1992) Molecular Reproduction and Development 31:161-169, "The Interaction between Exogenous DNA and Sperm Cells".
Office Action dated Feb. 23, 2011 in U.S. Appl. No. 12/859,930.
Pinkel et al. (Dec. 1988) Proc. Natl. Acad. Sci. USA 85:9138-9142, "Fluorescence in situ hybridization with human chromosome-specific libraries: Detection of trisomy 21 and translocations of chromosome 4".
Sakthivel et al. (1998) Angew Chem Int Ed 37(20):2872-2875 "Expanding the Potential of DNA for Binding and Catalysis: Highly Functionalized dUTP Derivatives That are Substrates for Thermostable DNA Polymerases".
Srisawat et al. (2001) Nucleic Acids Research 29(2):1-5 "Sephadex-binding RNA ligands: rapid affinity purification of RNA from complex RNA mixtures".
Baldrich et al. (2004) Analytical Chemistry 76(23):7053-7063, "Aptasensor Development: Elucidation of Critical Parameters for Optimal Aptamer Performance".
Bock et al. (Mar. 2004) Proteomics 4(3):609-618, "Photoaptmaer arrays applied to multiplexed proteomic analysis".
Bock et al., (1992) Nature 355:564-565 "Selection of Single-Stranded DNA Molecules That Bind and Inhibit Human Thrombin".
Brodsky (2002) Mol. Cell. Proteomics 1(12):922-929, "A Microbead-based System for Identifying and Characterizing RNA-Protein Interactions by Flow Cytometry*".
Brody et al. (1999) Molecular Diagnostics 4(4):381-388, "The Use of Aptamers in Large Arrays for Molecular Diagnostics".
Cho et al. (2004) Electrophoresis 25:3730-3739, "Microbead-based affinity chromatography chip using RNA aptamer modified with photocleavable linker".
Davis et al. (Sep. 3, 2002) PNAS, 99(18):11616-11621, "Isolation of high-affinity GTP aptamers from partially structured RNA libraries".
Dewey et al. (1995) J. Am. Chem. Soc. 117: 8474-8475, "New Uridine Derivatives for Systematic Evolution of RNA Ligands by Exponential Enrichment".
DiDonato (2006) "Dissertation. Part II. Synthesis and Evaluation of Modified Nucleotides for DNA Aptamer Selection" University of North Carolina, Raleigh 30-53.
DiDonato (2006) Dissertation, University of North Carolina, Raleigh [entire paper].
Drabovich et al. (May 1, 2006) Analytical Chemistry 78(9):3171-3178, "Selection of smart aptamers by methods of kinetic capillary electrophoresis".
Drolet et al. (Aug. 1996) Nature Biotechnology 14(8):1021-1025, "An enzyme-linked oligonucleotide assay".
Eaton et al. (1997) Current Opinion in Chemical Biology 1:10-16, "The joys of in vitro selection: chemically dressing oligonucleotides to satiate protein targets".

(56) References Cited

OTHER PUBLICATIONS

Ekins and Chu (Sep. 1997) JIFCC 9(3):100-109, "Immunoassay and Other Ligand Assays: Present Status and Future Trends".
Ellington & Szostak (1990) "Selection of RNAs with ligand-specific binding activity from pools of random sequence molecules" RNA Processing meeting abstract, p84.
EP Office Action dated Feb. 28, 2011 in European application serial No. 07718147.7.
EP Search Report dated May 7, 2010 in EP application serial No. 07718147.7.
EP Search report dated Dec. 1, 2009 in EP application serial No. 08782010.6.
European Office Action dated Feb. 16, 2011 in European Application Serial No. 08782010.6.
Extended European Search Report dated Jun. 10, 2013 in European Patent Application No. 13158346.0.
Extended European Search Report dated Jun. 30, 2015 in EP 15152547.4.
Extended European Search Report dated Oct. 14, 2015 in EP 15158380.4.
Famulok and Szostak (1992) Angew. Chem. Int. Ed. Engl. 31(8): 979-988, "In Vitro Selection of Specific Ligand-binding Nucleic Acids".
Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Gold et al. (Jan. 1, 1995) Harvey Lectures 91:47-57, "The Selex Process: A Surprising Source of Therapeutic and Diagnostic Compounds".
Gold et al. (Jan. 1995) Annual Review of Biochemistry 64:763-797, "Diversity of Oligonucleotide Functions".
Hamula et al. (2006) Trends in Analytical Chemistry 25(7) "Selection and analytical ap0plications of aptamers".
IPRP dated Sep. 2, 2008 in PCT/US2007/060557.
ISR and Written Opinion dated May 15, 2008 in PCT/US2007/060557.
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kang et al. (May 29, 2007) FEBS Letters, 581(13):2497-2502, "Combinatorial selection of a RNA thioaptamer that binds to Venezuelan equine encephalitis virus capsid protein".
Kawakami et al. (1997) Nucleic Acids Symposium Series No. 37:201-202, "Evolution of a phosphorothioate RNA library during in vitro selection".
Kinzler and Vogelstein (1989) Nucleic Acids Research 17(10): 3645-3653, "Whole genome PCR: application to the identification of sequences bound by gene regulatory proteins".
Kirby et al. (2004) Anal. Chem. 76(14):4066-4075, "Aptamer-Based Sensor Arrays for the Detection and Quantitation of Proteins".
Kramer et al. (1974) J. Mol. Biol. 89: 719-736, "Evolution in vitro: sequence and phenotype of a mutant RNA resistant to ethidium bromide".
Krull et al. (Oct. 1997) J. Chromatology. B, 699:173-208, "Labeling reactions applicable to chromatography and electrophoresis of minute amounts of proteins".
Kusser (2000) Reviews in Molecular Biotechnology 74:27-38, "Chemically modified nucleic acid aptamers for in vitro selections: evolving evolution".
Kuwahara et al. (2005) Nucleic Acids Symposium Series 49:81-81, "Screening of a glutamic acid-binding aptamer from arginine-modified DNA library".
Kuwahara et al. (2006) Bioorganic & Medicinal Chemistry 14:2518-2526, "Direct PCR amplification of various modified DNAs having amino acids: Convenient preparation of DNA libraries with high-potential activities for in vitro selection".
Langer et al. (Nov. 1981) Proc. Natl. Acad. Sci. USA,78(11):6633-6637, "Enzymatic synthesis of biotin-labeled polynucleotides: Novel nucleic acid affinity probes".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
Lipshutz et al. (1995) BioTechniques 19:442-447, "Using Oligonucleotide Probe Arrays to Access Genetic Diversity".
Masud et al. (2004) Bioorganic & Medicinal Chemistry 12:1111-1120, "Sialyllactose-binding modified DNA aptamer bearing additional functionality by Selex"005.
Mori et al. (2004) Nucleic Acids Research 32(20):6120-6128, "RNA aptamers selected against the receptor activator of NF-kB acquire general affinity to proteins of the tumor necrosis factor receptor family".
Murphy et al. (2003) Nucleic Acids Research 31(18):1-8 "An improved method for the in vitro evolution of aptamers and applications in protein detection and purification.".
Office Action datedApr. 27, 2009 in U.S. Appl. No. 11/623,580.
Office Action dated Feb. 22, 2010 in U.S. Appl. No. 11/623,580.
Office Action dated Jun. 24, 2010 in U.S. Appl. No. 12/499,967.
Office Action dated Jun. 25, 2010 in U.S. Appl. No. 12/175,434.
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of E. coli promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Osborne et al. (1997) Current Opinion in Chemical Biology 1:5-9, "Aptamers as Therapeutic and Diagnostic Reagents: Problems and Prospects".
Porschewski et al. (2006) Journal of Biomolecular Screening 11(7), pp. 773-781, "Using aptamers as capture reagents in bead-based assay systems for diagnostics and hit identification".
Rhie et al. (2003) J. Biol. Chem. 278(41):39697-39705 "Characterization of 2'-Fluoro-RNA Aptamers That Bind Preferentially to Disease-associated Conformations of Prion Protein and Inhibit Conversion".
Robertson and Joyce (Mar. 1990) Nature 344: 467-468, "Selection in vitro of an RNA enzyme that specifically cleaves single-stranded DNA".
Sekiya et al. (2005) Nucleic Acids Symposium Series 49:361-362 "In vitro selection of RNA aptamers against cellular and abnormal isoform of mouse prion protein.".
Syvanen et al. (1986) Nucleic Acid Research, 14(12):5037-5048, "Fast quantification of nucleic acid hybrids by affinity-based hybrid collection".
Szostak (1988) Redesigning the Molecules of Life, (S.A. Benner ed.) Springer-Verlag Berlin Heidelberg, pp. 87-113.
Tani et al. (1998) The Japan Society for Analytical Chemistry 47(12):965-970 "Effect of charged water-soluble polymers on the extraction of membrane proteins in a Triton X-114-based aqueous micellar two-phase system".
Tarasow et al. (1999) J. Am. Chem. Soc. 121:3614-3617, "Characteristics of a RNA-Diels-Alderase Active Site".
Tarasow et al. (Sep. 1997) Nature vol. 398:54-17, "RNA-catalysed carbon-carbon bond formation".
Terpetschnig et al. (1994) Anal. Biochem. 217:197-204, "Synthesis of Squaraine-N-Hydroxysuccinimide Esters and Their Biological Application as Long-Wavelength Flurorescent Labels".
Thiesen and Bach (Jun. 1990) Nucleic Acids Res. 18(11): 3203-3209, "Target detection assay (TDA): a versatile procedure to determine DNA binding sites as demonstrated on SP1 protein".

(56) References Cited

OTHER PUBLICATIONS

Tuerk and Gold (Aug. 1990) Science 249: 505-510, "Systematic evolution of ligands by exponential enrichment: RNA ligands to bacteriophage T4 DNA polymerase".

Vaught et al. (2004) J.Am. Chem. Soc. 126:11231-11237, "T7 RNA Polymerase Transcription and 5-Position Modified UTP Derivatives".

Wang et al. (2000) RNA 6:571-583, "In vitro selection of novel RNA ligands that bind human cytomegalovirus and block viral infection".

You, Qidong et al. (Jan. 31, 2004) Medicinal Chemistry, Chemical Industry Press, pp. 32-34, with Office Action dated Mar. 31, 2016 in Chinese Patent Application No. 201180028946.3 to show relevance.

Zichi et al. (Mar. 7, 2008) Current Opinion in Chemical Biology 12(1):78-85, "Proteomics and diagnostics: Let's Get Specific, again".

* cited by examiner

FIG. 10A
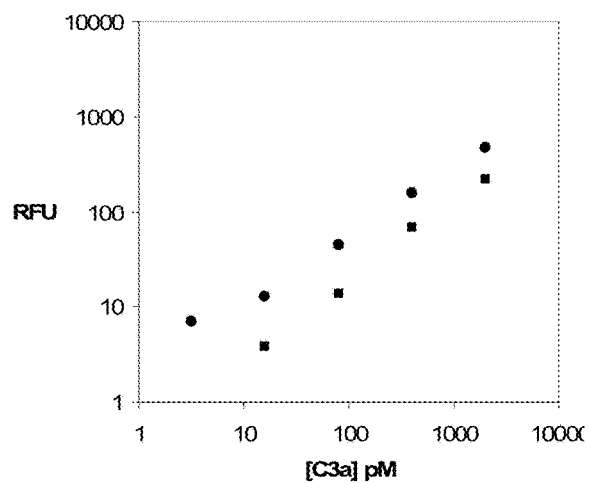
FIG. 10B
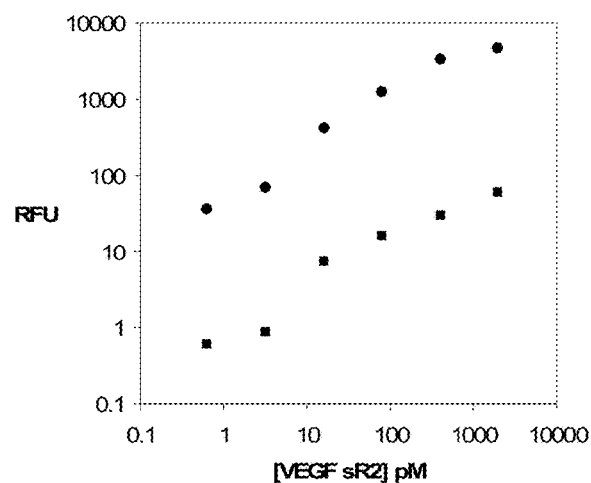
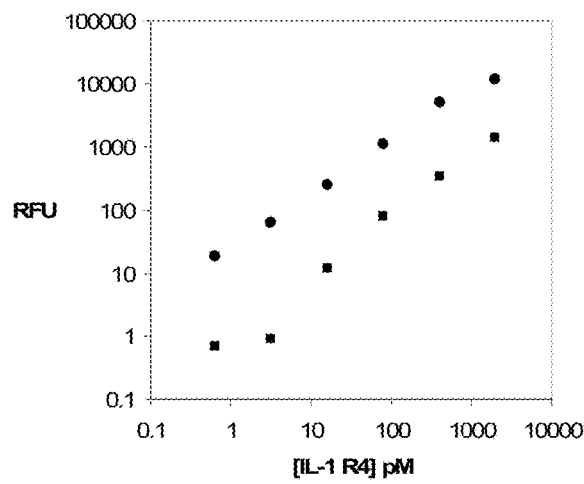
FIG. 10C
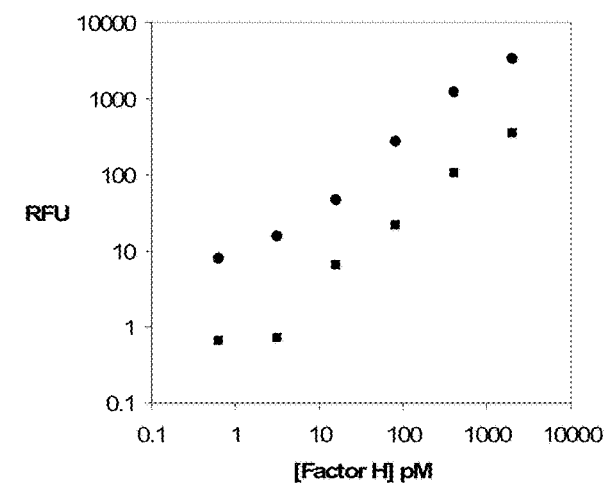
FIG. 10D

FIG. 13A
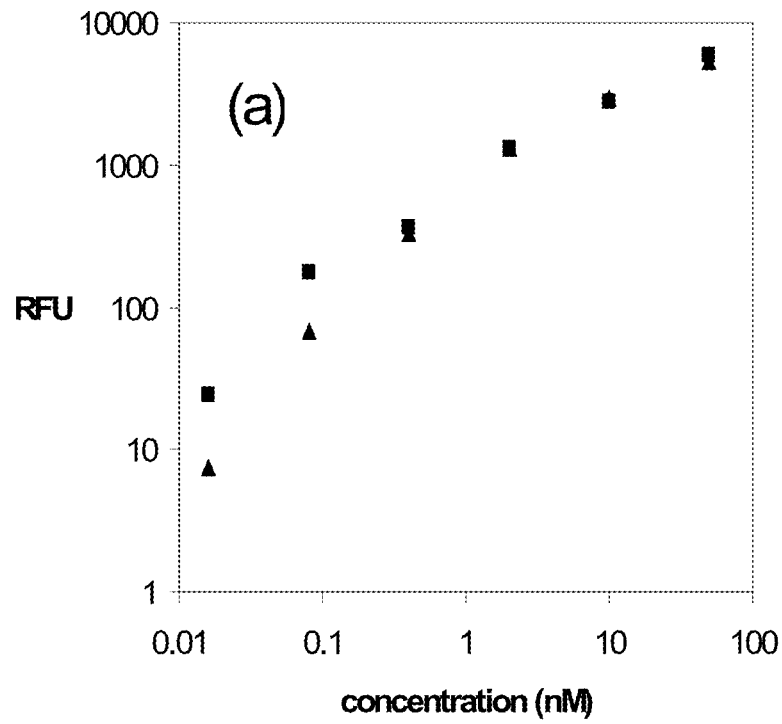
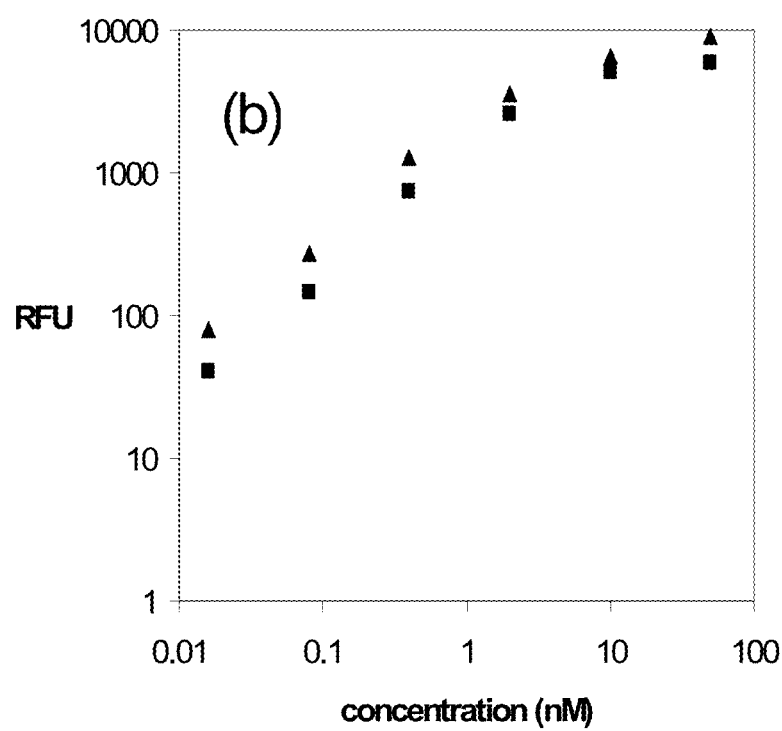
FIG. 13B

MULTIPLEXED ANALYSES OF TEST SAMPLES

RELATED APPLICATIONS

This application is a continuation application of U.S. application Ser. No. 14/569,241, filed Dec. 12, 2014, entitled "Multiplexed Analyses of Test Samples", which is a continuation of U.S. application Ser. No. 12/859,930, filed Aug. 20, 2010, entitled "Multiplexed Analyses of Test Samples", which issued as U.S. Pat. No. 8,945,830 on Feb. 3, 2015, which is a continuation application of U.S. application Ser. No. 11/623,580, filed Jan. 16, 2007, entitled "Multiplexed Analyses of Test Samples", which claims the benefit of U.S. Provisional Application Ser. No. 60/759,675, filed Jan. 17, 2006, entitled "Multiplexed Analyses of Test Samples." Each of these applications is incorporated herein by reference in its entirety.

FIELD OF THE INVENTION

The present invention relates generally to methods, devices, reagents, and kits for the detection of a target molecule in a sample and, more specifically, to the detection and/or quantification of one or more target molecules that may be contained in a test sample.

BACKGROUND

The following description provides a summary of information relevant to the present invention and is not a concession that any of the information provided or publications referenced herein is prior art to the presently claimed invention.

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands;" see also, e.g., U.S. Pat. Nos. 6,242,246, 6,458,543, and 6,503,715, each of which is entitled "Nucleic Acid Ligand Diagnostic Biochip." Once the microarray is contacted with a sample, the aptamers bind to their respective target molecules present in the sample and thereby enable a determination of the absence, presence, amount, and/or concentration of the target molecules in the sample.

A variation of this assay employs aptamers that include photoreactive functional groups that enable the aptamers to covalently bind, or "photocrosslink," their target molecules. See, e.g., U.S. Pat. No. 6,544,776 entitled "Nucleic Acid Ligand Diagnostic Biochip." These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX;" see also, e.g., U.S. Pat. No. 6,458,539, entitled "Photoselection of Nucleic Acid Ligands." After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds effected by the photoactivated functional group(s) on the photoaptamers. In this manner, the assay enables a determination of the absence, presence, amount, and/or concentration of the target molecules in the test sample.

In both of these assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Accordingly, a need exists for methods, devices, reagents, and kits that provide high sensitivity assays for the detection and/or quantification of target molecules in a test sample by optimizing conditions that affect (1) the activity of aptamers, (2) the efficiency of achieving binding equilibria for aptamer-target molecule complexes, (3) the formation of covalent bond(s) between an aptamer and its target molecule, and (4) the detection of aptamer-target molecule complexes.

SUMMARY

The present disclosure includes methods, devices, reagents, and kits for the detection and/or quantification of one or more target molecules that may be present in a test sample. In one embodiment, a test sample is contacted with an aptamer that includes a tag and has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted to an aptamer covalent complex that includes an aptamer covalently bound to its target molecule. The aptamer affinity complex (or optional aptamer covalent complex) can then be detected and/or quantified using any of a variety of methods known to one skilled in the art, including but not limited to using a solid support, using mass spectrometry, and using quantitative polymerase chain reaction (Q-PCR).

In one embodiment, the aptamer affinity complex (or optional aptamer covalent complex) is detected and/or quantified through the use of a solid support. In this embodiment, the aptamer affinity complex (or optional aptamer covalent complex) is attached to a solid support. The attachment is accomplished by contacting the solid support with the aptamer affinity complex (or optional aptamer covalent complex) and allowing a tag included on the aptamer to associate, either directly or indirectly, with a probe that is attached to the solid support. The aptamer affinity complex (or optional aptamer covalent complex) that has associated with the probe on the solid support is then detected and optionally quantified. At any point prior to detection and optional quantification, that is, either anytime before attachment or after attachment of the aptamer affinity complex (or optional aptamer covalent complex) to the solid support, the complex is contacted with a labeling agent to permit detection of the bound target molecule.

In another embodiment, the aptamer affinity complex (or optional aptamer covalent complex) is detected and/or quantified using mass spectrometry. In this embodiment, the aptamer affinity complex (or optional aptamer covalent complex) is attached to a solid support by contacting the solid support with the aptamer affinity complex (or optional aptamer covalent complex) and allowing a tag included on the aptamer to associate, either directly or indirectly, with a probe that is attached to the solid support. This facilitates the partitioning of the aptamer affinity complex (or optional aptamer covalent complex) from the remainder of the test sample, thereby concentrating the target molecule prior to mass spectrometric analysis and improving the detection and quantification of analytes from complex mixtures using this analytic tool. The aptamer affinity complex (or optional aptamer covalent complex) that has associated with the probe on the solid support is then eluted and analyzed using mass spectrometry, which produces a spectrum of peaks that can be used to identify, and therefore detect, the target molecule. Once the target molecule has been detected, optionally it can also be quantified by standard techniques known to one skilled in the art. In one embodiment where the target molecule is a protein, prior to using mass spectrometry to analyze the aptamer affinity complex (or optional aptamer covalent complex), the aptamer affinity complex (or optional aptamer covalent complex) can be digested with protease enzymes, such as, for example, proteinase K or trypsin, to produce fragments of the bound target molecule that can then be used to identify the target molecule, and thereby enable detection and optional quantification of the target molecule.

In a further embodiment, the aptamer affinity complex (or optional aptamer covalent complex) is detected and/or quantified using Q-PCR. In this embodiment, free aptamer in the test sample is partitioned from the aptamer affinity complex (or optional aptamer covalent complex) prior to detection and/or quantification. The aptamer affinity complex (or optional aptamer covalent complex) is quantified by performing PCR and determining, either directly or indirectly, the amount or concentration of aptamer that had bound to its target molecule in the test sample. The amount or concentration of the target molecule in the test sample is generally directly proportional to the amount or concentration of the aptamer quantified by using Q-PCR. An exemplary method that may be employed to quantify an aptamer affinity complex (or optional aptamer covalent complex) in this manner is the TaqMan® assay (PE Biosystems, Foster City, Calif.; see also U.S. Pat. No. 5,210,015).

BRIEF DESCRIPTION OF THE FIGURES

FIGS. 10A-10D show dose response curves for four target proteins crosslinked in buffer and added to plasma prior to the optional removal of free aptamer using $K^+$/SDS precipitation (●) compared with curves generated without removing free aptamer (■). The signal is increased upon removal of free aptamer and the dynamic range of the measurements is generally increased.

FIGS. 13A and 13B show the dose response curve generated with direct labeling of target protein (▲) or biotinylation followed by fluorescent labeled streptavidin (■) on a Schott Nexterion surface (FIG. 13A) or a methacrylate copolymer surface (FIG. 13B). Both surfaces perform well and the two labeling strategies are comparable.

DETAILED DESCRIPTION

The practice of the invention disclosed herein employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

As used in this specification, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The present disclosure includes methods, devices, reagents, and kits for the detection and/or quantification of one or more target molecules that may be present in a test sample. The disclosed methods, devices, reagents, and kits provide high sensitivity assays for the detection and/or quantification of target molecules in a test sample by optimizing conditions that affect (1) the activity of aptamers, (2) the efficiency of achieving binding equilibria for aptamer-target molecule complexes, (3) the formation of covalent bond(s) between an aptamer and its target molecule, and (4) the detection of aptamer-target molecule complexes.

Figure 1A:
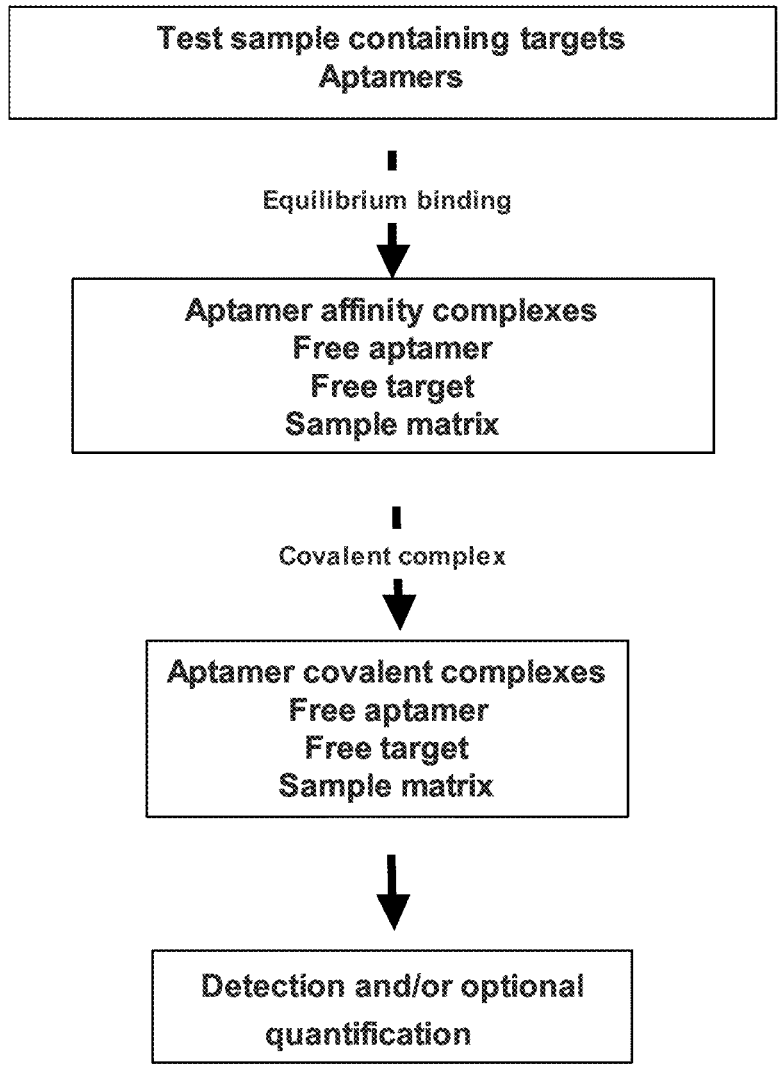
FIGS. 1A and 1B illustrate exemplary methods for the detection and/or quantification of one or more target molecules that may be present in a test sample.
Figure 1B:
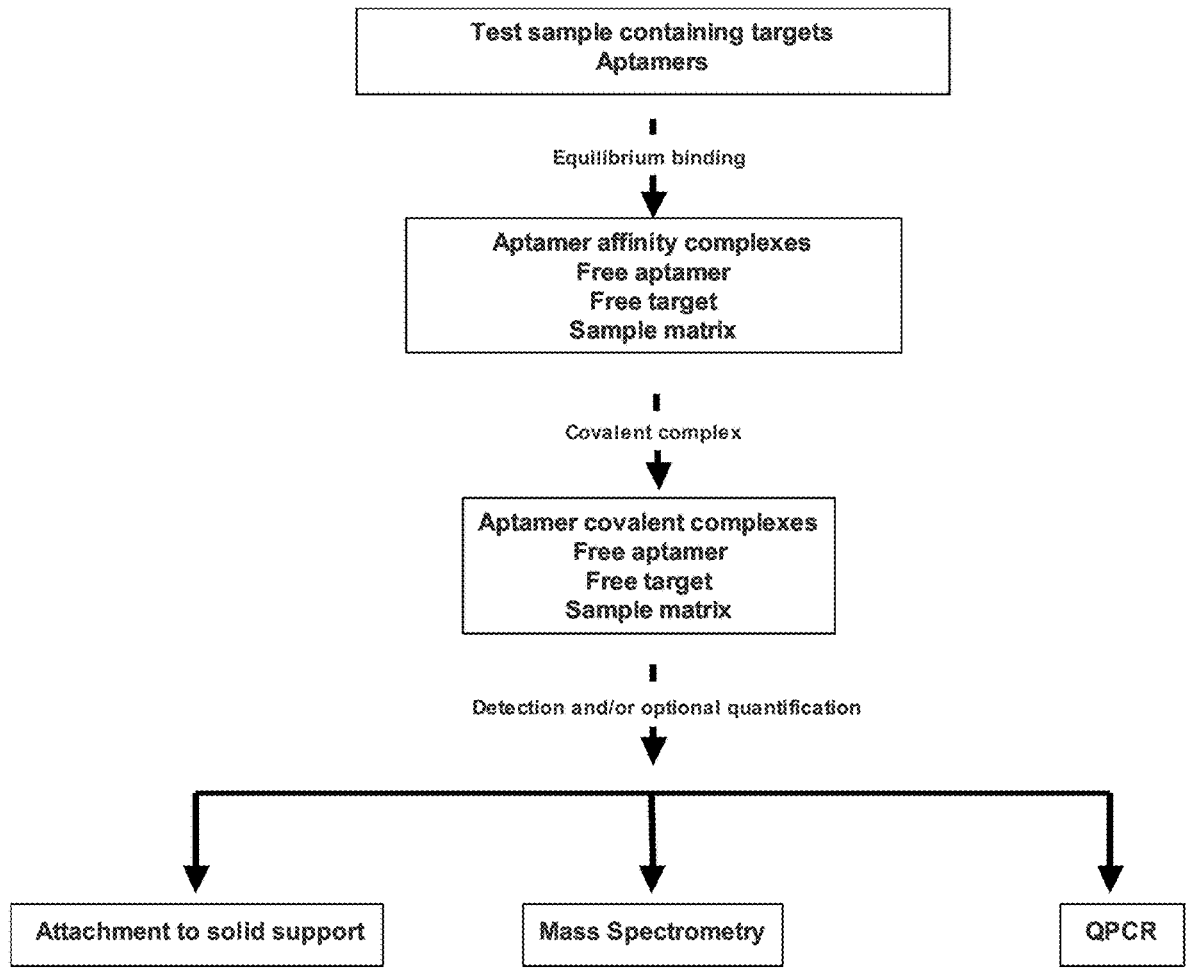

With reference to FIGS. 1A and 1B, the presence of a target molecule in a test sample is detected and/or quantified by first contacting a test sample with an aptamer that has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted, using a method appropriate to the aptamer being employed, to an aptamer covalent complex that includes an aptamer covalently bound to its target molecule. The aptamer affinity complex (or optional aptamer covalent complex) is then detected and/or quantified.

Figure 2A:
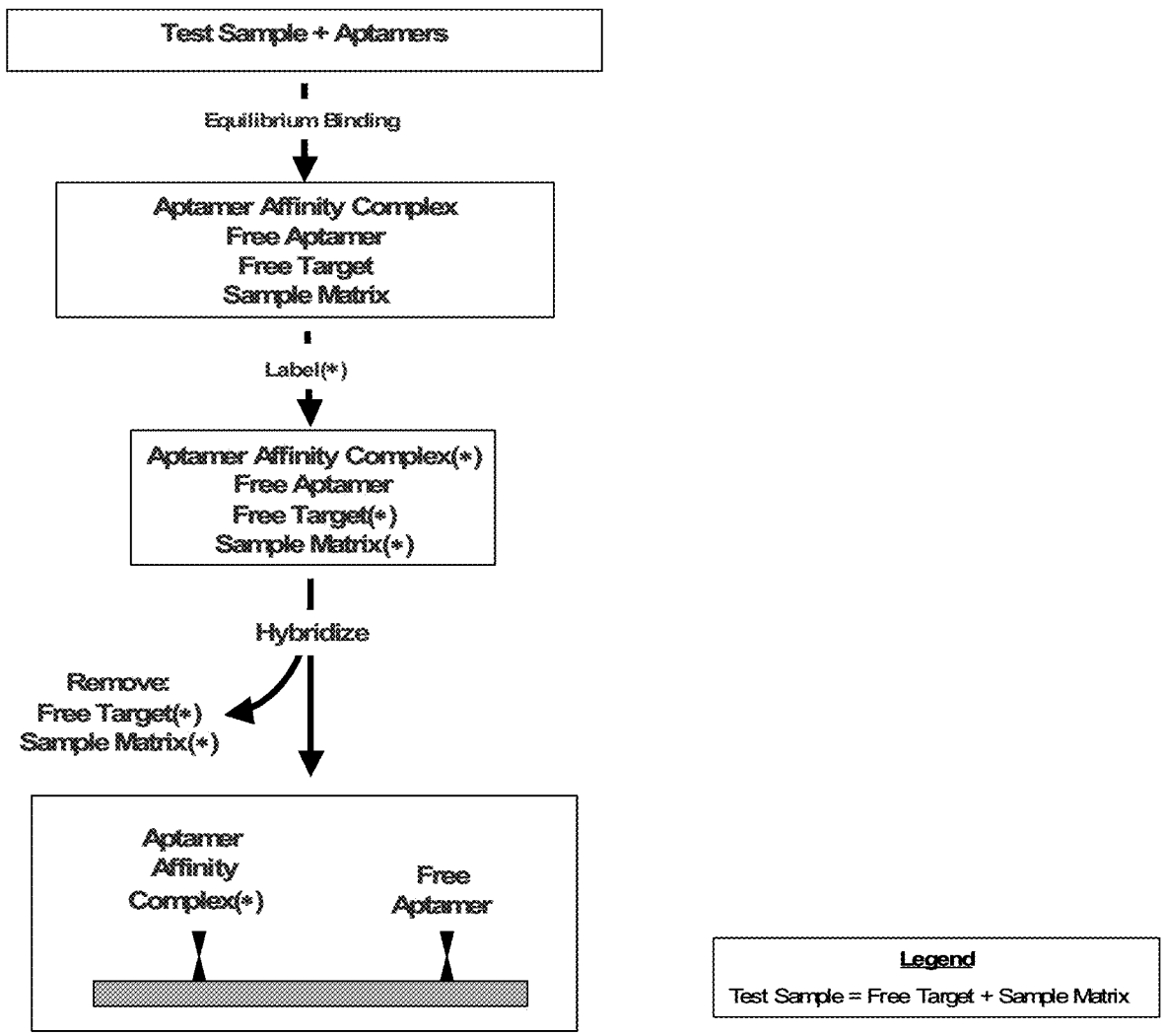
FIGS. 2A, 2B, and 2C illustrate exemplary methods for the detection and/or quantification of one or more target molecules that may be present in a test sample.
Figure 2B:
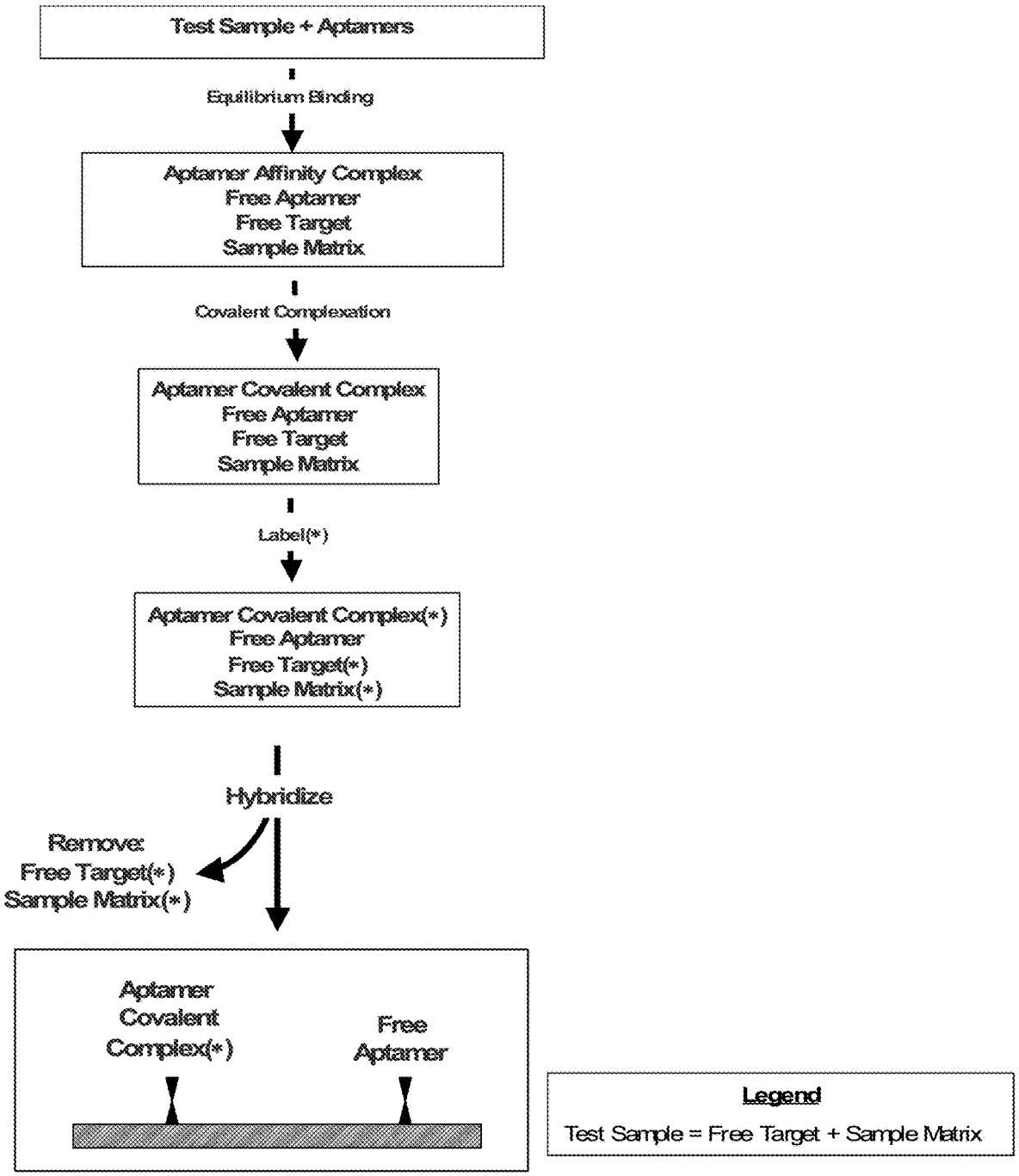
Figure 2C:
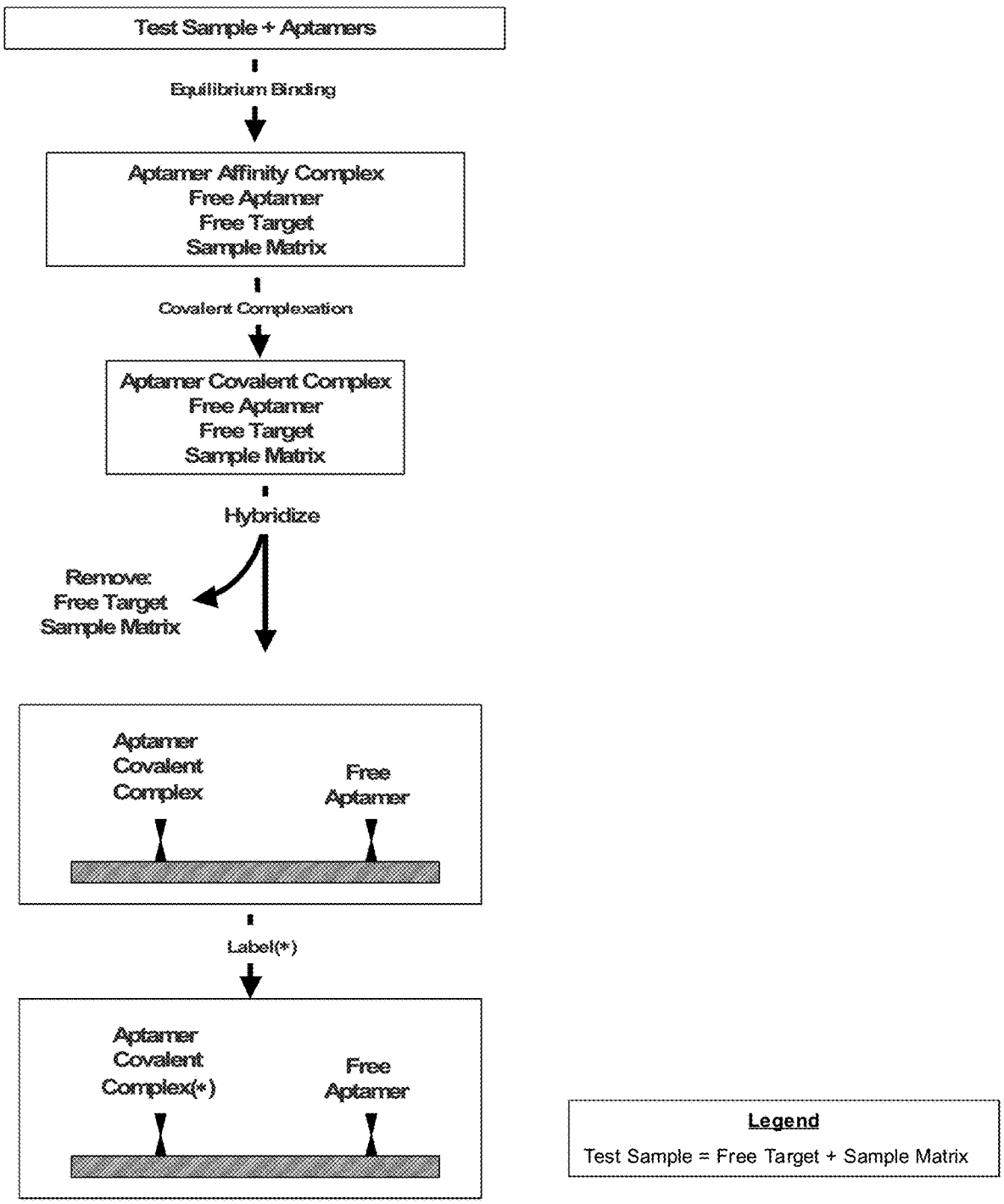

In one embodiment, the aptamer affinity complex (or optional aptamer covalent complex) is detected and/or quantified by attaching the aptamer affinity complex (or optional aptamer covalent complex) to a solid support. With reference to FIGS. 2A, 2B, and 2C, in an exemplary method for the detection and/or quantification of a target molecule that may be present in a test sample, a test sample is contacted with an aptamer that includes a tag and has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted, using a method appropriate to the aptamer being employed, to an aptamer covalent complex that includes an aptamer covalently bound to its target molecule. The aptamer affinity complex (or optional aptamer covalent complex) is attached to a solid support. The attachment is accomplished by contacting the solid support with the aptamer affinity complex (or optional aptamer covalent complex) and allowing the tag included on the aptamer to associate, either directly or indirectly, with a probe that is attached to the solid support. The aptamer affinity complex (or optional aptamer covalent complex) that has associated with the probe on the solid support is then detected and optionally quantified. At any point prior to detection and optional quantification, that is, either anytime before attachment or after attachment of the aptamer affinity complex (or optional aptamer covalent complex) to the solid support, the complex is contacted with a labeling agent to permit detection of the bound target molecule.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

If present, chemical modifications of a nucleotide can include, singly or in any combination, 2'-position sugar modifications, 5-position pyrimidine modifications (e.g, 5-(N-benzylcarboxamide)-2'-deoxyuridine, 5-(N-isobutylcarboxyamide)-2'-deoxyuridine, 5-(N-[2-(1H-indole-3yl) ethyl]carboxyamide)-2'-deoxyuridine, 5-(N-[1-(3-trimethylammonium) propyl]carboxyamide)-2'-deoxyuridine chloride, 5-(N-napthylcarboxyamide)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

As used herein, "aptamer" and "nucleic acid ligand" are used interchangeably to refer to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides. "Aptamers" refers to more than one such set of molecules. Different aptamers may have either the same or different numbers of nucleotides. Any of the methods disclosed herein may include the use of one or more aptamers. Any of the methods disclosed herein may also include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers may have either the same tag or a different tag.

An aptamer can be identified using any known method, including the SELEX process. See, e.g., U.S. Pat. No. 5,475,096 entitled "Nucleic Acid Ligands." Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. See, e.g., U.S. Pat. No. 5,475,096 entitled "Nucleic Acid Ligands." The SELEX process may be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

As disclosed herein, an aptamer can further comprise a "tag," which refers to a component that provides a means for attaching or immobilizing an aptamer (and any target molecule that is bound to it) to a solid support. A "tag" is a set of copies of one type or species of component that is capable of associating with a probe. "Tags" refers to more than one such set of components. The tag can be attached to or included in the aptamer by any method known in the art. Generally, the tag allows the aptamer to associate, either directly or indirectly, with a probe that is attached to the solid support. A tag can enable the localization of an aptamer covalent complex to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX is used to identify an aptamer, the tag may be added to the aptamer either pre- or post-SELEX. In one embodiment, the tag is included on the 5'-end of the aptamer post-SELEX. In another embodiment, the tag is included on the 3'-end of the aptamer post-SELEX.

In one embodiment, the tag includes a polynucleotide that is designed to associate directly with a probe that includes a complementary polynucleotide sequence by hybridizing directly with the probe sequence. In this embodiment, the tag is generally configured and the hybridization reaction is carried out under conditions such that the tag does not hybridize with a probe other than the probe for which the tag includes a perfect complement.

In some embodiments, the tag comprises nucleotides that are a part of the aptamer itself. For example, if SELEX is used to identify an aptamer, the aptamer generally includes a 5'-fixed end separated from a 3'-fixed end by a nucleotide sequence that varies, depending upon the aptamer, that is, a variable region. In one embodiment, the tag can comprise any suitable number of nucleotides included in a fixed end of the aptamer, such as, for example, an entire fixed end or any portion of a fixed end, including nucleotides that are internal to a fixed end. In another embodiment, the tag can comprise any suitable number of nucleotides included within the variable region of the aptamer, such as, for example, the entire variable region or any portion of the variable region. In a further embodiment, the tag can comprise any suitable number of nucleotides that overlap both the variable region and one of the fixed ends, that is, the tag can comprise a nucleotide sequence that includes any portion (including all) of the variable region and any portion (including all) of a fixed end.

In another embodiment, a tag can associate directly with a probe and covalently bind to the probe, thereby covalently linking the aptamer to the surface of the solid support. In this embodiment, the tag and the probe can include suitable reactive groups that, upon association of the tag with the probe, are sufficiently proximate to each other to undergo a chemical reaction that produces a covalent bond. The reaction may occur spontaneously or may require activation, such as, for example, photo-activation or chemical activation. In an exemplary embodiment, the tag includes a diene moiety and the probe includes a dienophile, and covalent bond formation results from a spontaneous Diels-Alder conjugation reaction of the diene and dienophile. Any appropriate complementary chemistry can be used, such as, for example, N-Mannich reaction, disulfide formation, Curtius reaction, Aldol condensation, Schiff base formation, and Michael addition.

In another embodiment, the tag associates indirectly with a probe, such as, for example, through a linker molecule, as further described below. In this embodiment, the tag can include a polynucleotide sequence that is complementary to a particular region or component of a linker molecule. The tag is generally configured and the hybridization reaction is carried out such that the tag does not hybridize with a polynucleotide sequence other than the polynucleotide sequence included in the linker molecule.

If the tag includes a polynucleotide, the polynucleotide can include any suitable number of nucleotides. In one embodiment, a tag includes at least about 10 nucleotides. In another embodiment, the tag includes from about 10 to about 45 nucleotides. In yet another embodiment, the tag includes at least about 30 nucleotides. Different tags that include a polynucleotide can include either the same number of nucleotides or a different number of nucleotides.

As used herein, the term "about" represents an insignificant modification or variation of the numerical values such that the basic function of the item to which the numerical value relates is unchanged.

As used herein, "associate," "associates," and any variation thereof refers to an interaction or complexation between a tag and a probe resulting in a sufficiently stable complex so as to permit separation of "unassociated" or unbound materials, such as, for example, unbound components of a test sample, from the tag-probe complex under given complexation or reaction conditions. A tag and a probe can associate with each other directly by interacting and binding to each other with specificity. A tag and a probe can also associate with each other indirectly such as when their complexation is mediated by a linker molecule.

As used herein, "probe" refers to a molecule that is configured to associate, either directly or indirectly, with a tag. A "probe" is a set of copies of one type of molecule or one type of multi-molecular structure that is capable of immobilizing an aptamer to a solid support by associating, either directly or indirectly, with a tag. "Probes" refers to more than one such set of molecules. A probe can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a tag (or linker molecule) can be designed or configured to bind or otherwise associate with specificity. A probe can be attached to a solid support either covalently or non-covalently by any method known in the art.

In one embodiment, the probe includes a polynucleotide that has a sequence that is complementary to a polynucleotide tag sequence. In this embodiment, the probe sequence is generally configured and the hybridization reaction is carried out under conditions such that the probe does not hybridize with a nucleotide sequence other than the tag for which the probe includes the complementary sequence (i.e., the probe is generally configured and the hybridization reaction is carried out under conditions such that the probe does not hybridize with a different tag or an aptamer).

In another embodiment, the probe associates indirectly with a tag, for example, through a linker molecule. In this embodiment, the probe can include a polynucleotide sequence that is complementary to a particular region or component of a linker molecule. The probe is generally configured and the hybridization reaction is carried out such that the probe does not hybridize with a polynucleotide sequence other than the polynucleotide sequence included in the linker molecule.

If a probe includes a polynucleotide, the polynucleotide can include any suitable number of nucleotides. In one embodiment, a probe includes at least about 10 nucleotides. In another embodiment, a probe includes from about 10 to about 45 nucleotides. In yet another embodiment, a probe includes at least about 30 nucleotides. Different probes that include a polynucleotide can include either the same number of nucleotides or a different number of nucleotides.

As used herein, "linker molecule" refers to one or more molecules that are configured to mediate the association of a tag with a probe. Generally, the linker molecule is bifunctional in that it includes a functionality for linking to a tag and a functionality for linking to a probe. A "linker molecule" is a set of copies of one type or species of molecule(s) or multimolecular structure(s) that is capable of associating a tag with a probe. "Linker molecules" refers to more than one such set of molecules or multi-molecular structures. A linker molecule may have any suitable configuration and can include any suitable components, including a polynucleotide, a polypeptide, a peptide nucleic acid, a locked nucleic acid, an oligosaccharide, a polysaccharide, an antibody, an affybody, an antibody mimic, a polyethylene glycol (PEG) molecule, a cell receptor, a ligand, a lipid, any fragment or derivative of these structures, any combination of the foregoing, or any other structure or chemical component that can be designed or configured to mediate an association between a tag and a probe with specificity. A linker molecule may be aliphatic or aromatic.

The composition of the linker molecule is not critical to any of the methods disclosed herein. It is often preferred that the linker molecule be hydrophilic. As a general rule, the length of a particular linker molecule can be selected to provide for convenience of synthesis and ease in mediating the association of a tag with a probe. The linker molecule should not contain functionalities, or be of a length, that will interfere with the reactions that are desired in accordance with the disclosed methods.

With reference to FIGS. 2A, 2B, and 2C, when a linker molecule is employed in any of the methods disclosed herein, the linker molecule may be introduced at any suitable time during the performance of the assay and may first contact either a tag or a probe. For example, a tag included on an aptamer may be contacted with the linker molecule any time before an aptamer covalent complex contacts the probe on a solid support. In another embodiment, a probe attached to a solid support may be contacted with a linker molecule any time before the probe is exposed to the tag on an aptamer covalent complex. In a further embodiment, depending upon the complexity of the particular assay performed and the reaction conditions, for example, a probe may be contacted with both a linker molecule and a tag on an aptamer covalent complex simultaneously.

A linker molecule generally comprises a tag association component and a probe association component. The tag association component and probe association component are independently selected based upon the particular tag and probe utilized in a particular assay. In one embodiment, the tag association component is a polynucleotide that is complementary to a polynucleotide sequence included in a tag. In another embodiment, the probe association component is a polynucleotide that is complementary to a polynucleotide sequence included in a probe. In a further embodiment, the tag association component is a polynucleotide and the probe association component is also a polynucleotide.

In a further embodiment, the linker molecule includes a tag association component separated from a probe association component by a third component. In this embodiment, the third component can include one or more molecules or sub-components, including a polynucleotide, a polypeptide, a peptide nucleic acid, a locked nucleic acid, an oligosaccharide, a polysaccharide, an antibody, an affybody, an antibody mimic, an aliphatic carbon molecule, a polyethylene glycol (PEG) molecule, a cell receptor, a ligand, a lipid, any fragment or derivative of these structures, any combination of the foregoing, or any other chemical structure or component that can aid in the association of the tag with the probe, such as, e.g., by increasing flexibility between the tag association component and the probe association component.

A polynucleotide component of a linker molecule can include any suitable number of nucleotides. In one embodiment, a polynucleotide component of a linker molecule includes at least about 10 nucleotides. In another embodiment, a polynucleotide component of a linker molecule includes from about 10 to about 45 nucleotides. In yet another embodiment, a polynucleotide component of a linker molecule includes at least about 30 nucleotides. Linker molecules used in any of the methods disclosed herein can include polynucleotide components having either the same number of nucleotides or a different number of nucleotides.

As used herein, "photoaptamer," "photoreactive nucleic acid ligand," and "photoreactive aptamer" are used interchangeably to refer to an aptamer that contains one or more photoreactive functional groups that can covalently bind to or "crosslink" with a target molecule. For example, a naturally occurring nucleic acid residue may be modified to include a chemical functional group that confers photoreactivity upon the nucleic acid residue upon exposure to a radiation source of an appropriate wavelength. A photoaptamer can be identified and/or prepared using any known method. In some embodiments, a photoreactive aptamer is identified using the photoSELEX process. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands." In other embodiments, an aptamer is prepared and is subsequently modified to incorporate one or more photoreactive functional groups, thereby generating a photoaptamer. In these embodiments, one or more photoreactive nucleic acid residues can be incorporated into an aptamer either by substituting a photoreactive nucleic acid residue in the place of one or more other nucleotides, such as one or more of the thymidine and/or cytidine nucleotides in the aptamer, for example, or by modifying one or more nucleic acid residues to include a photoreactive functional group.

Exemplary photoreactive functional groups that may be incorporated into a photoaptamer include 5-bromouracil, 5-iodouracil, 5-bromovinyluracil, 5-iodovinyluracil, 5-azidouracil, 4-thiouracil, 5-thiouracil, 4-thiocytosine, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-aziodoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

In addition to these exemplary nucleoside-based photoreactive functional groups, other photoreactive functional groups that can be added to a terminal end of an aptamer using an appropriate linker molecule can also be used. Such photoreactive functional groups include benzophenone, anthraquinone, 4-azido-2-nitro-aniline, psoralen, derivatives of any of these, and the like.

A photoreactive functional group incorporated into a photoaptamer may be activated by any suitable method. In one embodiment, a photoaptamer containing a photoreactive functional group is crosslinked to its target by exposing the photoaptamer affinity complex to a source of electromagnetic radiation. Suitable types of electromagnetic radiation include ultraviolet light, visible light, X-rays, and gamma rays. Suitable radiation sources include sources that utilize either monochromatic light or filtered polychromatic light.

In one embodiment, a photoreactive nucleotide, such as 4-azido-2-nitro-aniline, for example, can be incorporated into a photoaptamer, and light having a wavelength ranging from about 325 nm to about 470 nm may be used to irradiate a photoaptamer affinity complex that includes this photoaptamer. Excitation at these wavelengths can be accomplished, for example, with inexpensive light emitting diodes (LEDs) using either a single LED or an array of LEDs, since the power requirements are modest. Nearly monochromatic light having a wavelength ranging from 465 to 475 nm, a 100 degree viewing angle and providing 38 lumens of light is supplied by one or more high-powered LEDs. In the event that a desired photoreactive functional group cannot be excited at a wavelength produced by an LED, appropriate substitution of electron withdrawing or electron donating groups often can be used to modestly shift the excitation wavelength of the photoreactive functional group to enable excitation of the photoreactive functional group at a wavelength produced by an LED.

In one embodiment, a photoreactive nucleotide is incorporated into a photoaptamer, and light having a wavelength ranging from about 300 nm to about 350 nm may be used to irradiate a photoaptamer affinity complex that includes this photoaptamer to convert the photoaptamer affinity complex to a photoaptamer covalent complex.

In one embodiment, a photoreactive nucleotide, such as a 5-iodouracil or a 5-iodocytosine, for example, can be incorporated into a photoaptamer, and light having a wavelength ranging from about 320 nm to about 325 nm may be used to irradiate a photoaptamer affinity complex that includes this photoaptamer. This combination facilitates selective photocrosslinking of the chromophore-containing photoaptamer to the target molecule without inducing other, non-specific photoreactions. For example, in the case of target protein, any tryptophan residues that might be included in the target protein and any thymine and uracil bases that might be included in the photoaptamer may also be photoreactive. Since 5-iodouracil or 5-iodocytosine absorbs light having a wavelength of about 325 nm but tryptophan and naturally occurring nucleic acid bases do not, using light of this wavelength permits a selective photoreaction at the 5-iodouracil(s) or 5-iodocytosine(s) within the photoaptamer affinity complex. Monochromatic light having a wavelength ranging from about 320 nm to about 325 nm may be supplied, for example, by a frequency doubled tunable dye laser emitting light at a wavelength of about 320 nm or by a helium cadmium laser emitting light at a wavelength of about 325 nm.

In a further embodiment, a photoaptamer affinity complex can be exposed to a xenon chloride (XeCl) excimer laser set to emit light at a wavelength of about 308 nm. In this embodiment, the photoaptamer can include a photoreactive functional group (e.g., a 5-bromouracil or a 5-bromocytosine), and treating the photoaptamer affinity complex with the light source serves to photoactivate the photoreactive functional group such that the photoaptamer crosslinks with its target molecule and a photoaptamer covalent complex is formed.

In yet another embodiment, a photoaptamer can be crosslinked to its target by exposing a photoaptamer affinity complex to a high-pressure mercury lamp set to emit light at a wavelength of about 313 nm. In further embodiments, wavelength filters may be employed to restrict the emitted light to be greater than about 300 nm to minimize activation of chromophores other than those included in a photoaptamer affinity complex.

In a further embodiment, a photoaptamer can be crosslinked to its target by exposing a photoaptamer affinity complex to a low pressure mercury lamp set to emit light at a wavelength of about 254 nm, which is then absorbed by a phosphor and re-emitted at a wavelength ranging from about 300 nm to about 325 nm. In this embodiment, the re-emitted light is filtered to remove any light of about 254 nm that is not absorbed by the phosphor as well as any light of wavelengths ranging from about 290 nm to about 305 nm, which may be damaging to a target protein.

In still another embodiment, a halogen photoreactive functional group, such as an iodouracil or a bromocytosine for example, can be incorporated into a photoaptamer, and a photoaptamer affinity complex that includes this photoaptamer can be treated with light having a wavelength ranging from about 350 nm to about 400 nm. For example, monochromatic light from the third harmonic of a Neodymium YAG laser set at about 355 nm or monochromatic light from the first harmonic of a xenon fluoride (XeF) excimer laser at about 351 nm may be used.

As used herein, "target molecule" and "target" are used interchangeably to refer to any molecule of interest to which an aptamer can bind with high affinity and specificity and that may be present in a test sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component that does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. An aptamer may be identified for virtually any chemical or biological molecule of any size, and thus virtually any chemical or biological molecule of any size can be a suitable target. A target can also be modified to enhance the likelihood or strength of an interaction between the target and the aptamer. In exemplary embodiments, the target molecule is a protein. See U.S. Pat. No. 6,376,190 entitled "Modified SELEX Processes Without Purified Protein" for methods in which the SELEX target is a peptide.

"Polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains.

As used herein, "non-target molecule" and "non-target" are used interchangeably to refer to a molecule contained in a test sample that can form a non-specific complex with an aptamer. A "non-target molecule" or "non-target" is a set of copies of one type or species of molecule or multi-molecular structure that is capable of binding to an aptamer. "Non-target molecules" or "non-targets" refers to more than one such set of molecules. It will be appreciated that a molecule that is a non-target for a first aptamer may be a target for a second aptamer. Likewise, a molecule that is a target for the first aptamer may be a non-target for the second aptamer.

As used herein, the term "aptamer affinity complex" refers to a non-covalent complex that is formed by the interaction of an aptamer with its target molecule. An "aptamer affinity complex" is a set of copies of one type or species of complex formed by an aptamer bound to its corresponding target molecule. "Aptamer affinity complexes" refers to more than one such set of complexes. An aptamer affinity complex can generally be reversed or dissociated by a change in an environmental condition, e.g., an increase in temperature, an increase in salt concentration, or an addition of a denaturant.

As used herein, the term "aptamer covalent complex" refers to an aptamer affinity complex in which the aptamer has been induced to form or otherwise forms a covalent bond with its target molecule. An "aptamer covalent complex" is a set of copies of one type or species of complex formed by an aptamer covalently bound to its corresponding target molecule. "Aptamer covalent complexes" refers to more than one such set of complexes. A covalent bond or linkage between an aptamer and its target molecule can be induced by photoactivation of a chemical moiety on the aptamer, including those moieties described above with respect to photoaptamers. A covalent bond or linkage between an aptamer and its target molecule can also be induced chemically. Chemical groups that can be included in an aptamer and used to induce a covalent linkage with the target include but are not limited to aldehydes, maleimides, acrylyl derivatives, diazonium derivatives, thiols, etc. In some embodiments, chemical crosslinking groups, such as maleimide or diazonium salts, for example, can convert aptamer affinity complexes to aptamer covalent complexes simply by providing the proper environment and juxtaposition of reactive groups required for specific and sufficiently enhanced chemical reactivity to occur. In other embodiments, chemical crosslinkers, such as aldehyde groups, may require the addition of another component, for example, sodium cyanoborohydride, to convert aptamer affinity complexes to stable, irreversible aptamer covalent complexes. In yet other embodiments, no such chemical crosslinkers are included in an aptamer; rather, a third reagent is used to convert an aptamer affinity complex to an aptamer covalent complex by facilitating a covalent attachment between the aptamer and its target. For example, a homo- or hetero-bifunctional reagent containing both an amine reactive moiety (e.g., an N-hydroxy succinimidyl ester, an aldehyde, or an imidate) and a nucleoside-reactive group (e.g., an iodoacetamide or an activated aldehyde) can induce covalent complexation of an aptamer affinity complex, such as an affinity complex formed by an aptamer and a target protein.

The term "test sample" refers herein to any material, solution, or mixture that contains a plurality of molecules and may include at least one target molecule. The term test sample includes biological samples, as defined below, and samples that may be used for environmental or toxicology testing, such as contaminated or potentially contaminated water and industrial effluents, for example. A test sample may also be an end product, intermediate product, or by-product of a preparatory process, for example a manufacturing process. A test sample may include any suitable assay medium, buffer, or diluent that has been added to a material, solution, or mixture obtained from an organism or from some other source (e.g., the environment or an industrial source).

The term "biological sample" refers to any material, solution, or mixture obtained from an organism. This includes blood (including whole blood, leukocytes, peripheral blood mononuclear cells, plasma, and serum), sputum, breath, urine, semen, saliva, meningeal fluid, amniotic fluid, glandular fluid, lymph fluid, nipple aspirate, bronchial aspirate, synovial fluid, joint aspirate, cells, a cellular extract, and cerebrospinal fluid. This also includes experimentally separated fractions of all of the preceding. The term "biological sample" also includes materials, solutions, or mixtures containing homogenized solid material, such as from a stool sample, a tissue sample, or a tissue biopsy, for example. The term "biological sample" also includes materials, solutions, or mixtures derived from a tissue culture, cell culture, bacterial culture, or viral culture.

"Solid support" refers to any substrate having a surface to which molecules may be attached, directly or indirectly, through either covalent or non-covalent bonds. The solid support may include any substrate material that is capable of providing physical support for the probes that are attached to the surface. The material is generally capable of enduring conditions related to the attachment of the probes to the surface and any subsequent treatment, handling, or processing encountered during the performance of an assay. The materials may be naturally occurring, synthetic, or a modification of a naturally occurring material. Suitable solid support materials may include silicon, graphite, mirrored surfaces, laminates, ceramics, plastics (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly (ethylene terephthalate), polytetrafluoroethylene (PTFE or Teflon®), nylon, poly(vinyl butyrate)), germanium, gallium arsenide, gold, silver, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, including bead, tube, well, and the like. Usually, the material is relatively planar such as, for example, a slide, though it can be spherical, such as, for example, a bead, or cylindrical (e.g., a column). In many embodiments, the material is shaped generally as a rectangular solid. Multiple predetermined arrangements such as, e.g., arrays of probes, may be synthesized on a sheet, which is then diced, i.e., cut by breaking along score lines, into single array substrates. Exemplary solid supports that may be used include microtitre wells, microscope slides, membranes, paramagnetic beads, charged paper, Langmuir-Blodgett films, silicon wafer chips, flow through chips, and microbeads.

The surface of the solid support is usually the outer portion of the substrate material that forms the solid support. The surface of the solid support onto which the probes are bound may be smooth or substantially planar, or have irregularities, such as depressions, grooves, elevations, or other textures. The surface may be modified with one or more different layers of compounds that serve to modify the properties of the surface in a desirable manner. In various embodiments, such surface modification layers, when present, can generally range in thickness from a monomolecular thickness to about 1 mm, or from a monomolecular thickness to about 0.1 mm, or from a monomolecular thickness to about 0.001 mm.

Surface modification layers of interest include inorganic and organic layers, such as metals, metal oxides, polymers, small organic molecules, and the like. Polymeric layers of interest include methacrylate copolymers, polyacrylamides, polysaccharides, phospholipids, polyurethanes, polyesters, polycarbonates, polyureas, polyamides, polyethylene amines, polyarylene sulfides, polysiloxanes, polyimides, polyacetates, and the like, where the polymers may be hetero- or homo-polymeric, and may or may not have separate functional moieties attached thereto (for example, conjugated moieties). Other surface modifications of interest include three-dimensional networks, such as hydrogels, for example. Any suitable hydrogel known in the art may be used. See, e.g., U.S. Patent Application Publication No. 2003/0218130 entitled "Biochips with Surfaces Coated with Polysaccharide-Based Hydrogels," U.S. Patent Application Publication No. 20050147994 entitled "Method for Immobilizing a Biologic in a Polyurethane-Hydrogel Composition, a Composition Prepared from the Method, and Biomedical Applications," U.S. Patent Application Publication No. 2005005908 entitled "Photocrosslinked Hydrogel Blend Surface Coatings," and any of the references cited in these publications.

In one embodiment, the surface of a solid support includes a hydrogel. The hydrogel can comprise, for example, a polymer matrix. The hydrogel can be chemically attached to the surface of the solid support and can include a binding functionality that is capable of attaching, either directly or indirectly, a probe to the hydrogel. Exemplary binding functionalities include a hydrophobic group, a hydrophilic group, reactive groups such as aldehydes, epoxy, carbonates and the like, a carboxyl, a thiol, a sulfonate, a sulfate, an amino, a substituted amino, a phosphate, a metal chelating group, a thioether, a biotin, a boronate, etc.

Any surface suitable for gene expression or SNP analysis may also be used, including substrates and surfaces offered, for example, by Affymetrix, General Electric (e.g., CodeLink), Agilent, and Schott Nexterion, either as substrates and surfaces or as components of products that further comprise other components.

A probe can be bound to the surface of the solid support in any suitable manner, so long as the probe will not become unbound during subsequent incubation and processing steps in accordance with the disclosed methods, such as washing the surface to remove non-specific complexes, for example. The probe may be bound by being non-covalently linked, e.g., adhered, absorbed, adsorbed, or by being covalently linked to the surface of the solid support. In the case of a covalent linkage of the probe to the solid support, the surface of the solid support will contain a functional group that links to the probe. The nature of the functional group(s) used is dependent upon the nature of the probe. A variety of methods have been reported for the covalent attachment of molecules to a surface. Typically, these reactions are performed by the reaction of an active functional group on a molecule with an activated functional group on the surface. As an example, an amine-containing compound can be attached to a carboxylic acid containing surface by forming an activated ester of the carboxylic acid, such as an N-hydroxysuccinimide derivative. The amine readily reacts with this activated ester to form a stable amide bond. This reaction is useful under conditions whereby the reaction with the desired amine is significantly faster than with other nucleophiles in the system.

Examples of methods that have been previously described in the art include the activation of surfaces with cyanogen bromide, N-hydroxysuccinimide esters, carbonyl diimidazole, carbodiimides, azlactones, cyanuric chlorides, organic sulfonyl chlorides, divinyl sulphone, nitrophenyl esters, iodoacetyl, maleimide, epoxy, hydrazide, reductive amination, diazonium salts, and Mannich condensations. Molecules that react with the activated surface include amines, alcohols, carboxylic acids, thiols, carbonyls, and compounds containing active hydrogens.

In one embodiment, the probes are bound to the surface of the solid support in a predetermined, spatial arrangement or pattern, which means any arrangement on the surface where the identity of a probe at a particular location is known. In one embodiment, the predetermined arrangement is an array. An array generally includes any one-, two-, or three-dimensional arrangement of addressable regions bearing a particular probe associated with that region. An array is addressable in that it has multiple regions of different probes, such that a region or feature or spot of the array at a particular predetermined location or address on the array detects a particular aptamer covalent complex, and therefore a particular target molecule, by virtue of associating specifically with the tag on such aptamer covalent complex.

An array assembly on the surface of a solid support refers to one or more arrays disposed along a surface of an individual solid support and separated by inter-array areas. Normally, the surface of the solid support opposite the surface with the arrays (opposing surface) does not carry any arrays. The arrays can be designed for testing against any type of test sample. The surface of the solid support may carry at least one, two, four, twenty, a hundred, or at least five hundred arrays. Depending upon intended use, any or all of the arrays may be the same or different from one another and each may contain multiple spots or features of probes disposed thereon. A typical array may contain more than ten, more than one hundred, more than one thousand, or ten thousand features, or even more than one hundred thousand features, in an area of less than about 20 $cm^2$ or even less than about 10 $cm^2$. For example, features may have widths (that is, diameter, for a round spot) in the range from about 10 μm to about 1.0 cm. In other embodiments, each feature may have a width in the range of about 1.0 μm to about 1.0 mm, or from about 5.0 μm to about 500 μm, or from about 10 μm to about 200 μm. Non-round features may have area ranges equivalent to that of circular features with the foregoing width (diameter) ranges.

Any of a variety of geometries of arrays on a solid support may be used. As mentioned above, an individual solid support may contain a single array or multiple arrays. Features of the array may be arranged in rectilinear rows and columns. This is particularly attractive for single arrays on a solid support. When multiple arrays are present, such arrays can be arranged, for example, in a sequence of curvilinear rows across the surface of the solid support (for instance, a sequence of concentric circles or semi-circles of spots), and the like. Similarly, the pattern of features may be varied from the rectilinear rows and columns of spots to include, for example, a sequence of curvilinear rows across the surface of the solid support (for example, a sequence of concentric circles or semi-circles of spots), and the like. The configuration of the arrays and their features may be selected according to manufacturing, handling, and use considerations.

Each feature, or element, within the array is defined to be a small, regularly shaped region of the surface of the solid support. The features are arranged in a predetermined manner. Each feature of an array usually carries a predetermined probe or mixture of probes. Each feature within the molecular array may contain a different probe, and the probe within a given feature may differ from the probes within the remaining features of the array. Some or all of the features may be of different compositions. Each array may contain multiple spots or features, and each array may be separated from another array by spaces or areas. It will also be appreciated that there need not be any space separating arrays from one another. Interarray areas and interfeature areas are usually present but are not essential. As with any border areas, these interarray and interfeature areas do not carry any probes. It will be appreciated that the interarray areas and interfeature areas, when present, could be of various sizes and configurations.

In some embodiments, an array may be formed by attaching a probe to a first solid support, such as a bead, for example, and then arranging the first solid support in an array format on a second solid support, such as a microtiter plate, for example. In other embodiments, an array may be formed by attaching probes to addressable beads. "Addressable beads" include dyes, barcodes, and transponders.

In some embodiments, depending upon the selected surface of the solid support, the surface may be "blocked" or "passivated" in order to reduce or inhibit non-specific binding of molecules to the surface of the solid support. Blocking or passivation reagents include dry milk, casein, pooled serum, pooled plasma, BSA, PEG-PLL, PEG-silane, SuperBlock or StarterBlock (Pierce Biotechnology, Rockford, Ill.), and any combination of any of the foregoing.

As used herein, the term "labeling agent" refers to one or more reagents that can be used to detect a target molecule that is bound to an aptamer in an aptamer covalent complex.

In one embodiment for detecting a target molecule, an aptamer covalent complex is contacted with a labeling agent that includes a binding partner that is specific for the target molecule bound to the aptamer. The specific binding partner may be any suitable moiety, including an antibody, an antibody fragment, a synthetic antibody mimetic, a biomimetic, an aptamer, a molecular imprinted ligand, and the like. The specific binding partner is conjugated or linked to another labeling agent component, usually, a detectable moiety or label. The linking of the specific binding partner to the label may be carried out by any of the aforementioned methods for linking a probe to the surface of the solid support. It will be appreciated that in the case of detecting multiple target molecules, multiple aptamer covalent complexes can be contacted with a mixture of specific binding partners, each specific for a target molecule suspected of being present. The labels employed may be those that are known in the art for multiplexed detection of multiple target molecules.

The detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

In another embodiment for detecting a target molecule, the target molecule is a protein, and the aptamer covalent complex is contacted with a labeling agent that comprises a universal protein stain. As used herein, "universal protein stain" and "UPS" are used interchangeably to refer to any labeling agent that labels most, if not all, proteins present in a test sample with a detectable moiety but tends not to label, or labels only minimally, nucleic acids or other components of the assay, such as the solid support. Any reactive chemical group found on proteins, but not found on nucleic acids or the substrate surface, can serve as a site of covalent attachment. Exemplary reactive chemical groups include primary amines (e.g., on lysine residues), thiols (e.g., on cysteine, which may be produced by the reduction of disulfide linkages), alcohols (e.g., on serine, threonine, tyrosine, and sugar moieties on glycoproteins (including the products of oxidation of cis-diols on such sugars)), and carboxylates (e.g., on glutamic and aspartic acid).

The detectable moiety can include any of the reporter molecules listed above and any other chemical or component that may be used in any manner to generate a detectable signal. The detectable moiety may be detected via a fluorescent signal, a chemiluminescent signal, or any other detectable signal that is dependent upon the identity of the moiety. In the case where the detectable moiety is an enzyme (for example, alkaline phosphatase), the signal may be generated in the presence of the enzyme substrate and any additional factors necessary for enzyme activity. In the case where the detectable moiety is an enzyme substrate, the signal may be generated in the presence of the enzyme and any additional factors necessary for enzyme activity. Suitable reagent configurations for attaching the detectable moiety to a target protein include covalent attachment of the detectable moiety to the target protein, non-covalent association of the detectable moiety with another labeling agent component that is covalently attached to the target protein, and covalent attachment of the detectable moiety to a labeling agent component that is non-covalently associated with the target protein. Universal protein stains are described in detail in U.S. patent application Ser. No. 10/504,696, filed Aug. 12, 2004, entitled "Methods and Reagents for Detecting Target Binding by Nucleic Acid Ligands."

In some embodiments, the UPS is a single chemical reagent that comprises a detectable moiety and reacts covalently with a functional group that is characteristic of proteins, but not aptamers, and, in so reacting, covalently attaches the detectable moiety to a target protein. UPSs according to this embodiment include dyes with groups capable of reacting covalently with functional groups that are unique to proteins. Such groups may be added to the dyes by derivatization or may be present on the unmodified dye. In one embodiment, the UPS comprises an N-hydroxysuccinimide-activated dye that reacts with amine groups, such as an N-hydroxysuccinimide-activated fluorophore, including NHS-Alexa fluorophores (such as, e.g., NHS-Alexa 647). Another UPS that may be used is CBQCA (3-(4-carboxybenzoyl)quinoline-2-carboxaldehyde), which also reacts with amines in the presence of cyanide or thiols to form highly fluorescent isoindoles. Other amine reactive groups suitable for use in UPS reagents include isocyanates, isothiocyanates, acyl azides, sulfonyl chlorides, aldehydes, 4-sulfo-2,3,5,6-tetrafluorophenol (STP) esters, TFP-Alexa 647, and arylating agents such as NBD (7-nitrobenz-2-oxa-1,3-diazole) chloride, NBD fluoride, and dichlorotriazines.

In other embodiments, the UPS comprises a plurality of reagents. For example, the UPS can comprise a first reagent that reacts covalently with a target protein, and one or more further reagents that attach the detectable moiety, either directly or indirectly, and either covalently or non-covalently, to the target protein via a chemical group or other functionality introduced by the first reagent. Where the UPS comprises multiple reagents, it will be appreciated that in some cases the reagents are added sequentially, and in other cases they may be added simultaneously.

In one embodiment, a suitable UPS comprises (a) a biotin derivative that reacts with a target protein; and (b) a streptavidin-detectable moiety conjugate, such as, for example, a fluorescent streptavidin derivative or a streptavidin-enzyme conjugate. The biotin derivative reacts with amine groups, thereby covalently attaching biotin to the target protein; the streptavidin-detectable moiety conjugate binds to the immobilized biotin groups, thereby localizing the detectable moiety to site(s) on the solid support to which the target protein is bound. In this embodiment, suitable reagents include PFP-biotin, NHS-PEO$_4$-biotin (spacer arm 29 Å), Sulfo-NHS-LC-biotin (spacer arm 22.4 Å), and TFP-PEO$_3$-biotin (spacer arm 32.6 Å).

In another embodiment, a suitable UPS comprises: (a) biotin, or a biotin derivative, conjugated to a reactive group that is capable of covalently attaching the biotin or biotin derivative to a bound target protein; (b) avidin and/or streptavidin; and (c) a biotin-detectable moiety conjugate, such as, for example, a fluorescent biotin derivative. The biotin derivative in (a) above may be an amine-reactive biotin derivative, such as, for example, NHS-Biotin, wherein the biotin is optionally separated from the NHS by spacer atoms (Calbiochem, Inc.). Reaction of the NHS group with primary amines on the bound target protein leads to the covalent attachment of biotin to the target protein that is bound to its corresponding aptamer. The target protein complexed with its corresponding aptamer can then be treated with the streptavidin or avidin. Since streptavidin and avidin can each bind four biotins, the addition of these proteins provides three biotin binding sites for each biotin originally coupled to the bound target protein by the NHS-biotin. The biotin-detectable moiety derivative of (c) above can then be added, whereupon it binds tightly to the unoccupied biotin binding sites on the streptavidin or avidin. In this embodiment, suitable reagents include PFP-biotin, NHS-PEO$_4$-biotin (spacer arm 29 Å), Sulfo-NHS-LC-biotin (spacer arm 22.4 Å), and TFP-PEO$_3$-biotin (spacer arm 32.6 Å).

Considerations such as the nature of the labeling agent, the nature of, and predetermined cut-off levels for, the target molecules, the biological significance of specific target levels, and so forth normally determine the concentration of the labeling agent, including the individual concentrations of the particular reagents that may be used. The final concentration of each of the reagents will normally be determined empirically to optimize the sensitivity of the method. In one embodiment, the concentration of the labeling agent is usually sufficient to detect at least about 1% of the target molecules. In another embodiment, the concentration of the labeling agent is usually sufficient to detect at least about 10% of the target molecules. In a further embodiment, the concentration of the labeling agent is usually sufficient to detect at least about 90% of the target molecules.

Activation of the labeling agent depends upon the nature of the reagents used. For example, for those reagents that are activated with light, the reagent is irradiated with light of an appropriate wavelength. Other activation methods will be suggested to those skilled in the art in view of the disclosures herein. For some labeling agents, such as labeling agents that involve a radioactive label, an enzyme, and so forth, no activation agent is necessary. For enzyme systems, the addition of a substrate and/or a cofactor may be necessary.

The examination of the solid support for the presence and/or amount of the signal generated by the labeling agent includes the detection of the signal, which is generally merely a step in which the signal is read. The signal is normally read using an instrument, the nature of which depends upon the nature of the signal. The instrument may be a spectrophotometer, fluorometer, an absorption spectrometer, luminometer, chemiluminometer, actinometer, photographic instrument, and the like. The presence and/or amount of signal detected is related to the presence and amount of any target molecule present in a test sample above a predetermined cut-off level. Temperatures during measurements generally can range from about 10° to about 70° C., or from about 20° to about 45° C., or from about 20° to about 25° C. In one approach, standard curves are formed using known concentrations of the target molecules being tested. Calibrators and other controls may also be used.

In one embodiment, a solid support, including an array, for example, is moved to an examining device where the surface of the solid support is interrogated for the presence of any bound target molecules. The examining device may be a scanning device involving an optical system. The array can be examined or read, for example, by illuminating the array and reading the location and intensity of a resulting signal (e.g., fluorescence) at each feature of the array. The scanner may be similar to, for example, the TECAN LS 300 scanner available from Tecan Systems, San Jose, Calif. However, arrays may be examined or read by using methods or an apparatus other than the foregoing, with other methods of examining an array including other optical techniques (for example, detecting chemiluminescent or electroluminescent labels) and electrical techniques.

Results generated from an examination of the array may be raw results (such as fluorescence intensity readings for each feature in one or more color channels) or may be processed results, such as results obtained by rejecting a reading for a feature that is below a predetermined threshold and/or forming conclusions based upon the pattern read from the array (such as whether or not a particular target molecule may have been present in the test sample). The results of the examination (processed or not) may be forwarded (such as by communication) to a remote location, if desired, and received there for further use (such as further processing).

In another embodiment, the method is carried out under the control of a computer, that is, with the aid of a computer. For example, an IBM® compatible personal computer may be utilized. The computer is driven by software specific to the methods described herein. Computer hardware capable of assisting in the performance of the methods disclosed herein can involve a system having the following specifications: Pentium® processor or better with a clock speed of at least 100 MHz, at least 32 megabytes of random access memory (RAM), and at least 80 megabytes of virtual memory, running under either the Microsoft Windows® 95 or Microsoft Windows NT® 4.0 operating system (or successor thereof), for example.

Software that may be used to carry out the methods may be, for example, Microsoft Excel or Microsoft Access®, suitably extended via user-written functions and templates, and linked when necessary to stand-alone programs that may be desired. Examples of software or computer programs used in assisting in conducting the present methods may be written in Visual BASIC®, FORTRAN, C, C++, Java, Python, or any other suitable programming language available now or in the future. It should be understood that the above computer information and the software used herein are exemplary only and not intended to be restrictive. Any of the methods disclosed herein may be adapted to other computers, computer systems, and software. Other languages that may be used include, for example, PASCAL, PERL or assembly language.

In another embodiment, the aptamer affinity complex (or optional aptamer covalent complex) is detected and/or quantified using mass spectrometry. With reference to FIG. 1B, in an exemplary method for the detection and/or quantification of a target molecule that may be present in a test sample, a test sample is contacted with an aptamer that includes a tag and has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted, using a method appropriate to the aptamer being employed, to an aptamer covalent complex that includes an aptamer covalently bound to its target molecule. The aptamer affinity complex (or optional aptamer covalent complex) is attached to a solid support. The attachment is accomplished by contacting the solid support with the aptamer affinity complex (or optional aptamer covalent complex) and allowing the tag included on the aptamer to associate, either directly or indirectly, with a probe that is attached to the solid support. The aptamer affinity complex (or optional aptamer covalent complex) that has associated with the probe on the solid support is then prepared for detection (and optional quantification) using mass spectrometry.

The aptamer affinity complex (or optional aptamer covalent complex) may be prepared for detection and optional quantification by mass spectrometry using any of a variety of methods. For example, in one embodiment, when the target molecule is a protein, the aptamer affinity complex (or optional aptamer covalent complex) is prepared by protease digestion either before or after removing the complex from the solid support. In another embodiment, the aptamer affinity complex (or optional aptamer covalent complex) is released from the solid support and then prepared for mass spectrometric analysis using any of a number of methods known in the art, including matrix-assisted laser desorption ionization (MALDI), surface enhanced laser desorption ionization (SELDI), electrospray ionization, or electron impact ionization. In one embodiment, the aptamer affinity complex (or optional aptamer covalent complex) can be directly eluted into an electrospray ionization mass spectrometer. In other embodiments, the eluted test sample may be subjected to further processing, such as, for example, enzymatic digestion or chemical modification, prior to mass spectrometric analysis. The mass spectra can be obtained by, for example, electrospray ionization, matrix-assisted laser desorption ionization, or electron-impact ionization.

Typically, quantification of a target molecule by mass spectrometry requires an internal standard, that is, a compound of known concentration that is introduced into the test sample that is to be analyzed. Ideal internal standards will have elution and ionization characteristics similar to those of the target molecule but will generate ions with different mass-to-charge ratios. A common internal standard is a stable isotope-labeled version of the target molecule. In one embodiment, a stable isotope-labeled version of the target molecule is added to the test sample as an internal standard. Spectral peaks corresponding to the various components in the test sample are then compared with the internal standard's peak height or area and thereby enable quantification of the target molecule.

In another embodiment, quantification of the target molecule is accomplished by comparing the peak height or area of the spectral peaks corresponding to the target molecule with those spectral peaks generated from a set of samples with known concentrations of the target molecule. The peak heights or areas of the spectral peaks obtained from the samples having known concentrations of the target molecule constitute a standard curve from which the unknown concentration of the target molecule in the test sample can be computed.

In another embodiment, the aptamer affinity complex (or optional aptamer covalent complex) is detected and/or quantified using Q-PCR. As used herein, "Q-PCR" refers to a PCR reaction performed in such a way and under such controlled conditions that the results of the assay are quantitative, that is, the assay is capable of quantifying the amount or concentration of aptamer present in the test sample. With reference to FIG. 1B, in an exemplary method for the detection and/or quantification of a target molecule that may be present in a test sample, a test sample is contacted with an aptamer that may include a tag and has a specific affinity for a target molecule. An aptamer affinity complex that includes an aptamer bound to its target molecule is allowed to form. If the test sample contains the target molecule, an aptamer affinity complex will generally form in the test sample. The aptamer affinity complex is optionally converted, using a method appropriate to the aptamer being employed, to an aptamer covalent complex that includes an aptamer covalently bound to its target molecule. As further described herein, following the formation of an aptamer affinity complex and any optional conversion to an aptamer covalent complex, any free aptamer that may be present in the test sample is then partitioned from the aptamer affinity complex (or optional aptamer covalent complex). The aptamer affinity complex (or optional aptamer covalent complex) is then quantified using known techniques for the quantitative replication of polynucleotides.

In one embodiment, the amount or concentration of the aptamer affinity complex (or optional aptamer covalent complex) in the test sample is determined using TaqMan® PCR. This technique generally relies on the 5'-3' exonuclease activity of the oligonucleotide replicating enzyme to generate a signal from a targeted sequence. A TaqMan probe is selected based upon the sequence of the aptamer to be quantified and generally includes a 5'-end fluor, such as 6-carboxyfluorescein, for example, and a 3'-end quencher, such as, for example, a 6-carboxytetramethylfluorescein, to generate signal as the aptamer sequence is amplified using polymerase chain reaction (PCR). As the polymerase copies the aptamer sequence, the exonuclease activity frees the fluor from the probe, which is annealed downstream from the PCR primers, thereby generating signal. The signal increases as replicative product is produced. The amount of PCR product depends upon both the number of replicative cycles performed as well as the starting concentration of the aptamer.

In another embodiment, the amount or concentration of an aptamer affinity complex (or optional aptamer covalent complex) is determined using an intercalating fluorescent dye during the replicative process. The intercalating dye, such as, for example, SYBR® green, generates a large fluorescent signal in the presence of double-stranded DNA as compared to the fluorescent signal generated in the presence of single-stranded DNA. As the double-stranded DNA product is formed during PCR, the signal produced by the dye increases. The magnitude of the signal produced is dependent upon both the number of PCR cycles and the starting concentration of the aptamer.

In another embodiment, the amount or concentration of the aptamer affinity complex (or optional aptamer covalent complex) is determined using a "molecular beacon" during the replicative process (see, e.g., Tyagi et al., Nat. Biotech. 16:49 53, 1998; U.S. Pat. No. 5,925,517). A molecular beacon is a specific nucleic acid probe that folds into a hairpin loop and contains a fluor on one end and a quencher on the other end of the hairpin structure such that little or no signal is generated by the fluor when the hairpin is formed. The loop sequence is specific for a target polynucleotide sequence and, upon hybridizing to the aptamer sequence the hairpin unfolds and thereby generates a fluorescent signal.

A computer program may be utilized to carry out one or more steps of any of the methods disclosed herein. Another aspect of the present invention is a computer program product comprising a computer readable storage medium having a computer program stored thereon which, when loaded into a computer, performs or assists in the performance of any of the methods disclosed herein.

One aspect of the invention is a product of any of the methods disclosed herein, namely, an assay result, which may be evaluated at the site of the testing or it may be shipped to another site for evaluation and communication to an interested party at a remote location, if desired. As used herein, "remote location" refers to a location that is physically different than that at which the results are obtained. Accordingly, the results may be sent to a different room, a different building, a different part of city, a different city, and so forth. The data may be transmitted by standard means such as, e.g., facsimile, mail, overnight delivery, e-mail, ftp, voice mail, and the like.

"Communicating" information refers to the transmission of the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Figure 3:
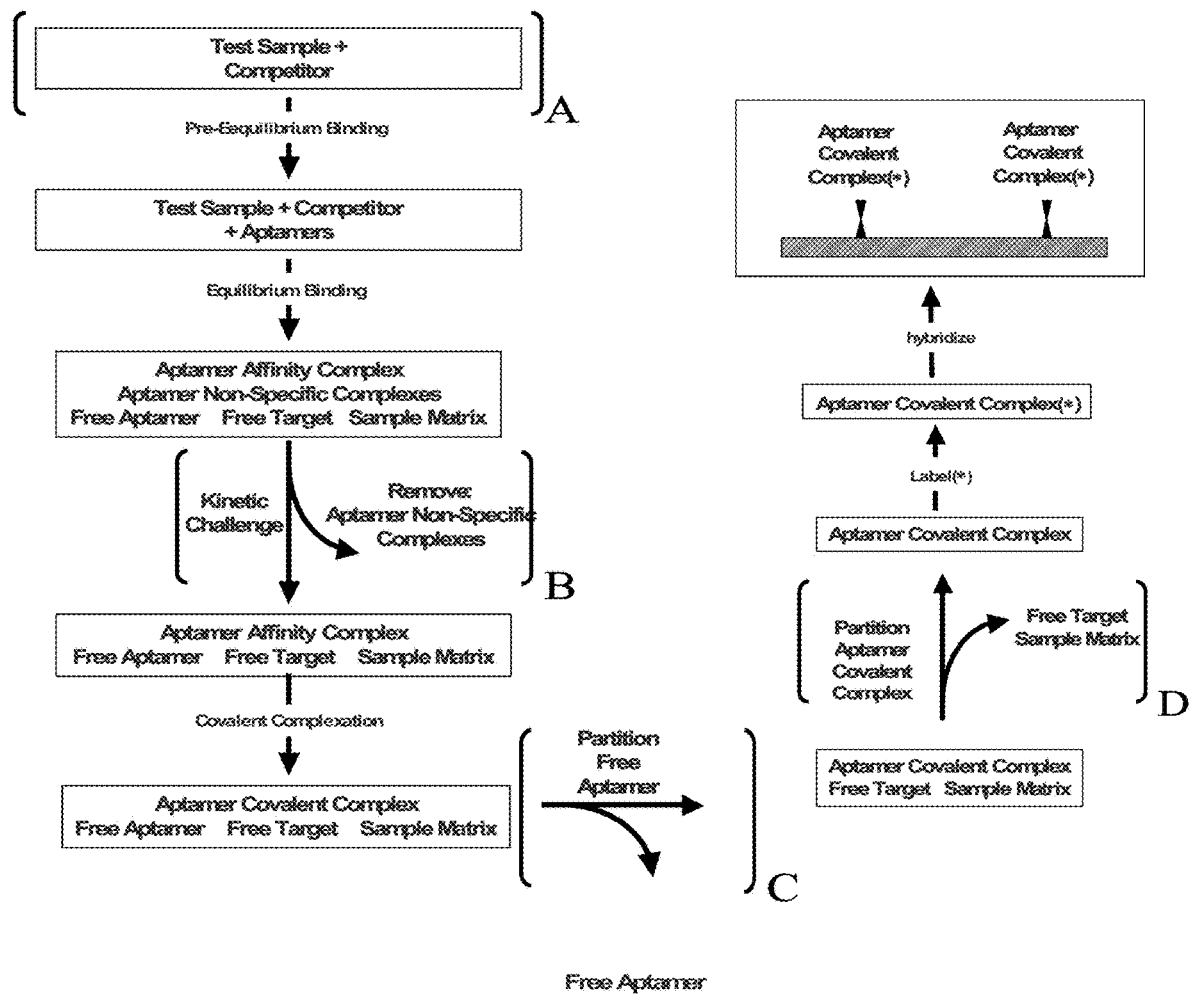
FIG. 3 illustrates an exemplary method for the detection and/or quantification of one or more target molecules that may be present in a test sample.

With reference to FIG. 3, in another exemplary method for the detection and/or quantification of one or more target molecules that may be present in a test sample, a test sample that may comprise a target molecule and at least one non-target molecule may be optionally contacted with a competitor molecule (indicated as Option A in FIG. 3). One or more non-specific complexes may form. The test sample is then contacted with an aptamer that includes a tag and has specific affinity for a target molecule. An aptamer affinity complex that comprises an aptamer bound to its target molecule is allowed to form. If the test sample contains the target molecule, an aptamer affinity complex will generally form in the test sample. Depending upon the nature of the test sample, one or more non-specific complexes between the aptamer and one or more non-target molecules may also form. If the test sample was contacted with a competitor molecule, various non-specific complexes that comprise the competitor may also have formed and be present in the test sample.

The test sample then may be optionally exposed to conditions that kinetically challenge components of the test sample (indicated as Option B in FIG. 3). As further described below, a kinetic challenge may comprise diluting the test sample, introducing a competitor molecule to the test sample, or the capture of aptamer affinity complexes on a solid support followed by washing, either with or without competitor molecules present in the wash solution. If a kinetic challenge is introduced, non-specific complexes between the aptamer and any non-target molecules are unlikely to re-form following dissociation. Since non-specific complexes generally dissociate more rapidly than an aptamer affinity complex, a kinetic challenge reduces the likelihood that an aptamer will be involved in a non-specific complex with a non-target. An effective kinetic challenge can provide the assay with additional specificity, beyond that of the initial aptamer binding event and the subsequent covalent interaction.

Regardless of whether a kinetic challenge is employed, the aptamer affinity complex that has formed is then converted, using a method appropriate to the aptamer being employed, to an aptamer covalent complex that comprises an aptamer covalently bound to its target molecule. Following aptamer covalent complex formation, any free or non-complexed aptamer that may be present in the test sample may be optionally partitioned from the test sample (indicated as Option C in FIG. 3). Optionally, any free or non-complexed non-target and target molecules that may be present in the test sample may be partitioned from the test sample (indicated as Option D in FIG. 3). Optionally, both free aptamer and free non-target and target molecules may be removed, in either order, after formation of the aptamer covalent complex.

If dilution is used to introduce a kinetic challenge, the subsequent test sample containing the aptamer covalent complex is preferably concentrated. If applicable, this concentration can be accomplished using methods described below with respect to the optional partitioning of any free aptamers from the test sample and/or the optional removal of other components of the test sample that can react with the labeling agent.

The aptamer covalent complex in the test sample is then detected and/or quantified using any of the method described herein or any other suitable method known to one of ordinary skill in the art. For example, the aptamer covalent complex can be attached to a surface of a solid support by contacting the solid support with the test sample and allowing a tag on the aptamer to associate, either directly or indirectly, with a probe that is immobilized on the surface of the solid support. The aptamer covalent complex that has associated with the probe on the solid support is then detected and optionally quantified. At any point prior to detection and optional quantification, that is, either anytime before attachment or after attachment of the aptamer covalent complex to the solid support, the aptamer covalent complex is contacted with a labeling agent to permit detection of the bound target molecule. As one of ordinary skill in the art will appreciate, the aptamer covalent complex can also be detected and/or quantified using mass spectrometry, Q-PCR, or any other suitable method known in the art.

As used herein, "competitor molecule" and "competitor" are used interchangeably to refer to any molecule that can form a non-specific complex with a non-target molecule. A "competitor molecule" or "competitor" is a set of copies of one type or species of molecule. "Competitor molecules" or "competitors" refer to more than one such set of molecules. Competitor molecules include oligonucleotides, polyanions (e.g., heparin, single-stranded salmon sperm DNA, and polydextrans (e.g., dextran sulphate)), abasic phosphodiester polymers, dNTPs, and pyrophosphate. In the case of a kinetic challenge that uses a competitor, the competitor can also be any molecule that can form a non-specific complex with an aptamer. Such competitor molecules include polycations (e.g., spermine, spermidine, polylysine, and polyarginine) and amino acids (e.g., arginine and lysine).

As used herein, "non-specific complex" refers to a non-covalent association between two or more molecules other than an aptamer and its target molecule. Because a non-specific complex is not selected on the basis of an affinity interaction between its constituent molecules, but represents an interaction between classes of molecules, molecules associated in a non-specific complex will exhibit, on average, much lower affinities for each other and will have a correspondingly higher dissociation rate than an aptamer and its target molecule. Non-specific complexes include complexes formed between an aptamer and a non-target molecule, a competitor and a non-target molecule, a competitor and a target molecule, and a target molecule and a non-target molecule.

As used herein, the terms "kinetically challenge" and "kinetic challenge" refer to a process of enrichment for an aptamer affinity complex from a set of complexes that includes an aptamer affinity complex and non-specific complexes, by applying kinetic pressure and making use of the different affinity characteristics of the constituents of such classes of complexes, including dissociation rates. A kinetic challenge generally results in an increase in specificity, since aptamer-non-target complexes are typically reduced compared to aptamer-target complexes. As used herein, the term "kinetic pressure" refers to a means for providing an opportunity for the natural dissociation of complexes and/or inhibiting the rebinding of molecules that dissociate from a complex naturally. Kinetic pressure can be applied by the addition of a competitor molecule, or by sample dilution, or by extensive washes when complexes are bound to a solid support, or by any other means known to one skilled in the art. As one of ordinary skill in the art will appreciate, because a kinetic challenge generally depends upon the differing dissociation rates of aptamer affinity complexes and aptamer-non-target complexes, the duration of the kinetic challenge is chosen so as to retain a high proportion of aptamer affinity complexes while substantially reducing the number of aptamer-non-target complexes. For a kinetic challenge to be effective, the dissociation rate for the aptamer affinity complex is preferably significantly lower than those for aptamer-non-target complexes. Since an aptamer can be selected to include particular properties, the constituents of an aptamer affinity complex can be designed to have a comparatively low dissociation rate.

As used herein, the term "partition" refers to a separation or removal of one or more molecular species from the test sample. Partitioning can be used to increase sensitivity and/or reduce background. Partitioning is most effective following aptamer covalent complex formation, when the aptamer affinity complex becomes irreversible due to the covalent bonds.

For example, removal of free aptamer from the test sample may increase assay sensitivity, since free aptamer may compete with an aptamer covalent complex during attachment of the aptamer covalent complex to a probe on the surface of the solid support. When using QPCR for detection and optional quantification, the removal of free aptamer facilitates detection and quantification of the target molecule. In one embodiment, the target molecule is a protein and free aptamer is partitioned from the aptamer covalent complex (and the rest of the test sample) by using reagents that precipitate proteins, and complexes that include proteins, such as the aptamer covalent complex, and not free nucleic acids in the test sample. Such reagents can include $K^+$/SDS, acetone, $(NH_4)_2SO_4$, ProCipitate, and other charged polymers that are known in the art.

In one embodiment, an aptamer, such as, for example, a tagged photoaptamer with a specific affinity for a target molecule, in this case a target protein, is introduced to the test sample. As further described herein, following the formation of an aptamer affinity complex and the conversion to an aptamer covalent complex, the aptamer-protein covalent complex and un-complexed protein are precipitated from the test sample using an appropriate reagent, such as any of the reagents listed above or any other suitable reagent. Precipitated components of the test sample are pelleted by centrifugation, and the supernatant containing free aptamer is discarded. The pellet, containing free protein and the aptamer-protein covalent complex, is then suspended in an appropriate solution, such as for example the assay binding diluent, and the aptamer covalent complex can then be contacted with a labeling agent either before or after attachment of the aptamer covalent complex to the solid support. The target molecule, if present in the test sample, is then detected and/or quantified by detecting the labeling agent on the aptamer covalent complex.

To reduce assay background, molecules that are capable of reacting with the labeling agent and that are not covalently linked to the aptamer may be removed from the test sample. In one embodiment, this is accomplished by precipitating the aptamer, both free and complexed, from the test sample, leaving other molecules that can react with the labeling agent in the supernatant to be discarded. Such nucleic acid precipitation can be accomplished with reagents that include cetyltrimethylammonium bromide (CTAB), dodecyltrimethylammonium bromide (DTAB), and organic solvents such as ethanol, for example. In another embodiment, the aptamer, both free and complexed, is partitioned from the sample by hybridizing the aptamer to a solid support. The solid support in this case may include microbeads (for example, paramagnetic beads), any other suitable solid supports described herein, and the like. After allowing the aptamer to hybridize to the surface of a suitable solid support, the solution containing molecules that can react with the labeling agent is easily removed, resulting in a concentration of the aptamer covalent complex. As one of ordinary skill in the art will appreciate, partitioning of the aptamer in this manner may use either a tag included on the aptamer or some other nucleic acid sequence on the aptamer to hybridize the aptamer to a suitably complementary nucleotide sequence attached to the solid support.

In one embodiment, a tagged aptamer, such as a tagged photoaptamer with a specific affinity for a target protein, is introduced to the test sample. As further described herein, following the formation of an aptamer affinity complex and the conversion to an aptamer covalent complex, the aptamer-protein covalent complex and free aptamer are precipitated from the test sample using an appropriate reagent, such as any of the reagents listed above or any other suitable reagent. Precipitated components of the test sample are pelleted by centrifugation, and the supernatant containing uncomplexed target and the remainder of the test sample is discarded. The pellet, which contains the free aptamer and the aptamer covalent complex, is then suspended in an appropriate solution, such as for example the assay binding diluent, and the aptamer covalent complex and free aptamer can then be contacted with a labeling agent either before or after attachment of the aptamer covalent complex to the solid support. The target molecule, if present in the test sample, is then detected and/or quantified by detecting the labeling agent on the aptamer covalent complex.

In another embodiment, a tagged aptamer, such as a tagged photoaptamer with a specific affinity for a target protein, is introduced to the test sample. As further described herein, following the formation of an aptamer affinity complex and the conversion to an aptamer covalent complex, the aptamer-protein covalent complex and free aptamer are captured on solid support using, for example, beads containing a probe that is complementary to the aptamer tag. The beads are pelleted either by magnetic force, in the case of paramagnetic beads, or centrifugation for non-paramagnetic beads, and the supernatant containing un-complexed target and test sample is discarded. The pellet is then suspended in an appropriate solution, such as for example the assay binding diluent, and the aptamer covalent complex and free aptamer are eluted using any suitable means for disrupting the hybridization interaction, including, for example, heat, high pH, distilled water, some combination of these, or any other known method. The beads are again pelleted, and the supernatant, containing the free aptamer and the aptamer covalent complex, can be contacted with a labeling agent either before or after attachment of the aptamer covalent complex to the solid support. The target molecule, if present in the test sample, is then detected and/or quantified by detecting the labeling agent on the aptamer covalent complex.

In another embodiment, the assay is performed as outlined above, up to and including the step where the beads are suspended after discarding the supernatant containing un-complexed target and test sample. Then, prior to eluting the free aptamer and aptamer covalent complex from the beads, the aptamer covalent complex may be contacted with a labeling agent, followed by repeated pelleting and washing to remove unreactive labeling agent prior to contacting the solid support with the aptamer covalent complex for detection and/or quantification of the target molecule.

In any of the methods disclosed herein, the test sample may be prepared as two or more dilutions of the test sample, which may increase the dynamic range of concentrations at which a target molecule can be present in a test sample and be subject to detection by the methods disclosed herein. The individual dilution test samples are separately assayed up to and including aptamer covalent complex formation, after which the dilution test samples may be pooled for the remainder of the assay and detected simultaneously on a single solid support. In one embodiment, each dilution test sample includes a unique aptamer, thereby enabling a single measurement of the corresponding target. In another embodiment, an aptamer can be added to two or more dilutions, each dilution contacting a distinctly tagged aptamer for a particular target, allowing for the detection of a specific aptamer signal for each of the different dilution samples on a single solid support. Chaining together diluted samples in this manner can extend a dynamic range for a single target molecule over many orders of magnitude and add accuracy when overlapping regions of quantification lead to multiple determinations of a single target's concentration.

In one embodiment, a set of test samples is prepared as serial dilutions to which a tagged aptamer, such as a tagged photoaptamer with a specific affinity for a target molecule, is introduced. The same aptamer with a different tag can be added to each test sample dilution. As further described herein, following the formation of an aptamer affinity complex and the conversion to an aptamer covalent complex, the individual test samples can be pooled and contacted with a labeling agent either before or after attachment of the aptamer covalent complex to the solid support. The target molecule, if present in the test sample, is then detected and/or quantified by detecting the labeling agent on the aptamer covalent complex. The resultant signals detected for each aptamer having a different tag can be combined to accurately quantify the amount or concentration of the target molecule in the original test sample. For example, the first dilution may result in a maximal signal for the target, yielding only semi-quantitative information, while the second dilution may result in a signal that is less than saturating, allowing for an accurate quantification of the target in the original test sample.

In another embodiment, a set of test samples is prepared as serial dilutions to which a tagged aptamer, such as a tagged photoaptamer with a specific affinity for a target molecule, is introduced. Different aptamers having unique tags may be added to each sample dilution. As further described herein, following the formation of aptamer affinity complexes and the conversion to aptamer covalent complexes, the individual test samples can be pooled and contacted with a labeling agent either before or after attachment of the aptamer covalent complexes to the solid support. Target molecules present in the test sample are then detected and/or quantified by detecting the labeling agent on the aptamer covalent complex. The resultant signals can be quantified for target ranges over many orders of magnitude depending on the different serial dilutions of the original sample.

In any of the methods disclosed herein, a test sample may be compared to a reference sample. A "reference sample" refers herein to any material, solution, or mixture that contains a plurality of molecules and is known to include at least one target molecule. The precise amount or concentration of any target molecules present in the reference sample may also be known. The term reference sample includes biological samples, as defined herein, and samples that may be used for environmental or toxicology testing, such as contaminated or potentially contaminated water and industrial effluents, for example. A reference sample may also be an end product, intermediate product, or by-product of a preparatory process, for example a manufacturing process. A reference sample may include any suitable assay medium, buffer, or diluent that has been added to a material, solution, or mixture obtained from an organism or from some other source (e.g., the environment or an industrial source).

In one embodiment, a reference sample is separately treated from a test sample in an identical manner up to, but not including, exposure to the labeling agent, which, in this embodiment only, must occur prior to attaching the aptamer covalent complex to the solid support. Two different labeling agents are used to differentiate target levels in the reference sample from the target levels in the test sample. After the samples are contacted with the labeling agent, they can be equally mixed and can be contacted with the solid support simultaneously. A direct comparison of any differential expression (i.e., differential amount or concentration of the target in the samples) between the reference sample and the test sample is then possible by measuring the signal from each labeling agent separately. The two labeling agents can include a Cy3 and Cy5 pair, and an Alexa555 and Alexa647 pair. In one embodiment, the reference sample can be a pooled biological sample representing a control group. In another embodiment, the reference sample can be a biological sample obtained from an individual, collected at a first time, and the test sample can be obtained from the same individual but collected at a second time, thereby facilitating a longitudinal study of an individual by measuring and evaluating any changes in the amount or concentration of one or more target molecules in multiple biological samples provided by the individual over time.

In one embodiment, a tagged aptamer, such as a tagged photoaptamer with a specific affinity for a target molecule, is introduced to both a reference sample and a test sample. As further described herein, following the formation of an aptamer affinity complex and the conversion to an aptamer covalent complex, the two samples can be contacted with two distinct labeling agents, containing two different detection molecules. The two separately labeled samples containing the aptamer covalent complex can then be attached to the solid support. The target molecule, if present in either or both of the samples, is then detected and/or quantified by detecting the two labeling agents on the aptamer covalent complex, typically by performing multiple scans at different excitation and emission wavelengths when the detection label is a fluorescent molecule, for example. Such quantification may lead to more accurate assessment of differential target amounts or concentrations in the reference sample and the test sample and can facilitate comparisons among different test samples when the reference sample employed is the same.

In any of the methods disclosed herein, multiple labeling agents may be used to analyze a single test sample. In one embodiment, two or more labeling agents, each with a distinct chemistry for labeling different target molecule moieties and an optionally different detection group, can be used with a single test sample. The different chemistries will label different functional groups on the target molecule from which additional information may be derived. For example, in the case of a target protein, one label may be attached to the target using chemistry that reacts with primary amines (e.g., lysines), while a second label is attached to the target through chemistry that reacts with, for example, carbohydrate groups that are typically associated with glycosylated proteins. The relative quantification of these two moieties on the same target molecule, recognized by a common aptamer, can provide useful information about the extent of glycosylation for that target within the test sample.

In one embodiment, a tagged aptamer, such as a tagged photoaptamer with a specific affinity for a target molecule, is introduced to a test sample. As further described herein, following the formation of an aptamer affinity complex and the conversion to an aptamer covalent complex, the test sample can be contacted with two distinct labeling agents, containing two different detection molecules, either before or after contacting the aptamer complex with the solid support. In one embodiment, the detection labels and the chemistries are unique, allowing for sequential labeling of the same test sample containing an aptamer covalent complex. In another embodiment, the chemistries may be carried out simultaneously in one reaction. The multiply-labeled aptamer covalent complex can then be detected and/or quantified by detecting the two labeling agents on the aptamer covalent complex, typically by performing multiple scans at different excitation and emission wavelengths when the detection labels are fluorescent molecules, for example.

In another embodiment, two or more distinct labeling agents employ the same detection label. The assay proceeds as described above, up to and including the conversion to an aptamer covalent complex, after which the test sample is split into as many aliquots as there are distinct labeling agents, and each aliquot of the test sample is contacted separately with a labeling agent either before or after attachment of the aptamer covalent complex to the solid support. The separately labeled aliquots of the test sample containing the aptamer covalent complex can be detected and/or quantified separately.

Any of the methods described herein may be used to conduct a multiplexed analysis of a test sample. Any such multiplexed analysis can include the use of at least two, at least tens, at least hundreds, or at least thousands of aptamers to simultaneously assay an equal number of target molecules in a test sample, such as a biological sample, for example. In these embodiments, a plurality of tagged aptamers, such as tagged photoaptamers, that each have a specific affinity for a target molecule is introduced to the test sample. As further described herein, following the formation of aptamer affinity complexes and the conversion to aptamer covalent complexes, the aptamer covalent complexes are attached to a solid support through a plurality of corresponding probes that are immobilized on the solid support. The aptamer covalent complexes can be contacted with a labeling agent either before or after attachment of the aptamer covalent complexes to the solid support. Target molecules present in the test sample are then detected and/or quantified by detecting the labeling agent on the aptamer covalent complex.

Another aspect of the present invention relates to kits useful for conveniently performing any of the methods disclosed herein to analyze test samples. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending upon the cross-reactivity and stability of the reagents.

A kit comprises, in packaged combination, at least one tagged aptamer, a solid support including at least one probe, and a suitable labeling agent. The kit may also include washing solutions such as buffered aqueous medium for sample dilution as well as array washing, sample preparation reagents, and so forth. The relative amounts of the various reagents in the kits can be varied widely to provide for concentrations of the reagents that substantially optimize the reactions that need to occur during the assay and to further substantially optimize the sensitivity of the assay. Under appropriate circumstances, one or more of the reagents in the kit can be provided as a dry powder, usually lyophilized, including excipients, which upon dissolution will provide a reagent solution having the appropriate concentrations for performing a method or assay in accordance with the present invention. The kit can further include a written description of a method in accordance with the present invention as described herein.

In an exemplary embodiment, a kit for the detection and/or quantification of one or more target molecules that may be present in a test sample includes at least one aptamer having specific affinity for a target molecule and comprising a tag; a labeling agent; and a solid support, wherein the solid support includes at least one probe disposed thereon, and wherein the probe is capable of associating with the tag on the aptamer.

EXAMPLES

The following examples are provided for illustrative purposes only and are not intended to limit the scope of the invention as defined in the appended claims.

Example 1. Photoaptamer Assay Measuring VEGF Serially Diluted into Buffer and Plasma Using Hybridization Capture by Probes Immobilized on a Surface for Detection and Quantification This example illustrates the steps of the assay as illustrated in FIGS. 2A, 2B, and 2C for a single photoaptamer and its target protein. The assay is performed using two different test samples, buffer and plasma.

A. Preparation of Oligonucleotides.

A DNA oligonucleotide tag included on the 3' end of the photoaptamer was used here. In this case, the tag was the 3' fixed region used during the SELEX protocol. The VEGF photoaptamer 509-80 was synthesized using standard protocols for phosphoramidite DNA synthesis on solid phase using a conventional synthesizer. The 5-BrdU containing photoaptamer was cleaved and deprotected in milder conditions than are standard in DNA synthesis, using t-butylamine:methanol:water in a 1:1:2 ratio at 70° C. for 5 hours, filtered and evaporated to dryness. The aptamer was purified using ethanol precipitation followed by reverse-phase HPLC. DNA probes complementary to the tag on the photoaptamer and including an amine reactive group were synthesized as described above and cleaved and deprotected using standard protocols for DNA. Probes were purified using ethanol precipitation only.

B. Immobilization of Capture Probes onto an Amine Reactive Surface.

The reverse complement of the capture tag was synthesized as described above with a 5' amine and coupled to an amine-reactive slide surface comprised of a cyclic-olefin copolymer (COC) substrate coated with a methacrylate copolymer, as further described in International Application Number PCT/US2006/008877 (WO 2006/101798), filed Mar. 14, 2006, entitled "Polymer Compound for Biomedical Use and Biochip Substrate Using Such a Polymer Compound" and referred to herein as the "methacrylate copolymer surface." Microarrays of capture probes were printed onto the surface. Briefly, amine containing capture probes were reacted with active ester groups embedded in the surface. The capture probes were diluted to 20 µM in a buffer consisting of 300 mM sodium phosphate, 25 mM sodium borate (pH 9.5 at 21° C.), 0.01% Tween® 20 and 1 mM 4-dimethylaminopyridine (DMAP). Capture probes were deposited in 250 µL spots in triplicate on the slide surface in an array using a GeneMachines OmniGrid Accent microarrayer. The arrayed slides were incubated in 65% humidity for 1 hour at room temperature followed by 65° C. for 1 hour and finally over night at room temperature. Remaining amine-reactive groups were hydrolyzed in 20 mM NaOH for 5 minutes, followed by 10 $H_2O$ rinses and then dried under a stream of $N_2$. Prior to usage, slides were stored in the dark at room temperature in a dessication chamber.

VEGF Aptamer 509-80 was incubated at 1 nM concentration with serially diluted target protein VEGF, from 5 nM to 1.6 pM, in 100 µL of assay diluent (1×SB17 (40 mM HEPES, 102 mM NaCl, 5 mM KCl, 5 mM $MgCl_2$, 1 mM EDTA), 0.1% Tween® 20, 0.05% BSA, 100 µg/mL herring sperm DNA) or in 10% plasma (10% plasma in 1×SB18 (40 mM HEPES, 102 mM NaCl, 5 mM KCl, 5 mM $MgCl_2$), 200 µg/mL herring sperm DNA, 0.1% Tween® 20). The samples were mixed gently and incubated at 37° C. for 30 minutes. The samples were irradiated with 1 Joule of 308 nm light delivered by an excimer laser (Tui Laser ExciStar 5200, 10 ns pulse length, 200 Hz, 0.8 mJ per pulse). Staining was initiated by addition to each sample of 1 µL of succinimidyl-Alexa647 at 10 mg/mL in DMSO. The solutions were mixed and reacted overnight at 4° C. The stain reaction was quenched by adding 5 µL of 10% BSA and incubating for 2 hours. Finally, 18 µL of 5 M NaCl and 4.5 µL of 10% Triton were added to 90 µL of the 10% plasma samples, and 18 µL of 5 M NaCl and 0.9 µL of 10% Triton were added to 90 µL of the buffer samples. A Grace Proplate gasket was attached to a slide containing the immobilized probes, creating 16 wells. Each well was incubated for 15 minutes at 42° C. with 80 µL of a solution composed of 600 µL of 5 M NaCl, 30 µL of 10% Triton and 3 mL of assay diluent. This solution was then removed and replaced with 80 µL of sample. The wells were sealed with Microseal 'F' Film and the slide was mixed at 600 rpm, 37° C. on an Eppendorf Thermomixer R for 3 hours. The hybridization solutions were removed and the wells rinsed 3 times with a solution composed of SB17, 0.5% Triton, 100 µg/mL herring sperm DNA and 1 M NaCl. The gasket was then removed and the entire slide was placed in a pap jar in 30 mL of a solution composed of SB17, 0.5% Triton and 1 M NaCl for 30 minutes, followed by a 2 minute rinse in 1×SB17, 0.05% Tween® 20, followed by a 30 second rinse in 0.5×SB17. The slide was dried under a stream of $N_2$ and scanned with a TECAN LS300 fluorescent scanner (excitation 633 nm/emission 670 nm). The resulting TIF image was analyzed with ArrayVision Software from Imaging Research, Inc. to isolate features and compute their average intensities using standard techniques for processing microarray images.

Figure 4A:
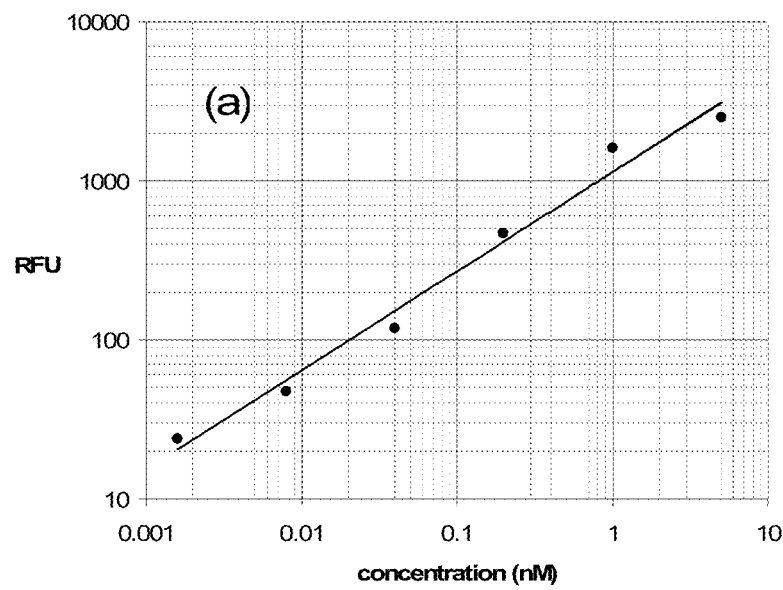
FIGS. 4A and 4B show dose response curves for serial dilutions of VEGF in buffer (FIG. 4A) and plasma (FIG. 4B) using the assay depicted in FIGS. 2A, 2B, and 2C. The no-protein buffer response has been subtracted from each data point in both sets. The least-squares line fit to the log transformed data is shown.
Figure 4B:
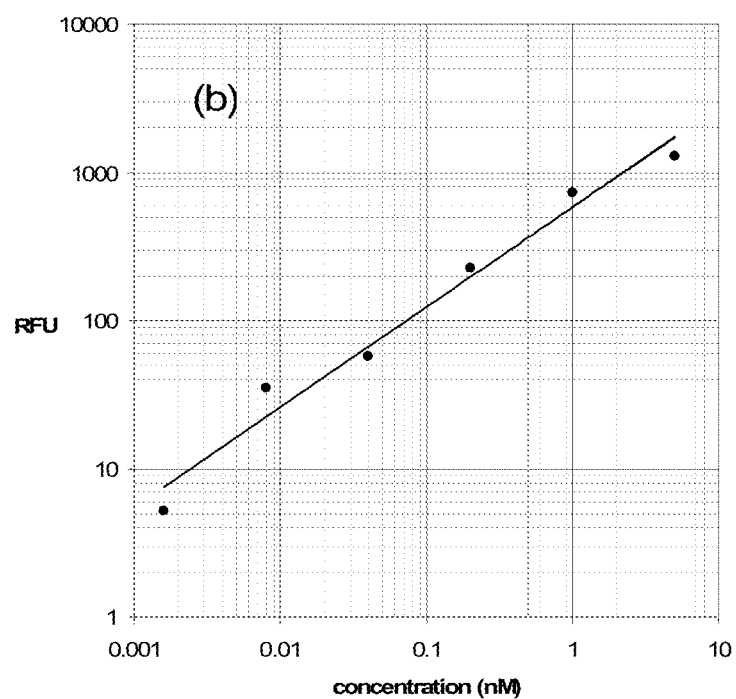
Figure 5A:
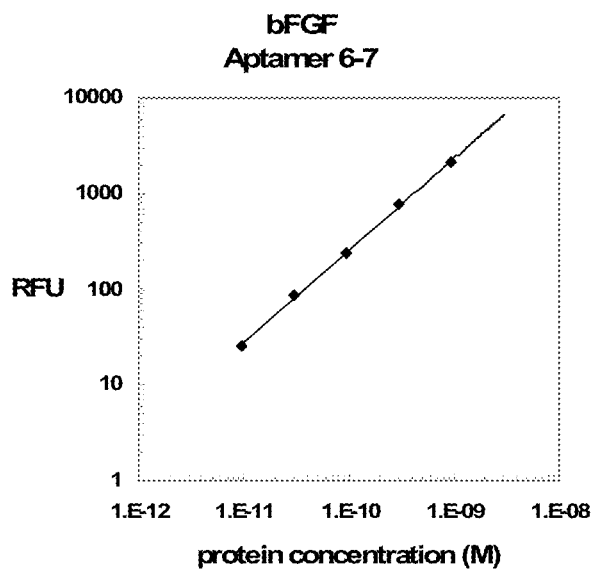
FIGS. 5A-5J show dose response curves for serial dilutions of 10 target proteins multiplexed with 41 photoaptamers in buffer using the assay depicted in FIGS. 2A, 2B, and 2C. The no-protein buffer response for each aptamer has been subtracted from each data point within that set. The least-squares line fit to the log transformed data is also plotted. Only the data points used in the line fit are shown.
Figure 5B:
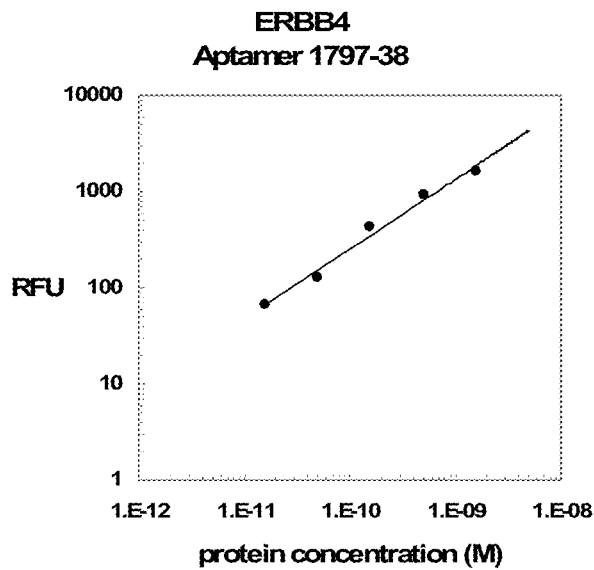
Figure 5C:
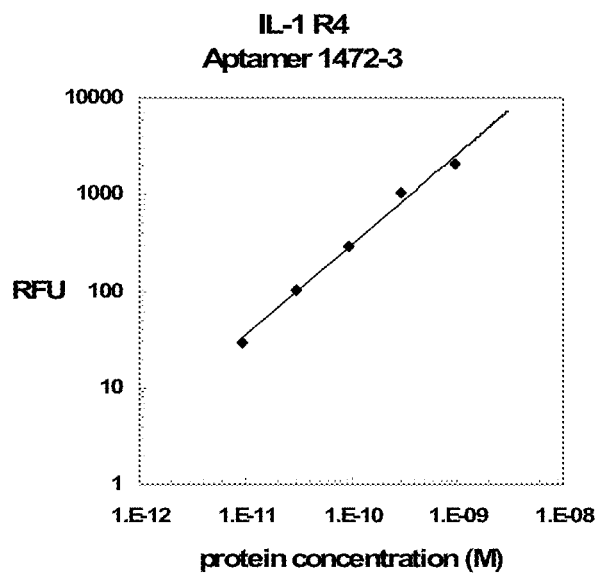
Figure 5D:
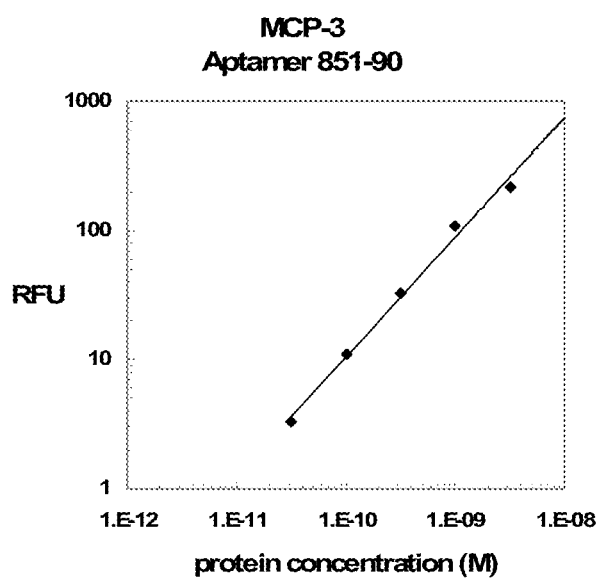
Figure 5E:
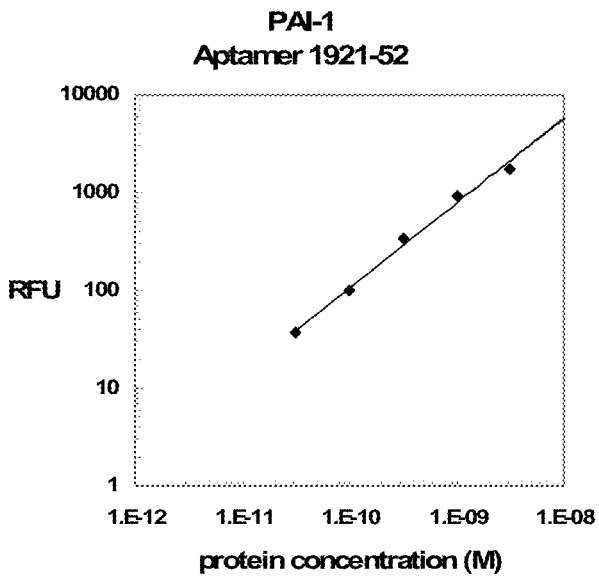
Figure 5F:
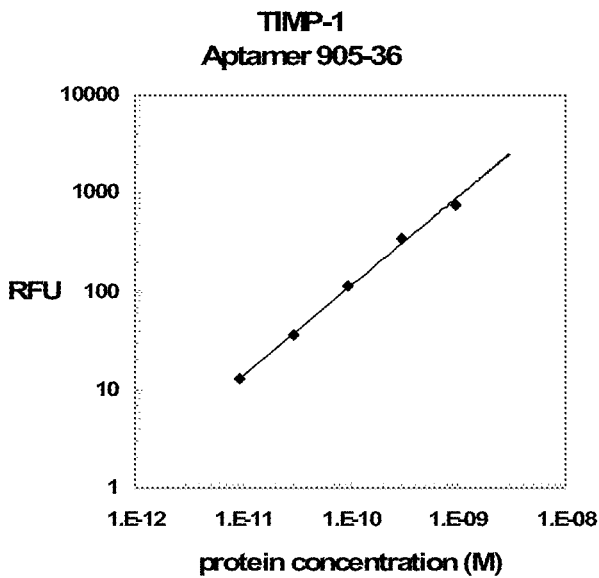
Figure 5G:
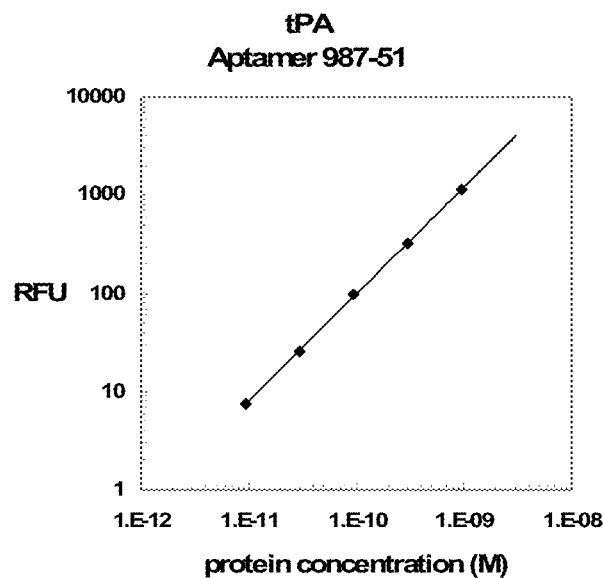
Figure 5H:
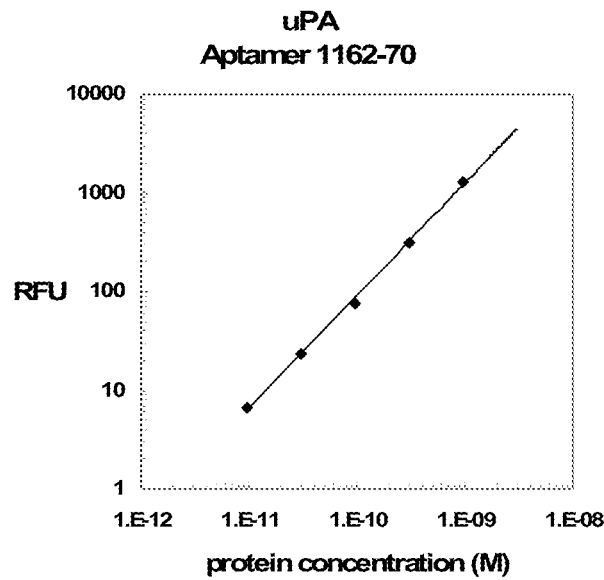
Figure 5I:
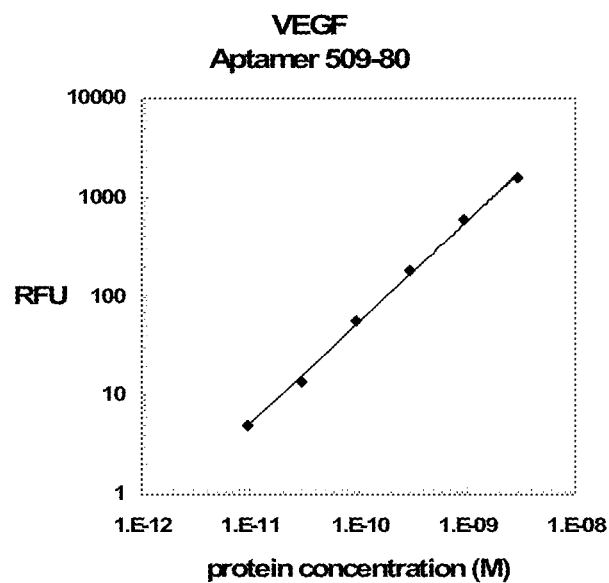
Figure 5J:
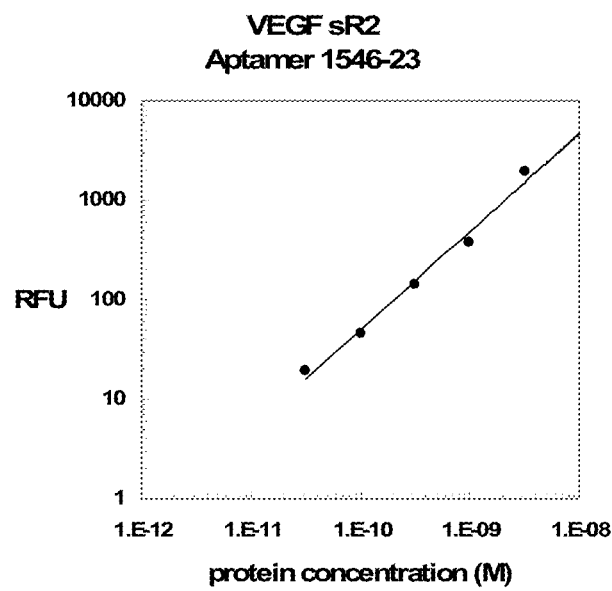

The results are set forth in FIG. 4 where the buffer (FIG. 4A) and plasma (FIG. 4B) results have been quantified as described above for the VEGF aptamer capture probe. The linear response for serial dilution in both media, obtained with subtraction of the no protein buffer control from each response, encompasses the range from 2 pM to 5 nM in VEGF concentration.

Example 2. Photoaptamer Assay Using Hybridization Capture by Probes Immobilized on a Surface for Detection and Quantification of Multiple Target Proteins in Buffer This example illustrates the steps of the assay as illustrated in FIGS. 2A, 2B, and 2C in a multiplexed format using 10 photoaptamers and their target proteins in buffer.

A. Preparation of Tagged Photoaptamer.

Unique oligonucleotide tags were assigned to each photoaptamer from the reverse complements of a set of gene expression probes obtained from the Affymetrix GeneChip® Test3 Array. The tagged photoaptamers were prepared as described in Example 1 except the amine group was added to the 5' end of the photoaptamers. Prior to use, aptamer solutions were heated to 95° C. for 3 minutes followed by controlled cooling to 37° C. at a rate of 0.1° C. per second.

B. Immobilization of Capture Probes onto an Amine Reactive Surface.

The reverse complements of the capture tags were immobilized as described in Example 1 except a 3' amine was used here for the probes and 0.0025% Tween® 20 was used while DMAP was eliminated from the print buffer. The printed slides were incubated at 65° C. for 2 hours, followed by overnight storage in a dessicator. 'Slides were then treated with a solution of methoxy ethyl amine (pH 9.5 @ 37° C.) to remove unbound probe and consume excess active ester groups on the surface.

The assay follows the scheme outlined in FIGS. 2A, 2B, and 2C. The basic protocol described in Example 1 was used. However, 41 photoaptamers were multiplexed and 10 target proteins to a subset of these aptamers were serially diluted in the samples. The protein:photoaptamer pairs quantified in this example include bFGF:6-7, ERBB4:1797-38, IL-1 R4:1472-3, MCP-3:851-90, PAI-1:1921-52, TIMP-1:90536, tPA:987-51, uPA:1162-70, VEGF:509-80, VEGF sR2:1546-23.

41 photoaptamers, each at a concentration of 2 nM, were incubated with 6 serial dilutions of 10 target proteins and one no protein control in 100 μL of assay buffer (SB17, 0.1% Tween® 20) for 30 minutes at 37° C. The samples were irradiated and stained as described in Example 1 except 2.1 μL of succinimidyl-Alexa647 was used and the reaction was incubated for 2 hours at room temperature in the dark. The stain reaction was quenched by the addition of 25 μL of 5M NaCl, 5 μL of Triton X-100, 13.5 μL of 100 mM glycine and 1.5 μL of 10 mg/mL herring sperm DNA and incubated for 40 minutes at room temperature in the dark, followed by 2 minutes at 70° C. Prior to hybridization, gasketed slides arrayed with hybridization probes were prepared as described in Example 1. The pre-hybridization solution was removed and the hybridization samples were added to the wells and incubated at 45° C. for 2 hours in a humid chamber. 'The hybridization solutions were removed and the wells rinsed 3 times with a 45° C. wash solution composed of 1×SB17, 0.33% Triton X-100 and 1 M guanidinium hydrochloride. The gaskets were then removed and each entire slide was placed in a pap jar with the wash buffer for 20 minutes at 45° C., followed by a 2 minute rinse in 1×SB17, 0.1% Tween® 20, and a final rinse in 0.25×SB17. The slide was dried, scanned and quantified as described in Example 1. The results are set forth in FIG. 5, which illustrates the signal generated from the multiplexed assay for protein concentrations ranging from 10 pM to 1 nM in buffer for ten target proteins.

Example 3. Photoaptamer Assay Using Hybridization Capture by Probes Immobilized on a Surface for Detection and Quantification of Multiple Target Proteins in Serum This example demonstrates the utility of the assay as illustrated in FIGS. 2A, 2B, and 2C in a multiplexed format using 57 photoaptamer for measurements in serum samples.

A. Preparation of Tagged Photoaptamer.

The tagged photoaptamers were prepared as described in Example 2.

B. Immobilization of Capture Probes on an Amine Reactive Surface.

The reverse complements of the capture tags were immobilized as described in Example 2.

The 57 photoaptamers were split into two sets for multiplexing, one of 27 aptamers to low abundant targets and one of 30 aptamers to high abundant targets in human serum or plasma. 14 serum samples were prepared in two dilutions and mixed with the two sets of aptamers to give a final concentration of 1 nM for each aptamer and 10% serum, 0.9×SB1, 0.1% Tween® 20, 50 mg/mL lghsDNA, 10 mg/mL (BrdU)$_{30}$ for the 27 aptamer set and 1% serum, 0.99×SB1, 0.1% Tween® 20, 5 mg/mL lghsDNA, 1 mg/mL (BrdU)$_{30}$ for the 30 aptamer set. SB1 is comprised of 40 mM HEPES, 102 mM NaCl, 5 mM KCl, 1 mM MgCl$_2$, and 1 mM CaCl$_2$. The samples were equilibrated, crosslinked and stained as described in Example 2. The stain reaction was quenched by the addition of 10 μL of 10% low fatty acid (FA) BSA, 25 μL of 5 nM NaCl, 5 μL of 10% Triton X100 and 7 μL 100 mM glycine and incubated for 40 minutes at room temperature. After quenching, 1.5 μL of 10% SDS was added and the samples were heated to 42° C. for two minutes.

Gasketed slides were prepared as described in Example 1 and incubated with 1×SB1, 0.1% Tween® 20, 0.66% low FA BSA, 830 mM NaCl, 0.33% Triton X100, 0.1% SDS, 50 mg/mL large herring sperm DNA and 10 mg/mL (BrdU)$_{30}$ for 15 minutes. The pre-hybridization buffer was removed, stained samples added and incubated in a humid chamber at 60° C. for 2 hours. After hybridization, the slides were washed, dried, scanned and quantified as described in Example 2.

Figure 6A:
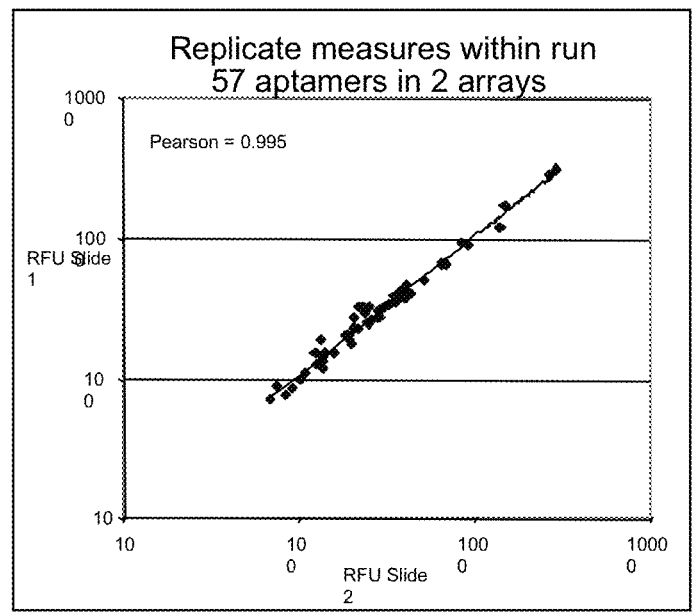
FIGS. 6A and 6B show replicate measurements in RFU for the response of 57 photoaptamers in serum samples for two individuals obtained from the assay outlined in FIGS. 2A, 2B, and 2C. Both replicate measurements exhibit very good reproducibility for the 57 targets measured, producing Pearson correlations greater than 0.99.
Figure 6B:
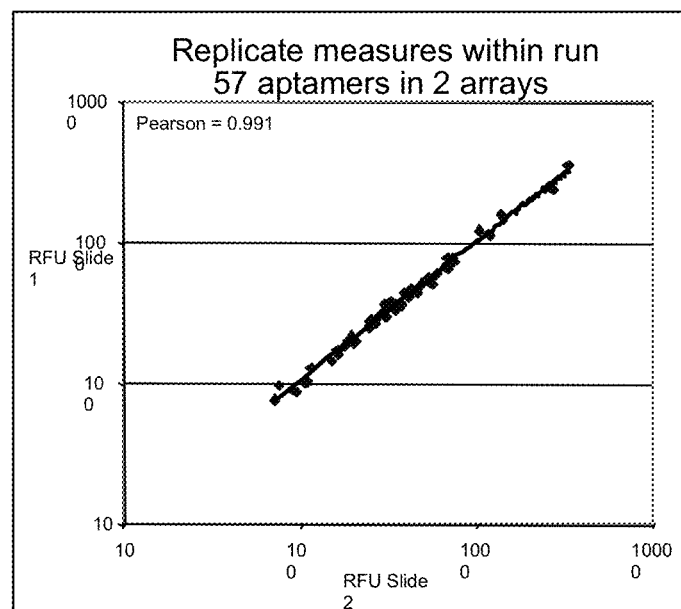

FIG. 6 shows the signals quantified from the scanned images for replicate measurements of the 57 photoaptamers for serum samples from two individuals. The measurements are demonstrated to be highly reproducible, with Pearson correlations better than 0.99 for aptamer measurements between the replicate samples.

Example 4. Kinetic Challenge with Dilution in Photoaptamer Assay Using Hybridization Capture by Probes Immobilized on a Surface This example illustrates the use of two optional steps in the assay depicted in FIG. 3, a kinetic challenge followed by removal of free protein. The kinetic challenge, accomplished by dilution, illustrates the loss of aptamer-protein non-specific complexes with retention of the aptamer-target affinity complexes in plasma. This example also illustrates the use of bead capture to concentrate the sample after dilution and to permit removal of free protein prior to staining.

A. Preparation of Tagged Photoaptamer 987-51.

The tagged photoaptamer was prepared as described in Example 2.

B. Immobilization of Capture Probes onto an Amine Reactive Surface.

The reverse complements of the capture tags were immobilized as described in Example 2.

Photoaptamer 987-51 at 20 nM concentration was mixed with two no-protein controls and 10 serially diluted concentrations of target protein tPA in either assay buffer (SB17, 0.1% Tween® 20) or plasma (10% plasma in SB18, 0.1% Tween® 20). To assess response in the absence of a kinetic challenge, two additional control samples were prepared in both buffer and plasma, one with no-protein and one with the highest protein concentration. These 28 samples in 10 μL volumes, 14 each for buffer and plasma, were incubated for 30 minutes at 37° C. The first 12 samples in both buffer and plasma were diluted 50-fold by addition of SB17, 0.1% Tween® 20 and incubated for 5 minutes, followed by irradiation of all twenty-eight samples with 1 J UV light (OAI Hg lamp filtered light source). After irradiation, the remaining two samples each in buffer and plasma were diluted 50-fold as described above.

Each sample was adjusted to 1 M NaCl and incubated at 45° C. for 90 minutes with 25 μg of Dynal paramagnetic beads coupled to an oligonucleotide complementary to the 3' end of aptamer 987-51. Samples were centrifuged at 1000 g for 2 minutes and the supernatant removed. The beads were washed 3 times with 100 μL SB17, 0.1% Tween® 20. Beads were suspended in 100 mM sodium bicarbonate, 1 mM EDTA, 0.02% Tween®-20, 0.2 mg/mL Alexa647-NHS dye, and shaken at room temperature for 1 hour. The stain solution was removed and replaced with 100 μL SB17, 0.1% Tween-20, 10 mM glycine to quench the stain reaction. Beads were next washed 3 times with 100 μL volumes of guanidine wash buffer (SB17, 0.1% Tween-20, 0.33% Triton X-100, 1 M guanidine hydrochloride), suspended in 70 μL 0.33% Triton X-100, 1 mg/mL dextran sulfate and heated at 95° C. for 5 minutes to elute the aptamers from the magnetic beads. Gasketed slides were prepared and pre-hybridized as described in Example 2. 65 μL of each supernatant containing eluted aptamers was transferred to a well containing 25 μL of 3.6 M NaCl, 144 mM HEPES, 0.33% Triton X-100. The slides were incubated in a humid chamber at 45° C. overnight then washed, dried, scanned and quantified as described in Example 2.

Figure 7:
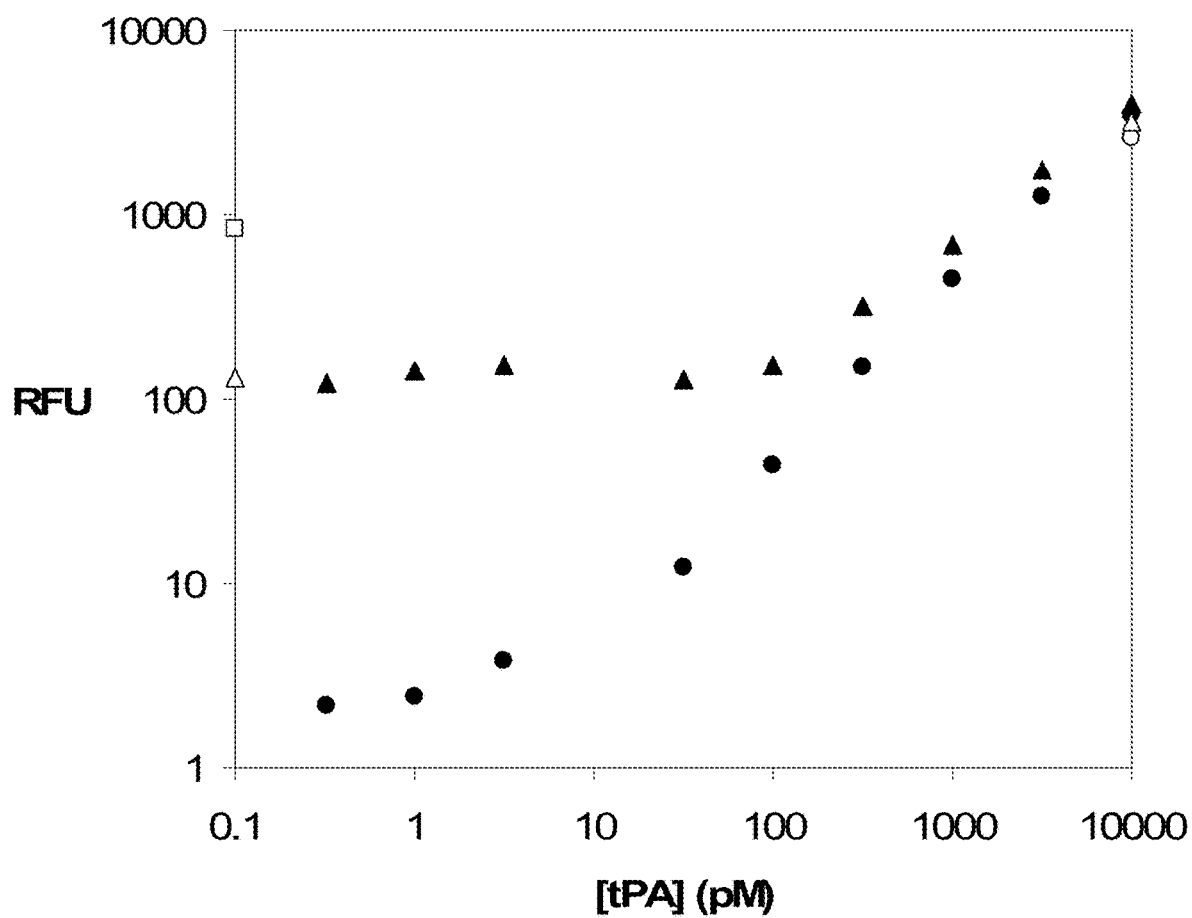
FIG. 7 shows dose response curves for tPA in buffer (●) and plasma (▲) using a UPS hybridization capture assay with the optional kinetic challenge. The no-protein buffer response was averaged and subtracted from both curves. For the plasma sample with no added target protein, the diluted plasma response without kinetic challenge is denoted by (□) and that with kinetic challenge is denoted by (Δ) at 0.1 pM tPA. The measured response is reduced by almost a log due to the kinetic challenge in plasma, whereas the target-aptamer response is unchanged, as evidenced by (○) (buffer) and (Δ) (plasma) at 10 nM added tPA.

FIG. 7 shows a graphical representation of the results in buffer (●) and plasma (▲) after 50-fold dilution. The signal obtained from the high protein control samples with no dilution (○ buffer, Δ plasma) are in good agreement with the diluted values, indicating little loss of target signal during the kinetic challenge. The no-protein plasma RFU without and with dilution is 838 RFU (□ at 0.1 pM) and 131 RFU (Δ), resulting in an 84% drop in signal presumably due to removal of aptamer non-specific complexes during the kinetic challenge.

Example 5. Kinetic Challenge with Competitors in Photoaptamer Assay Using Hybridization Capture by Probes Immobilized on a Surface This example illustrates the optional step of introducing a kinetic challenge in the assay depicted in FIG. 3. The kinetic challenge, accomplished in this example by the addition of a competitor molecule, illustrates the loss of aptamer-protein non-specific complexes while maintaining aptamer-target affinity complexes in plasma.

A. Preparation of Tagged Photoaptamer 987-51.

The tagged photoaptamer was prepared as described in Example 2.

B. Immobilization of Capture Probes onto an Amine Reactive Surface.

The reverse complements of the capture tags were immobilized as described in Example 2.

Photoaptamer 987-51 at 20 nM concentration was mixed with a no-protein control and 6 serially diluted concentrations of target protein tPA in 10% plasma diluted into SB18, 0.1% Tween® 20. Two sets of samples were prepared to facilitate comparisons between samples with and without competitor addition. Each solution was incubated at 37° C. for 30 minutes. After the 30 minute equilibration, half of each sample from one set was added to the same volume of 550 μM $dN_{15}$ competitor in SB17, 0.1% Tween® 20 at 37° C. and incubated for 9 minutes followed by irradiation as described in Example 4. After irradiation, SB17, 0.1% Tween-20 was added to the no competitor set of samples to equal the volume of the competitor addition. The samples were stained as described in Example 4 except the incubation time was 2 hours. The stain reaction was quenched with the addition of 45 μL 0.83 M NaCl, 0.33% Triton X-100, 0.1 mg/mL large herring sperm DNA and 9 mM glycine. The samples were mixed and incubated in the dark at room temperature for 40 minutes, followed by heating to 70° C. for 2 minutes.

Gasketed slides were prepared as described in Example 2 and incubated in a solution of SB18, 0.1% Tween® 20, 0.33% Triton X-100 and 100 μg/mL large herring sperm DNA. Samples were added to slide wells and incubated in a humid chamber at 45° C. overnight then washed, dried, scanned and quantified as described in Example 2.

Figure 8:
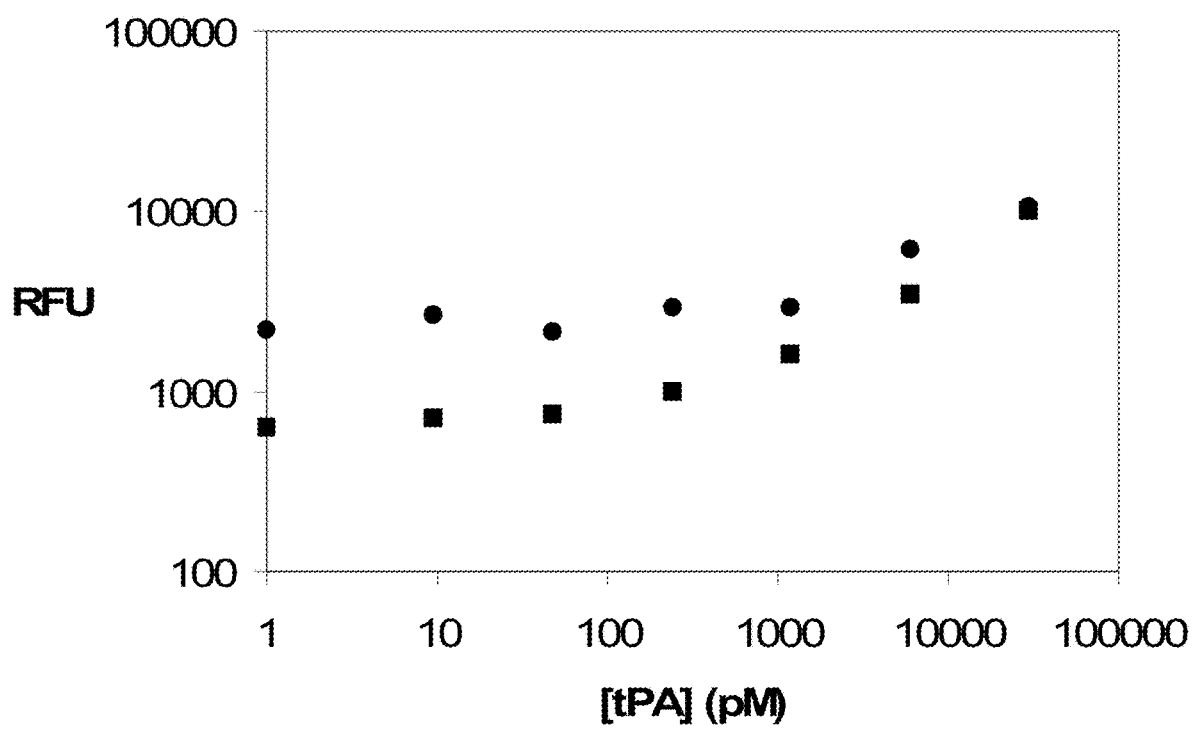
FIG. 8 shows dose response curves for tPA in plasma using the assay with the optional kinetic challenge with competitor (■) and without (●). The no-protein plasma value is plotted at 1 pM [tPA] and is reduced by 70% due to the addition of competitor, whereas the target-aptamer response is unchanged, as evidenced by the responses at 30 nM tPA, which are essentially the same in the presence or absence of competitor.

The results are shown in FIG. 8, where the dose response curves for tPA in plasma with and without the addition of the competitor are presented. The plasma value with no added protein is reduced by 70% due to the addition of competitor, whereas the response to the highest target concentration is unchanged in the presence competitor.

Example 6. Kinetic Challenge with Bead Capture and Washing of Aptamer Affinity Complexes in Photoaptamer Assay Using Hybridization Capture by Probes Immobilized on a Surface This example illustrates the optional step of introducing a kinetic challenge in the assay depicted in FIG. 3. The kinetic challenge in this example is accomplished by capturing aptamer affinity complexes on beads and washing the immobilized complexes such that dissociated target proteins are removed prior to crosslinking.

A. Preparation of Tagged Photoaptamers 987-51, 1152-46, and 1920-1.

The tagged photoaptamers were prepared as described in Example 2.

B. Immobilization of Capture Probes onto an Amine Reactive Surface.

The reverse complements of the capture tags were immobilized as described in Example 2.

Photoaptamers 987-51, 1152-46, and 1920-1 at 4 nM concentration were mixed with biotinylated probes complementary to the unique tag sequence of each photoaptamer at 8 nM concentration and incubated for 15 seconds at 95° C., then slow-cooled at 0.1° C. per second to 37° C. The photoaptamer:biotinylated probe complexes at a concentration of 0.2 nM photoaptamer:0.4 nM probe were mixed with a no-protein control and 6 serially diluted concentrations of target proteins tPA, PAI-1, and IL-6 in either assay buffer (SB17, 0.1% Tween® 20) or plasma (10% plasma in SB18, 0.1% Tween® 20). These 14 samples in 100 μL volumes, 7 each for buffer and plasma, were incubated for 30 minutes at 37° C., after which 50 µg of Dynal MyOne Streptavidin beads were added to each sample and incubated for 2 minutes at 37° C. with mixing to capture the non-covalent photoaptamer:biotinylated probe:protein complexes. The beads were washed 3 times for 30 seconds with 100 uL SB17, 0.1% Tween® 20, 0.1 mg/mL herring sperm DNA, resuspended in 100 µL of the same, and irradiated with 4 J UV light (OAI Hg lamp filtered light source) with mixing.

The beads were washed once with 100 mM sodium bicarbonate, 1 mM EDTA, 0.02% Tween®-20, resuspended in 100 mM sodium bicarbonate, 1 mM EDTA, 0.02% Tween®-20, 0.2 mg/mL Alexa647-NHS dye, and shaken at room temperature for 1 hour. Beads were next washed 3 times with 100 µL SB17, 0.1% Tween-20, 0.33% Triton X-100, 1 M guanidine hydrochloride, 25 mM glycine, once with 100 µL SB17, 0.1% Tween-20, 0.33% Triton X-100, and suspended in 95 µL 40 mM HEPES, pH 7.5, 0.33% Triton X-100 and heated at 70° C. for 5 minutes to elute the aptamers from the magnetic beads. Gasketed slides were prepared and pre-hybridized as described in Example 2. 90 µL of each supernatant containing eluted aptamers was combined with 30 µL of 40 mM HEPES, pH 7.5, 3 M NaCl, 0.33% Triton X-100, incubated for 2 minutes at 70° C., and 110 µL of each was transferred to the slide wells. The slides were incubated in a humid chamber at 45° C. overnight. Samples were removed and rinsed three times with 150 µL SB17, 0.1% Tween-20, 0.33% Triton X-100, 1 M guanidine hydrochloride at 45° C. The gasketed slides were disassembled, placed in a pap jar containing 30 mL SB17, 0.1% Tween-20, 0.33% Triton X-100, 1 M guanidine hydrochloride, and mixed by rotation for 20 minutes at 45° C. Slides were then transferred to a pap jar containing 30 mL SB17, 0.1% TWEEN-20 and mixed by rotation for 2 minutes at 20° C., transferred to a pap jar containing 30 mL 0.2×SB17, 0.02% TWEEN-20 for 15 seconds without mixing, and dried, scanned, and quantified as described in Example 2.

Figure 9A:
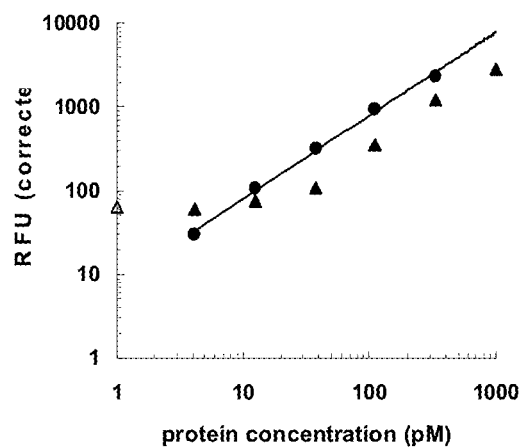
FIGS. 9A, 9B and 9C show dose response curves for three target proteins (tPA (FIG. 9A), PAI-1 (FIG. 9B), and IL-6 (FIG. 9C)) in buffer (●) and plasma (▲). RFU values have been corrected by subtracting the no-protein buffer RFU value for each aptamer. The least-squares line fit to the log transformed data is also plotted for the buffer data. The corrected no-protein plasma RFU values for these aptamers (▲ at 1 pM) are 66, 26, and 49 RFU, respectively.
Figure 9B:
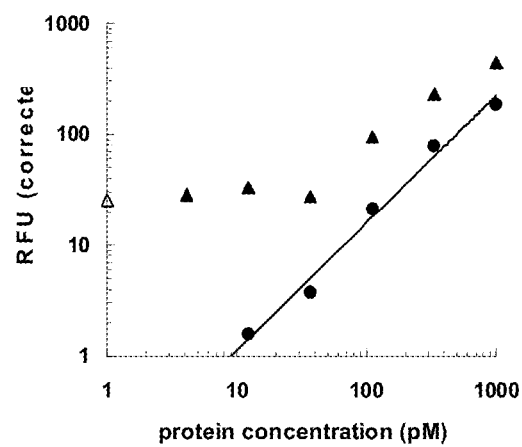
Figure 9C:
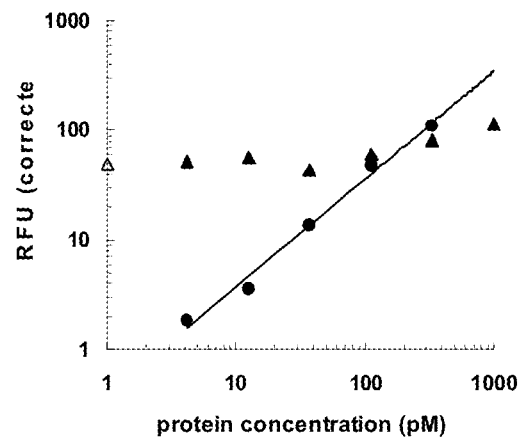

FIG. 9 shows a graphical representation of the results for tPA aptamer 987-51 (FIG. 9A), PAI-1 aptamer 1152-46 (FIG. 9B), and IL-6 aptamer 1920-1 (FIG. 9C) in buffer (●) and plasma (▲). RFU values have been corrected by subtracting the no-protein buffer RFU value for each aptamer. The corrected no-protein plasma RFU values for these aptamers (A at 1 pM) are 66, 26, and 49 RFU, respectively.

Example 7. Removal of Free Photoaptamer in the Photoaptamer Assay Using Hybridization Capture by Probes Immobilized on a Surface This example illustrates the optional step of removing free aptamer prior to hybridization capture on the surface, as depicted in FIG. 3. The free aptamer is removed by precipitation of protein and aptamer-protein covalent complexes by K+/SDS while free aptamer remains in solution. The supernatant containing free aptamer is discarded and the pellet is suspended to complete the step.

A. Preparation of Tagged Photoaptamers.

The tagged photoaptamer was prepared as described in Example 2.

B. Immobilization of Capture Probes onto an Amine Reactive Surface.

The reverse complements of the capture tags were immobilized as described in Example 2.

Binding reactions were prepared in SB18 as described in Example 1 to contain a 2 nM final concentration of photoaptamer and serially diluted target proteins from 2 nM-0.64 pM in addition to a no protein control. The reactions were incubated at 37° C. for 30 minutes and irradiated as described in Example 1. The samples were transferred to 1.5-ml eppendorf tubes and 10 µL of pooled plasma was added. 300 µL of the following SDS solution was added to each sample: 1.33% SDS, 1.33 µg/ml tRNA and 10 mM HEPES (pH 7.5) (400 µL final volume). The samples were vigorously vortexed for 10 seconds, then incubated at 37° C. for 10 minutes. 6 µL of 2.5 M KCl was added to each reaction and the samples were vigorously vortexed for 10 seconds then held on ice for 10 minutes. Precipitates were pelleted by centrifugation at 8,000 g for 5 minutes at 4° C. in a microcentrifuge. Resulting supernatants were discarded. The pellets were washed by adding cold 200 mM KCl, 10 mM HEPES (pH 7.5), followed by gentle vortex mixing for 5 seconds. The precipitate was again pelleted by centrifugation at 8,000 g for 5 minutes at 4° C. Wash supernatants were discarded. Each pellet was suspended in 200 µL of warm (>37° C.) 1 mM EDTA, 10 mM HEPES (pH 7.5). Paramagnetic beads, described in Example 4, were added to each sample and the bead suspension was vigorously mixed at 50° C. for 30 minutes. Using a microwell plate magnet, the beads were washed 3 times with 100 µL SB17, 0.1% Tween® 20 buffer. The beads were suspended in carbonate buffer (pH 8.5) containing 0.2 mg/ml of the amine-reactive NHS-Alexa647 and incubated at 25° C. for 60 minutes with constant mixing. The reaction was quenched, the beads were washed, aptamers eluted and hybridized as described in Example 4. The slides were scanned and quantified as described in Example 1.

FIG. 10 shows the results for samples treated with and without free aptamer removal. The signals are higher when uncomplexed aptamers are removed from the sample prior to introducing the sample to the probes.

Example 8. Generation of UPS Assay Signal Under Conditions that Affect Signal from Aptamer Affinity Complex but not Aptamer Covalent Complex This example demonstrates the effect of covalent attachment of a target molecule to its photoaptamer when detergent and a high salt concentration are used during hybridization of the photoaptamer complex to its probe on the solid support. The results of an assay performed both with and without covalent cross-linking, mediated here by photoactivation, are compared for a plasma sample and a sample containing bFGF in buffer.

A. Preparation of Tagged Photoaptamer 6-7.

The oligonucleotide tag used here was the 3' fixed region used during the SELEX protocol. The bFGF photoaptamer 6-7 was synthesized as described in Example 1.

B. Immobilization of Capture Probes onto an Amine Reactive Surface.

The reverse complements of the capture tags were immobilized as described in Example 1.

1 nM 6-7 was prepared in the buffer and plasma binding solutions as described in Example 1. 10 nM bFGF protein was added to the buffer sample only. The samples were mixed gently and incubated at 37° C. for 30 minutes. One set of samples was irradiated as described in Example 1 and a duplicate set of samples was not irradiated. Samples were then stained as described in Example 1 except the reaction time was 3 hours at room temperature followed by the addition of 10 µL of BSA, 25 µL of 5 M NaCl, and 5 µL of 10% Triton X-100 and a 2 hour incubation. The slide was prepared as in Example 1 and 80 µL of a pre-hybridization solution (500 µL of 5 M NaCl and 100 µL of 10% Triton to 2 mL of sample buffer) was added to each well for 15 minutes at 42° C. The pre-hybridization solution was removed and replaced with 80 µL of sample. The wells were sealed with Microseal 'F' Film and the slides were then mixed at 600 rpm, 40° C. on an Eppendorf Thermomixer R for 2 hours, followed by 20 minutes at 35° C. The wells were rinsed twice with 1×SB17, 0.5% Triton, 1 M NaCl and then incubated in the second wash for 15 minutes. After hybridization, the slide was treated as described in Example 1 except the 3 wash times were 15 minutes, 2 minutes, and 30 seconds. The slide was dried, scanned, and quantified as described in Example 1.

Figure 11:
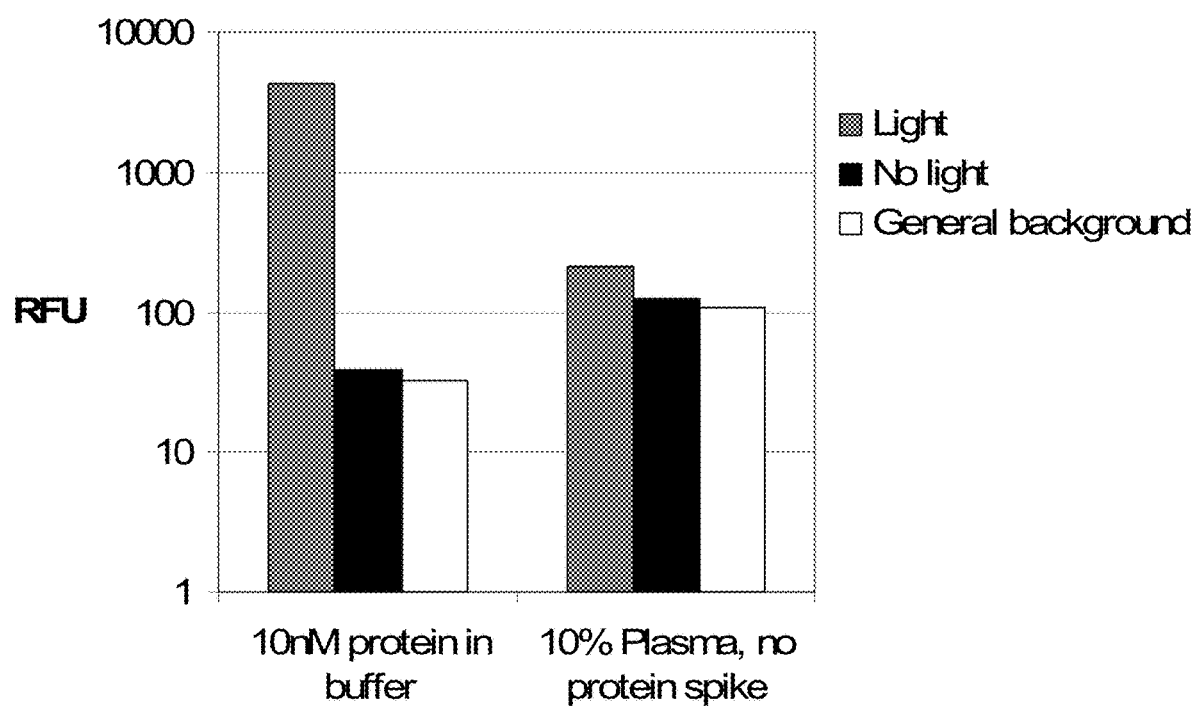
FIG. 11 shows the effect of light-induced chemical cross-linking of a target protein (bFGF) to its photoaptamer when detergent and a high salt concentration are used during hybridization. In the absence of light, and therefore absence of covalent attachment of the target to its photoaptamer, the assay signal is reduced over two orders of magnitude in buffer. The endogenous concentration of bFGF is quite low, reflected in the small signal over the no-light control and general background response.

The results for bFGF photoaptamer 6-7 are presented in FIG. 11. The signals obtained for 10 nM bGFG in buffer and in 10% plasma are seen to be dependent on light. The signal on the no-light samples, where covalent attachment of target to photoaptamer cannot occur, are comparable to the signal observed outside a feature, termed "general background" here. The endogenous concentration of bFGF in 10% plasma is quite low as reflected in the small signal in plasma over the no-light and general background response.

Example 9. Detection of C4b Crosslinked to a DNA Photoaptamer Comprised of 5-benzyl-dT and 5-bromo-dC Nucleotides in Buffer This example illustrates the activity of photoaptamers containing modified nucleotides in the assay format illustrated in FIGS. 2A, 2B, and 2C. The DNA photoaptamer (1987-74) to protein C4b is composed of 5-benzyl-dT and 5-bromo-dC nucleotides in place of standard dT and dC.

A. Preparation of Tagged Photoaptamer 1987-74.

Vector inserts containing the aptamer sequences were amplified from E. coli cells by PCR with primers specific for the aptamer fixed regions. The 3' primer was biotinylated, allowing capture of the PCR product on MyOne-streptavidin beads. After washing, the non-biotinylated strand of the captured duplex was removed with a 20 mM NaOH wash and the aptamers were created by primer extension with an oligonucleotide with a unique capture tag coupled to the 5' primer sequence. Primer extension was performed with the template DNA still coupled to the streptavidin bead in a mixture containing dATP, 5-Br-dCTP, dGTP and 5-benzyl-dUTP using KOD DNA polymerase to incorporate the modified nucleotides. Aptamer was collected from the beads with a 20 mM NaOH wash followed by neutralization with HCl.

B. Immobilization of Capture Probes onto an Amine Reactive Surface.

The reverse complements of the capture tags were immobilized as described in Example 1.

A final concentration of 2 nM 1987-74 was incubated with a dilution series of C4b protein in SB17, 0.1% Tween® 20 at the following concentrations: 25 nM, 5 nM, 1 nM, 0.2 nM, 0.04 nM and a no-protein control. The samples were equilibrated and irradiated as in Example 1, after which 2 µL of herring sperm DNA (10 mg/mL) was added. C4b protein was fluorescently labeled by addition of 7.5 µL NHS-Alexa-647 (1.33 mg/mL in DMSO) to each sample and incubated for 2 hours at room temperature. 25 µL 5 M NaCl, 5 µL 10% Triton-100 and 1 µL 100 mM glycine were added to quench unreacted label, disrupt noncovalent interactions and facilitate subsequent hybridization.

Gasketed slides were prepared as described in Example 1 and incubated with a solution containing SB17, 0.1% Tween® 20, 0.8 M NaCl, 20 µg/mL herring sperm DNA and 0.33% Triton X-100 for 15 minutes at 42° C. After removing the solution, 80 µL of labeled sample was added to the slide, one per subarray, and incubated for 30 minutes at 42° C. on a rotating platform. Samples were removed and the substrates were washed twice with the pre-hybridization solution, once with pre-hybridization solution without herring sperm DNA or Tween® 20, once with 1×SB17, 0.1% Tween® 20, and once with 0.25×SB17. Slides were then dried, scanned and quantified as described in Example 1.

Figure 12:
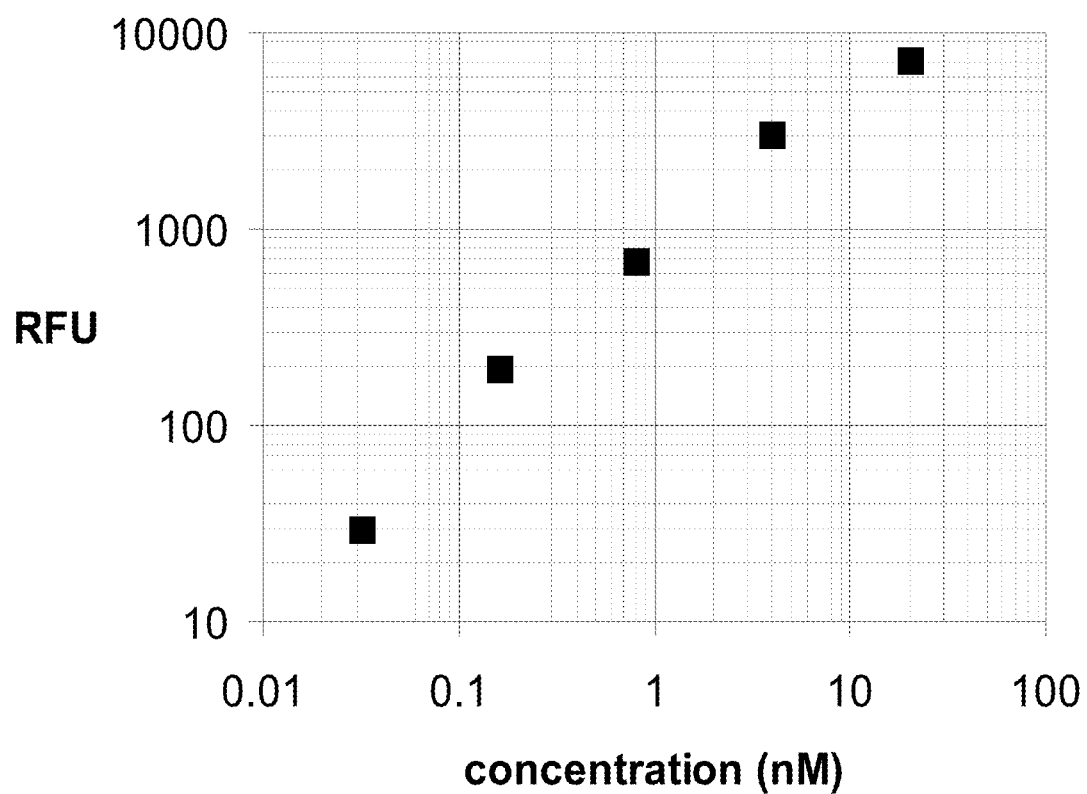
FIG. 12 shows the dose response in buffer of a target protein (C4b) using a photoaptamer developed with a modified library of 5-benzyl-dT in place of dT. The linear response over 3 logs of target concentration demonstrates the activity of the modified nucleotide aptamer in the assay.

FIG. 12 shows the resulting dose response curve of 1987-74 obtained as a function of target concentration, illustrating the activity of modified nucleotide aptmers in the assay.

Example 10. UPS Hybridization Capture Assay on Two Different Surfaces Using Two Independent Staining Methods This example demonstrates the functionality of the assay on two surfaces of different composition, the methacrylate copolymer surface of the previous examples and a Schott Nexterion amine reactive surface on a glass substrate. In addition, the target protein staining reaction is carried out as in previous examples by direct attachment of Alexa-647 to the target protein or by first tagging the target protein with biotin followed by labeling with streptavidin-Alexa-647. The assay allows quantitative detection of VEGF protein in buffer using either surface or staining method.

A. Preparation of Tagged Photoaptamer 509-80.

The tagged photoaptamers were prepared as described in Example 1.

B. Immobilization of Capture Probes onto Amine Reactive Surface.

The capture probe with a 5' amine was synthesized as described in Example 1 and immobilized on both surfaces. Immobilization on the Schott Nexterion slide was accomplished by dissolving the probe at either 40 or 20 µM in a buffer composed of 300 mM sodium phosphate (pH 8.5), 0.005% Tween® 20 and 0.001% sarkosyl. Capture probes were deposited as described in Example 1. After probe deposition the slides were incubated overnight in a dry box and then incubated with 100 mM sodium bicarbonate (pH 8.5) and 0.1% Tween® 20 for 8 hour at room temperature. The slides were then rinsed with water 10 times and dried under a stream of $N_2$. Capture probe was immobilized on the methacrylate copolymer surface by the protocol described in Example 1.

VEGF Aptamer 509-80 was incubated at 1 nM concentration in 100 µL volume with 6 serially diluted VEGF concentrations, from 50 nM to 16 pM, and a no-protein control in assay diluent (SB17, 0.1% Tween® 20, 0.05% BSA, 100 µg/mL herring sperm DNA). The samples were mixed gently and incubated at 37° C. for 15 minutes followed by irradiation as described in Example 1. The samples were split and stained directly with NHS-Alexa-647 or by reaction with NHS-PEO$_4$-biotin and subsequently stained with streptavidin Alexa-647. For staining with NHS-Alexa-647, the procedure of Example 1 was used, except the reaction was at room temperature for 4 hours. For reaction with NHS-PEO$_4$-biotin, 1 µL of 20 mM NHS-PEO$_4$-biotin dissolved in DMSO was added to 100 µL of sample. The solution was mixed and incubated at room temperature for 4 hours. Both stain reactions were quenched by the addition of 23 µL of 5 M NaCl, 11.4 µL of 10% BSA and 1.1 µL of 10% Triton X-100 and allowed to incubate for 2 hours.

The two different slides were gasketted as described in Example 1 and pre-hybridized with 1×SB17, 0.1% Triton X-100, 0.5% BSA and 100 µg/mL hsDNA for 15 minutes at 42° C. The solution was then removed and replaced with 80

µL of sample. The wells were sealed with Microseal 'F' Film and the slides mixed at 600 rpm, 42° C. on an Eppendorf Thermomixer R for 3 hours followed by 1 hour at 34° C. For the samples labeled directly with NHS-Alexa-647, the wells were rinsed 3 times with 1×SB17, 0.5% Triton and 1 M NaCl. The gasket was removed and the entire slide was placed in a pap jar in 30 mL of SB17, 0.5% Triton, 1 M NaCl for 30 minutes, followed by a 2 minute rinse in 1×SB17, 0.1% Tween® 20, followed by a 20 second rinse in 0.25× SB17. For the samples that had been reacted with NHS-$PEO_4$-biotin, the wells were rinsed 3 times with 1×SB17, 0.1% Tween® 20, 0.5 M NaCl, 100 µg/mL herring sperm DNA, 0.5% BSA (streptavidin staining buffer). A solution of 4 µg/mL of streptavidin Alexa-647 was prepared in streptavidin staining buffer and 80 µL of this solution was added to each well for 15 minutes at 37° C. The wells were then rinsed 3 times with 1×SB17, 0.1% Tween® 20. The gasket was removed and the entire slide was placed in a 30 mL pap jar in 1×SB17, 0.1% Tween® 20 for 30 minutes, followed by a 20 second rinse in 0.25×SB17. The slides were dried, scanned and quantified as described in Example 1.

FIG. 13 displays the results for the Schott Nexterion (FIG. 13A) and methacrylate copolymer surface (FIG. 13B) for the dose response as a function of protein concentration. Both surfaces give similar quantitative results, demonstrating the surface-independence of the assay. The two staining strategies are seen to be comparably effective as well.

Example 11. Detection of Target Proteins VEGF and bFGF in Buffer and Serum by Hybridization Capture of the Photocrosslinked Proteins on an Affymetrix GeneChip® Test3 Array on a Coated Quartz Surface This example demonstrates the utility of yet another surface, an Affymetrix GeneChip® Test3 Array (quartz glass surface), for the hybridization capture step of the assay. Assays were run in both buffer and serum.

A. Synthesis of Tagged Photoaptamer 509-80 and 6-7.

The reverse complements of the two probes designated 201 and 1121 on the Affymetrix GeneChip® Test3 Array were assigned to aptamers 509-80 and 6-7 and prepared as described in Example 1.

B. Immobilization of Capture Probes onto Amine Reactive Surface.

A GeneChip® Test3 Array was purchased from Affymetrix with probes that were synthesized in situ.

A 100 µL volume of VEGF aptamer 509-80 and bFGF aptamer 6-7, each at a concentration of 2 nM, was prepared with 20 nM VEGF and bFGF protein in assay diluent (1×SB17, 0.1% Tween® 20, 0.02% BSA, 100 µg/mL herring sperm DNA). The samples were mixed gently and incubated at 37° C. for 60 minutes, then irradiated and stained with NHS-$PEO_4$-biotin as described in Example 9, except the reaction time was 1 hour. The reaction was quenched by the addition of 10 µL of 10% BSA, 1 µL of 10 mg/mL herring sperm DNA, 5 µL of 10% Triton X-100, and 25 µL of 5 M NaCl. 10 µL of serum was added to one sample to approximate a 10% serum sample.

Figure 14A:
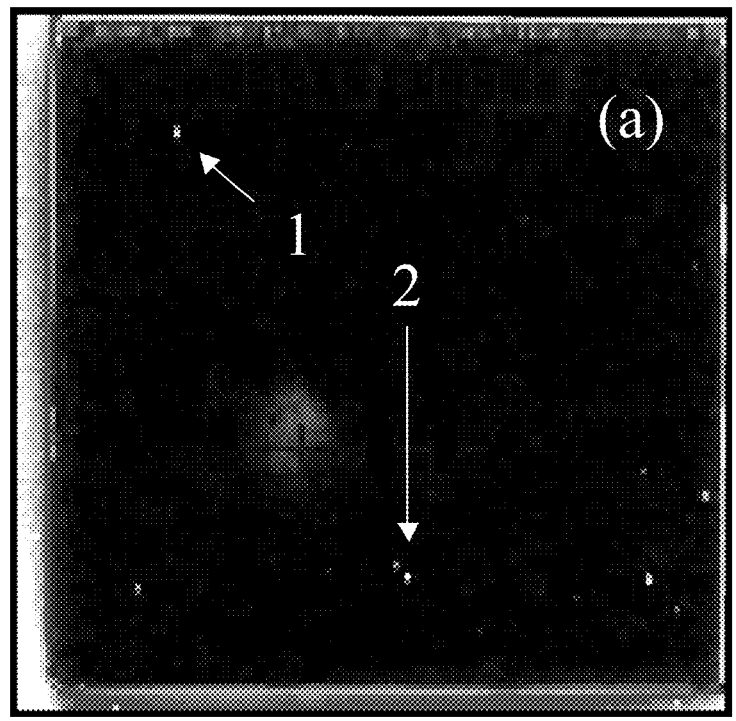
FIGS. 14A and 14B illustrate the hybridization of aptamer-target complexes from either buffer (FIG. 14A) or 10% serum (FIG. 14B) and labeled with NHS-PEO$_4$-biotin on an Affymetrix GeneChip® Test3 Array. The staining with Phycoerythrin-R is done on an Affymetrix GeneChip® fluidics station. In buffer (FIG. 14A), the VEGF aptamer hybridizes to probe 201 (1) with an intensity of 3500 RFU, and the bFGF aptamer hybridizes to probe 1121 (2) with an intensity of 23000 RFU. In serum (FIG. 14B), the relative intensities are 5000 (1) and 18000 (2) for the VEGF and bFGF aptamers, respectively.
Figure 14B:
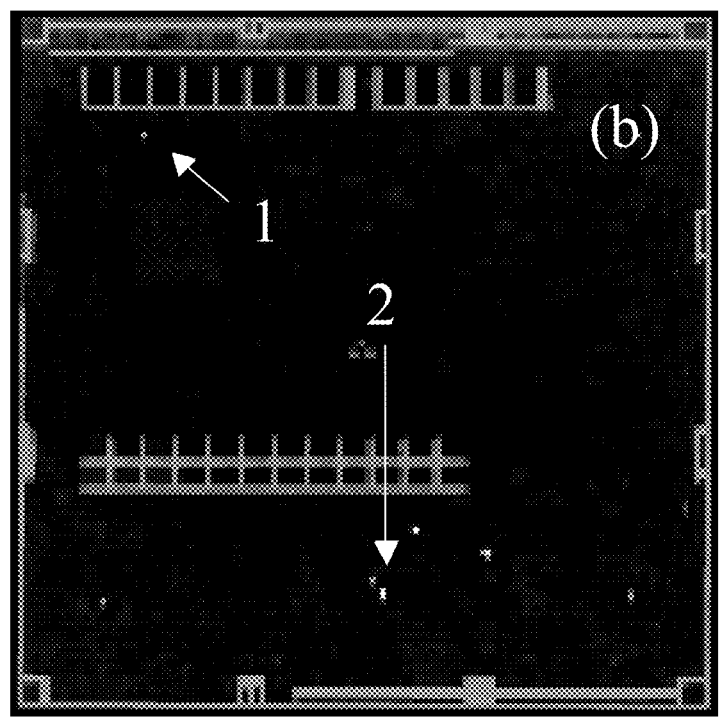
Figure 15A:
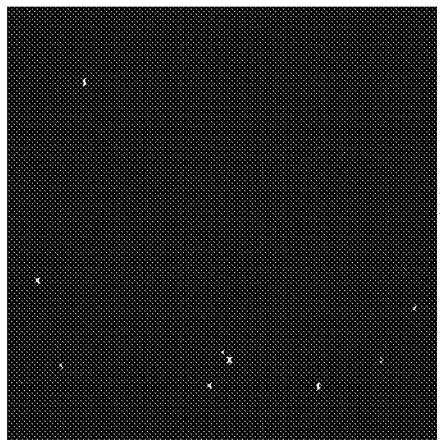
FIGS. 15A, 15B, 15C and 15D illustrate the effect of blocking an Affymetrix GeneChip® Test3 Array prior to hybridization of aptamer-target complexes from plasma samples. Biotinylated probes were hybridized in buffer (FIG. 15A) and in plasma samples to surfaces blocked with nonfat milk (FIG. 15B), "starter block" (FIG. 15C), and unlabeled plasma (FIG. 15D). The background values for these four surfaces are 49, 300, 400 and 500 RFU while the hybridization signals for the three probes are 16,000, 33000 and 18000 in (FIG. 15A) and (FIG. 15B), 17000, 35000, and 18000 in (FIG. 15C) and 20000, 36000 and 18000 in (FIG. 15D).
Figure 15B:
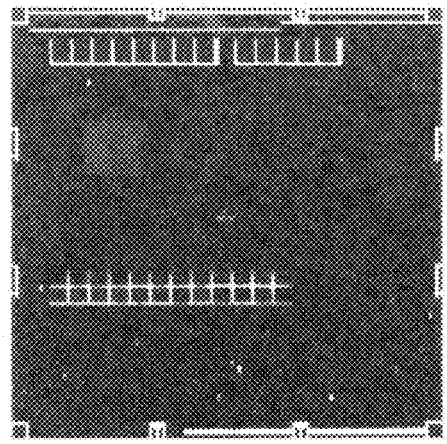
Figure 15C:
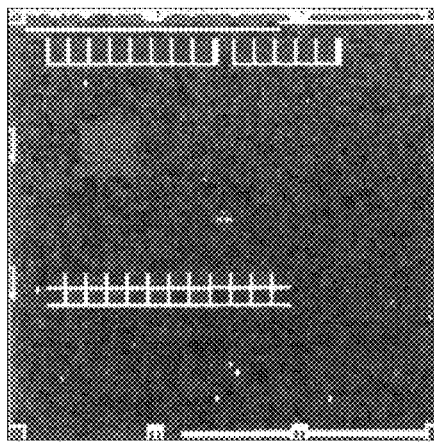
Figure 15D:
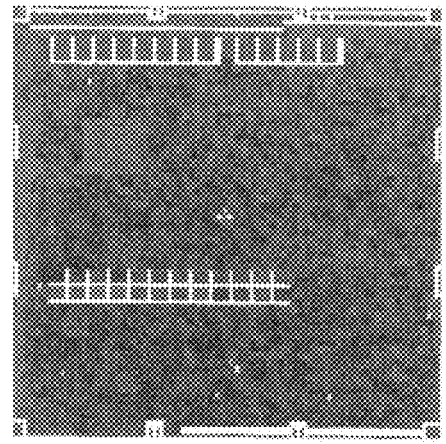

GeneChip® Test3 Arrays from Affymetrix were incubated with 100 µL of a solution composed of 100 µL of assay diluent, 10 µL of 10% BSA, 1 µL of 10 mg/mL herring sperm DNA, 25 µL of 5 M NaCl, 5 µL of 10% Triton X-100 and 7 µL of DMSO for 1 hour at 45° C., after which 100 µL of sample was added to the Test3 Array chamber and incubated for 60 minutes at 45° C. then rinsed with a buffer composed of 1×SB1, 0.5% Triton X-100 and 1 M NaCl. The arrays were then placed on the Affymetrix GeneChip® fluidics station, which performed the standard Affymetrix wash and stain procedures. The arrays were then read and quantified on the Affymetrix scanner. The results are set forth in FIG. 14. In buffer (FIG. 14A) the VEGF aptamer hybridizes to probe 201 (denoted 1 in the figure) with an intensity of 3500 RFU and the bFGF aptamer hybridizes to probe 1121 (denoted 2 in the figure) with an intensity of 23000 RFU. In serum (FIG. 14B) the relative intensities are 5000 (1) and 18000 (2) for the VEGF and bFGF aptamers.

Example 12. Surface Passivation of an Affymetrix GeneChip® Test3 Array on a Coated Quartz Surface by Pre-Blocking with Nonfat Milk, Superblock or Unstained Plasma This example illustrates surface passivation to serum and plasma adsorption on an Affymetrix GeneChip® Test3 Array by blocking with nonfat milk, Superblock, or unstained plasma.

A. Preparation of Biotinylated Oligonucleotides.

Biotinylated oligonucletides that anneal to three different probes immobilized on the GeneChip® Test3 Array, denoted 201, 1121, and 108, were synthesized as described in Example 1.

B. Plasma Biotinylation.

160 µL of 21 mM NHS-$PEO_4$-biotin was added to 100 mL of 10% plasma in 1×SB18, 0.1% Tween® 20 and the solution was allowed to react for 2 hours and then quenched with the addition of 1 mL of 100 mM glycine (pH 7.5). The biotinylated plasma was stored at −20° C.

The control buffer is comprised of 0.75×SB17, 0.1% BSA, 100 µg/mL herring sperm DNA, 0.1% Tween® 20 and 0.8 M NaCl. 10% biotinylated plasma was prepared with the control buffer and biotinylated plasma. The plasma was pretreated by adding 50 µL of 10% Triton X-100, 10 µL of 10% SDS and 10 µL of 10 mg/mL herring sperm DNA to 1 mL of 10% biotinylated plasma, heating to 95° C. for 10 minutes and then adding 200 µL of 5 M NaCl. 1 µL of 1000× biotinylated probe mix was added to 1 mL of either control buffer or 10% plasma.

Four Affymetrix Test3 Arrays were incubated with 1×SB17, 1% BSA, 0.4% Triton X-100, 0.1% SDS, 1 M NaCl and 100 µg/mL herring sperm DNA. Array B was blocked with a solution of 2% non-fat Dry Milk (Nestle Carnation, INSTANT NONFAT DRY MILK) suspended in PBS, 0.1% SDS and 0.4%. Array C was blocked with a solution of StarterBlock (PIERCE), 0.1% SDS and 0.4%. Array D was blocked with a solution of 10% pooled plasma, 0.1% SDS and 0.4% Triton X-100. Each blocking solution was heated to 95° C. for 10 minutes and allowed to cool to room temperature before addition to the array. Each Test3 Array was blocked with 100 µL of the respective blocking solution for 1.5 hours at 45° C. 100 µL of sample was then added to each array. Array A received the control buffer with probes and Arrays B, C, and D received the 10% plasma with probes. The arrays were incubated at 45° C. for 45 minutes.

The arrays were then rinsed with 1×SB17, 0.4% Triton X-100, 0.1% SDS, 1 M NaCl, 1% BSA by flowing 1 mL of wash through the chamber, allowing the array to incubate for 5 minutes, then flowing another 1 mL through the chamber and finally replacing the final 100 µL of wash with 100 µL of fresh wash. This procedure was performed 3 times. The arrays were incubated for approximately 1 hour before being placed on the Affymetrix GeneChip® fluidics station and read on the Affymetrix scanner.

The results are set forth in FIGS. 15A-D. The general background on the four arrays was 40, 300, 400 and 500 RFU, whereas the three biotinylated probes measure ~17,000, ~34000 and 18000 on the arrays.

Example 13. Detection of Target Proteins by Hybridization Capture of Photocrosslinked Proteins on a GeneChip® Test3 Array Pre-Blocked with Nonfat Milk This example illustrates the hybridization capture of target proteins IL-1 R4 and bFGF on an Affymetrix GeneChip® Test3 Array on coated glass surfaces blocked with nonfat milk.

A. Synthesis of Tagged Photoaptamer 1472-3 and 6-7.

The reverse complements of two probes denoted 1364 and 1121 on the Affymetrix GeneChip® Test3 Array were assigned to aptamers 1472-3 and 6-7 and synthesized as described in Example 1.

Four solutions, each containing 2 nM concentration of each aptamer 1472-3 and 6-7, were prepared in 10% plasma to give the following final concentrations for the protein pairs (IL-1 R4, bFGF): (0,0), (1 nM, 30 pM), (100 pM, 1 nM), and (10 pM, 100 pM). The plasma diluent contained 0.9×SB18, 100 µg/mL herring sperm DNA, 5 µg/mL (BrdU)$_{30}$, 0.1% Tween® 20 and 10% plasma. The samples were incubated at 37° C. for 30 minutes and irradiated as described in Example 1. 1 µL of 5 mg/mL NHS-PEO$_4$-biotin in DMSO was added to each sample and incubated for 2 hours at room temperature, after which 2 µL of 100 mM glycine (pH 7.5), 1 µL of 10% SDS and 5 µL of 10% Triton X-100 were added. Samples were then heated to 95° C. for 10 minutes, allowed to cool to room temperature and quenched with the addition of 10 µL of 10% BSA and 25 µL of 5 M NaCl. 1 µL of 100× probe-108 was then added as a control sequence.

Figure 16:
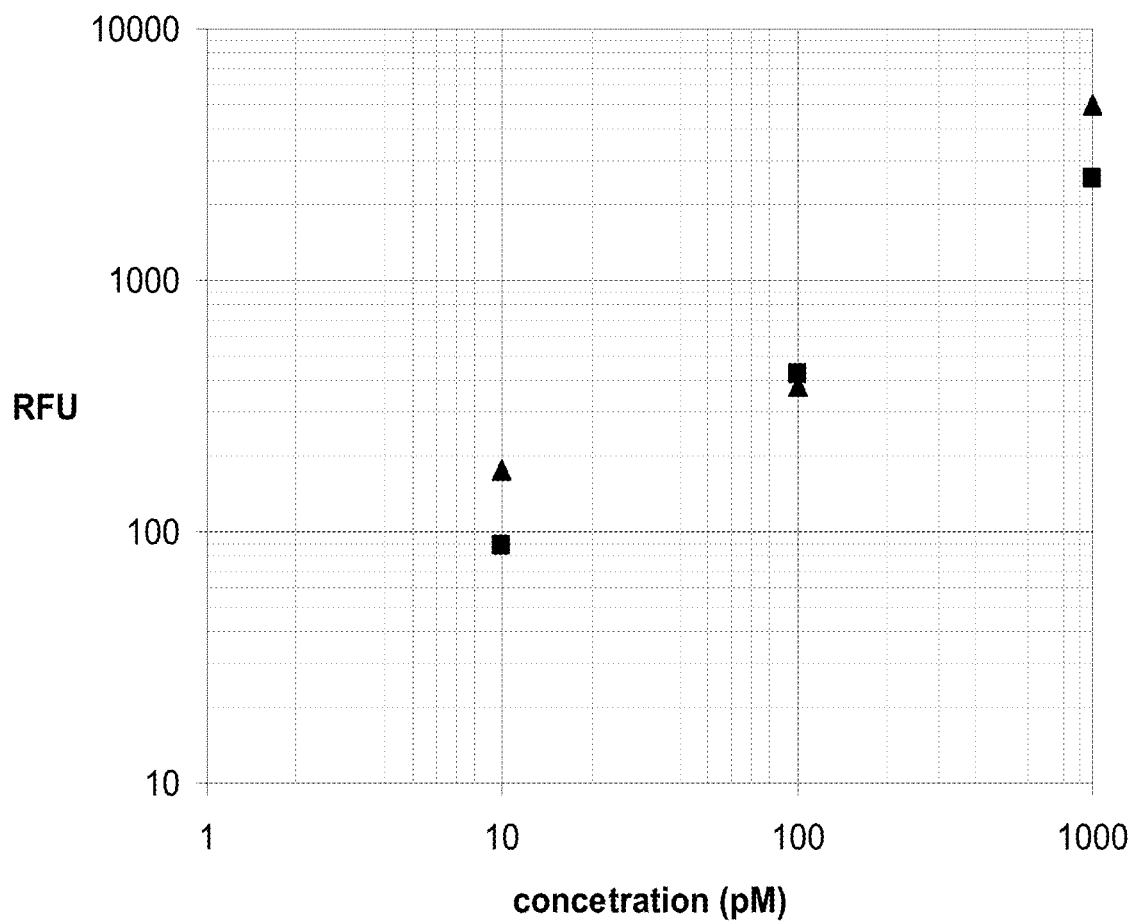
FIG. 16 illustrates the quantitative detection of target proteins added to plasma, cross-linked to photoaptamers, and hybridized on an Affymetrix GeneChip® Test3 Array. The hybridization response for aptamer complexes of the target proteins IL1-R4 (▲) and bFGF (■) formed in plasma have the no-protein response RFU value subtracted. A two-log quantification range is seen from the plasma samples after blocking the array surface to reduce adsorption of molecules in the sample matrix.

Four Test3 Arrays were blocked for 3 hours at 45° C. with the nonfat dry milk solution described in Example 11 for Array B. The arrays were then rinsed with PBS, 0.1% SDS and 0.4% Triton X-100 and then incubated with 1×SB17, 1% BSA, 0.5% Triton X-100, 0.1% SDS, 1 M NaCl and 0.1 mg/mL herring sperm DNA for 20 minutes at 45° C. 100 µL of each sample was then added to a separate array. The arrays were incubated at 45° C. for 45 minutes. The assay was then completed as described in Example 12. The results are presented in FIG. 16, where linear dose responses are observed for both targets in plasma.

Example 14. Detection of Target Proteins C5b,6 Complex, Neurotropin-3, and Troponin I by Hybridization Capture of the Photocrosslinked Proteins on Luminex SeroMap™ Microspheres This example demonstrates the use of Luminex SeroMap™ microspheres as a solid support for detecting and optionally quantifying a target molecule that may be present in a test sample. These assays were performed with target proteins spiked into buffer. The detection instrument was a Luminex 100 IS instrument system.

Amine-terminated probes assigned to the photoaptamers 2184-64 (C5b,6 complex aptamer), 2273-34 (neuropthropin-3 aptamer), and 2338-12 (Troponin I aptamer) were conjugated to —COOH functionalized SeroMap™ microspheres using EDC (1-ethyl-3-[3-dimethylaminopropyl]carbodiimide hydrochloride) chemistry.

Photoaptamers 2184-64, 2273-34, and 23338-12, at a final assay concentration of 2 nM each, were pre-annealed to biotinylated oligonucleotides complementary to the aptamer 3' ends then combined with a mixture of the proteins C5b,6 complex, neurotropin-3, and troponin I at a range of concentrations (169 fM to 3.33 nM) in buffer SB17, 0.05% Tween® 20. Duplicate no-protein control assay samples were also prepared. These assay samples, in 100 µL volumes, were incubated at 37° C. for 15 minutes and then photocrosslinked. Dynal MyOne Streptavidin beads (400 µg) were added to each assay sample and incubated for 10 minutes at 25° C. with mixing to capture the photoaptamer: biotinylated oligo and protein-photoaptamer:biotinylated oligo hybrids. The beads were washed 2 times for 30 seconds each with 100 µL 100 mM sodium bicarbonate, 1 mM EDTA, 0.02% Tween® 20, and 10 µM D-biotin (pH 8.5). The purpose of the D-biotin component of this buffer was to saturate free streptavidin binding sites. The washed beads were suspended in 100 µL 100 mM sodium bicarbonate (pH 8.5), 1 mM EDTA, 0.02% Tween® 20, and 150 µM sulfo-NHS-LC-biotin (Pierce Biotechnology) for the purpose of labeling the photoaptamer-conjugated target protein with biotin. This biotinylation reaction was incubated at 25° C. for 1 hour with constant mixing. The beads were then washed 3 times with 100 µL SB17, 3.14 M guanidine hydrochloride, 0.05% Tween® 20 followed by washing 2 times with 100 µL SB17, 0.33% Triton X-100. The washed beads were suspended in 100 µL 10 µM D-biotin, 0.05% Tween® 20, 10 mM HEPES, pH 7.5 then heated at 70° C. for 5 min to release the photoaptamers from their bead-bound complementary biotinylated oligonucleotides. For each assay sample, 75 µL of the bead eluate volume was combined with 25 µL of the following high salt buffer: 4 M NaCl, 0.4% Tween® 20, 160 mM Tris-Cl, pH 8.0. SDS (11.25 µL of 20%) was added and each assay sample was transferred to a 30 µL mixture of the appropriate probe-conjugated SeroMap™ microspheres (1500 color-coded microspheres per probe, 0.1% Tween® 20, 1M NaCl, 1.25% BSA, 40 mM Tris-Cl, pH 8.0). To promote hybridization of the photoaptamers to the microsphere-conjugated probes, the assay samples were incubated at 65° C. for 2 hours with constant mixing. While at 65° C., the assay samples were transferred to a 96-well microtiter vacuum filtration plate and the microspheres were washed 4 times with 200 mM NaCl, 0.1% Tween® 20, 40 mM Tris-Cl (pH 8.0) at 65° C. The microspheres were then suspended in 80 µL of 200 mM NaCl, 0.1% Tween® 20, 40 mM Tris-Cl (pH 8.0) and transferred to 96-well microtiter plate. 20 µL of 10 µg/ml streptavidin-R-phycoerythrin (Molecular Probes # S866) was added to permit detection of the photoaptamer-crosslinked biotinylated target proteins. Following a 15 minute incubation at 37° C., the assay samples were subjected to a standard Luminex instrument signal (R-phycoerythrin) quantification protocol.

Figure 17A:
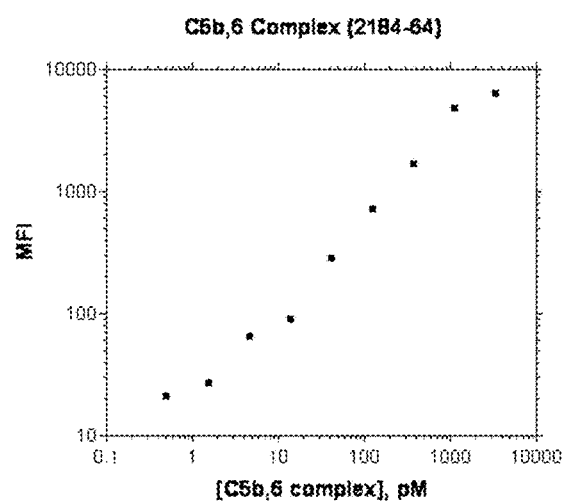
FIGS. 17A, 17B and 17C show target protein dose response values for serial dilutions of three target proteins multiplexed with photoaptamers in buffer. The photoaptamer-crosslinked target proteins were captured through hybridization to specific oligonucleotide probe-conjugated Luminex SeroMap™ microspheres. A Luminex 100 IS instrument system was used for signal quantification. The MFI (median fluorescence intensity) values have been corrected by subtracting the no-protein control MFI value for each aptamer.
Figure 17B:
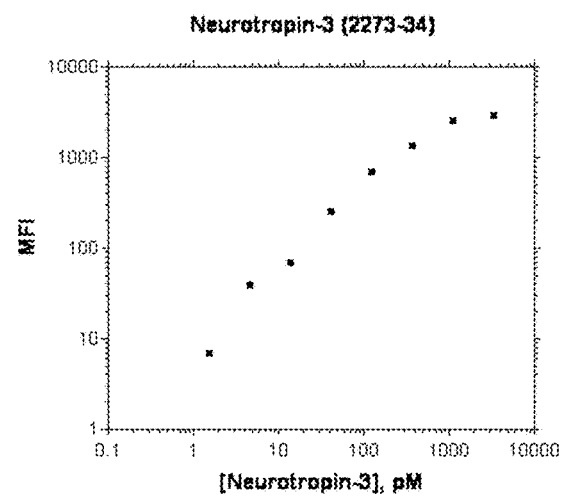
Figure 17C:
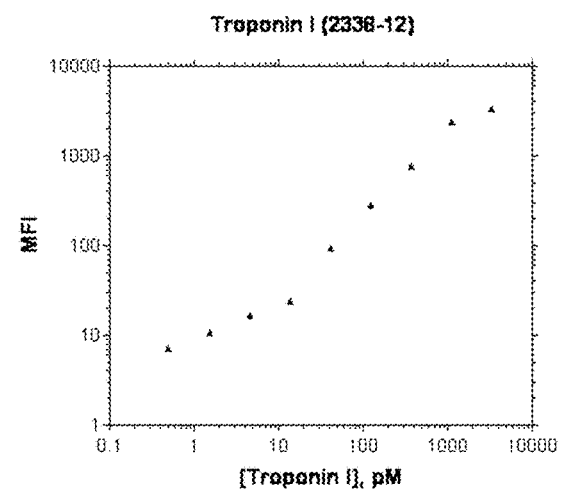

FIG. 17 graphically represents the results for C5b,6 complex photoaptamer 2184-64 (FIG. 17A), neurotropin-3 photoaptamer 2273-34 (FIG. 17B), and troponin I photoaptamer 2338-12 (FIG. 17C). The MFI (median fluorescence intensity) values have been corrected by subtracting the no-protein control MFI value for each aptamer.

The foregoing describes the invention with reference to various embodiments and examples. No particular embodiment, example, or element of a particular embodiment or example is to be construed as a critical, required, or essential element or feature of any of the claims. Further, no element described herein is required for the practice of the invention unless expressly described as "essential" or "critical."

It will be appreciated that various modifications and substitutions can be made to the disclosed embodiments without departing from the scope of the invention as set forth in the claims below. The specification, including the figures and examples, is to be regarded in an illustrative manner, rather than a restrictive one, and all such modifications and substitutions are intended to be included within the scope of the invention. Accordingly, the scope of the invention should be determined by the appended claims and their legal equivalents, rather then by the examples given above. For example, steps recited in any of the method or process claims may be executed in any feasible order and are not limited to an order presented in any of the embodiments, the examples, or the claims.

What is claimed is:

1. A kit for detecting at least one target molecule that may be present in a test sample, the kit comprising:
    at least one aptamer comprising a tag and having specific affinity for a target molecule;
    a labelling agent;
    a solid support comprising at least one probe;
    a buffer comprising HEPES, NaCl, KCl, $MgCl_2$, and EDTA, and
    a competitor molecule, wherein the competitor molecule is selected from dNTPs, abasic phosphodiester polymers, pyrophosphate, dextran sulphate, heparin and polydextran.

2. The kit of claim 1, wherein the aptamer comprises a 5-position pyrimidine modification.

3. The kit of claim 2, wherein the 5-position pyrimidine modification is selected from the group consisting 5-(N-benzylcarboxyamide)-2'-deoxyuridine, 5-(N-isobutylcarboxyamide)-2'-deoxyuridine, 5-(N-[2-(1H-indole-3yl)ethyl] carboxyamide)-2'-deoxyuridine, 5-(N-[1-(3-trimethylammonium)propyl]carboxyamide)-2'-deoxyuridine chloride, 5-(N-napthylcarboxyamide)-2'-deoxyuridine, and 5-(N-[1-(2,3-dihydroxypropyl)] carboxyamide)-2'-deoxyuridine.

4. The kit of claim 1, wherein the probe is capable of associating with the tag.

5. The kit of claim 1, further comprising washing solution for sample dilution.

6. The kit of claim 1, wherein the labelling agent includes a label and a binding partner that is specific for the target molecule.

7. The kit of claim 6, wherein the binding partner is an antibody, antibody fragment, synthetic antibody mimetic, biomimetic, aptamer or molecular imprinted ligand.

8. The kit of claim 6, wherein the label is selected from reporter molecules, specific binding pair members, mass tags, oligonucleotide primers and specific polynucleotide sequences.

9. The kit of claim 8, wherein the label is reporter molecule is a catalyst, enzyme, polynucleotide encoding the catalyst, promoter, dye, fluorescent molecule, quantum dot, chemiluminescent molecule, coenzyme, enzyme substrate, radioactive group, small organic molecule, amplifiable polynucleotide sequence, particle, latex particle, carbon particle, metal sol, crystallite, liposome, cell, mass tag that alters the weight of the molecule to which it is conjugated, electromagnetic or electrochemical material or fluorescent dye.

10. The kit of claim 9, wherein one or more of the kit components is provided as a dry powder.

* * * * *